United States Patent
Singer et al.

(10) Patent No.: US 7,314,916 B2
(45) Date of Patent: Jan. 1, 2008

(54) METHODS AND MATERIALS FOR CHARACTERIZING AND MODULATING INTERACTION BETWEEN HEREGULIN AND HER3

(75) Inventors: Elizabeth Singer, Duarte, CA (US); Ralf Landgraf, Van Nuys, CA (US); Dennis J. Slamon, Woodland Hills, CA (US); David Eisenberg, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/406,679

(22) Filed: Apr. 19, 2006

(65) Prior Publication Data

US 2006/0177907 A1    Aug. 10, 2006

Related U.S. Application Data

(62) Division of application No. 10/207,498, filed on Jul. 29, 2002, now Pat. No. 7,125,680.

(60) Provisional application No. 60/308,341, filed on Jul. 27, 2001.

(51) Int. Cl.
*C07K 14/00* (2006.01)
*C07K 17/00* (2006.01)

(52) U.S. Cl. ..................... 530/350; 530/402

(58) Field of Classification Search ............... None
See application file for complete search history.

(56) References Cited

U.S. PATENT DOCUMENTS 5,183,884 A    2/1993    Kraus et al.
5,804,396 A    9/1998    Plowman
5,811,098 A *  9/1998    Plowman et al. ......... 424/178.1
5,968,511 A    10/1999   Akita et al.

OTHER PUBLICATIONS

Aguilar et al., Oncogene, 1999, 18: 6050-6062.
Alimandi et al., Oncogene, 1995, 10: 1813-1821.
Carraway et al., J. Bio. Chem., 1994, 269(19): 14303-14306.
Chen et al., Biol. Chem., 1996, 271 (13): 7620-7629.
Fitzpatrick et al, FEBS Lett., 1998, 431: 102-106.
Guy et al., PNAS USA, 1994, 91(17): 8132-8136.
Heldin, Cell, 1995, 80: 213-223.
Huang et al., Biochem. J., 1998, 331: 113-119.
Hurwitz et al., J. Bio. Chem., 1991, 266: 22035-22043.
Kraus et al., PNAS USA, 1989, 86: 9193-9197.
Landgraf et al., Biochem., 2000, 39: 8503-8511.
Landgraf et al., Biochem., 1998, 37: 3220-3228.
Lee et al., Oncogene, 1998, 16(25): 3243-3252.
Lee et al., Cancer Res., 2001, 61(11):4467-4473.
Lemmon et al., EMBO J., 1997, 16: 281-294.
Marte et al., Oncogene, 1995, 10(1): 167-75.
Neve et al., Oncogene, 2000, 19(13): 1647-1656.
Singer et al., J. Bio. Chem., 2001, 276(47): 44266-44274.
Sliwkowski et al., J. Bio. Chem., 1994, 269: 14661-14665.
Tzahar et al., EMBO J., 1997, 16: 4938-4950.

* cited by examiner

*Primary Examiner*—Eileen B. O'Hara
*Assistant Examiner*—Xiaozhen Xie
(74) *Attorney, Agent, or Firm*—Gates & Cooper LLP

(57) ABSTRACT

The disclosure provided herein identifies and characterizes the domain in HER3 receptor that interacts with heregulin ligand. Typical embodiments of the invention disclosed herein include HER3 variant polypeptides having amino acid sequences which differ from the native HER3 polypeptide sequence and which have altered affinities for heregulin. Also disclosed herein are methods and materials for identifying compounds that bind to the heregulin binding domain in HER3 as well as methods and materials for modulating the interaction between HER3 and heregulin.

4 Claims, 16 Drawing Sheets

FIG. 8

HER3 Model

SEQUENCE LISTING

<160> NUMBER OF SEQ ID NOS: 24

<210> SEQ ID NO 1
<211> LENGTH: 4026
<212> TYPE: DNA
<213> ORGANISM: Homo sapiens
<220> FEATURE:
<221> NAME/KEY: CDS
<222> LOCATION: (1)...(4026)

<400> SEQUENCE: 1

| | | | | | | | | | | | | | | | | |
|---|---|---|---|---|---|---|---|---|---|---|---|---|---|---|---|---|
| atg | agg | gcg | aac | gac | gct | ctg | cag | gtg | ctg | ggc | ttg | ctt | ttc | agc | ctg | 48 |
| Met | Arg | Ala | Asn | Asp | Ala | Leu | Gln | Val | Leu | Gly | Leu | Leu | Phe | Ser | Leu | |
| 1 | | | | 5 | | | | | 10 | | | | | 15 | | |

| gcc | cgg | ggc | tcc | gag | gtg | ggc | aac | tct | cag | gca | gtg | tgt | cct | ggg | act | 96 |
|---|---|---|---|---|---|---|---|---|---|---|---|---|---|---|---|---|
| Ala | Arg | Gly | Ser | Glu | Val | Gly | Asn | Ser | Gln | Ala | Val | Cys | Pro | Gly | Thr | |
| | | | 20 | | | | | 25 | | | | | 30 | | | |

| ctg | aat | ggc | ctg | agt | gtg | acc | ggc | gat | gct | gag | aac | caa | tac | cag | aca | 144 |
|---|---|---|---|---|---|---|---|---|---|---|---|---|---|---|---|---|
| Leu | Asn | Gly | Leu | Ser | Val | Thr | Gly | Asp | Ala | Glu | Asn | Gln | Tyr | Gln | Thr | |
| | | 35 | | | | | 40 | | | | | 45 | | | | |

| ctg | tac | aag | ctc | tac | gag | agg | tgt | gag | gtg | gtg | atg | ggg | aac | ctt | gag | 192 |
|---|---|---|---|---|---|---|---|---|---|---|---|---|---|---|---|---|
| Leu | Tyr | Lys | Leu | Tyr | Glu | Arg | Cys | Glu | Val | Val | Met | Gly | Asn | Leu | Glu | |
| 50 | | | | | 55 | | | | | 60 | | | | | | |

| att | gtg | ctc | acg | gga | cac | aat | gcc | gac | ctc | tcc | ttc | ctg | cag | tgg | att | 240 |
|---|---|---|---|---|---|---|---|---|---|---|---|---|---|---|---|---|
| Ile | Val | Leu | Thr | Gly | His | Asn | Ala | Asp | Leu | Ser | Phe | Leu | Gln | Trp | Ile | |
| 65 | | | | | 70 | | | | | 75 | | | | | 80 | |

| cga | gaa | gtg | aca | ggc | tat | gtc | ctc | gtg | gcc | atg | aat | gaa | ttc | tct | act | 288 |
|---|---|---|---|---|---|---|---|---|---|---|---|---|---|---|---|---|
| Arg | Glu | Val | Thr | Gly | Tyr | Val | Leu | Val | Ala | Met | Asn | Glu | Phe | Ser | Thr | |
| | | | | 85 | | | | | 90 | | | | | 95 | | |

| cta | cca | ttg | ccc | aac | ctc | cgc | gtg | gtg | cga | ggg | acc | cag | gtc | tac | gat | 336 |
|---|---|---|---|---|---|---|---|---|---|---|---|---|---|---|---|---|
| Leu | Pro | Leu | Pro | Asn | Leu | Arg | Val | Val | Arg | Gly | Thr | Gln | Val | Tyr | Asp | |
| | | | 100 | | | | | 105 | | | | | 110 | | | |

| ggg | aag | ttt | gcc | atc | ttc | gtc | atg | ttg | aac | tat | aac | acc | aac | tcc | agc | 384 |
|---|---|---|---|---|---|---|---|---|---|---|---|---|---|---|---|---|
| Gly | Lys | Phe | Ala | Ile | Phe | Val | Met | Leu | Asn | Tyr | Asn | Thr | Asn | Ser | Ser | |
| | | 115 | | | | | 120 | | | | | 125 | | | | |

| cac | gct | ctg | cgc | cag | ctc | cgc | ttg | act | cag | ctc | acc | gag | att | ctg | tca | 432 |
|---|---|---|---|---|---|---|---|---|---|---|---|---|---|---|---|---|
| His | Ala | Leu | Arg | Gln | Leu | Arg | Leu | Thr | Gln | Leu | Thr | Glu | Ile | Leu | Ser | |
| | 130 | | | | | 135 | | | | | 140 | | | | | |

| ggg | ggt | gtt | tat | att | gag | aag | aac | gat | aag | ctt | tgt | cac | atg | gac | aca | 480 |
|---|---|---|---|---|---|---|---|---|---|---|---|---|---|---|---|---|
| Gly | Gly | Val | Tyr | Ile | Glu | Lys | Asn | Asp | Lys | Leu | Cys | His | Met | Asp | Thr | |
| 145 | | | | | 150 | | | | | 155 | | | | | 160 | |

| att | gac | tgg | agg | gac | atc | gtg | agg | gac | cga | gat | gct | gag | ata | gtg | gtg | 528 |
|---|---|---|---|---|---|---|---|---|---|---|---|---|---|---|---|---|
| Ile | Asp | Trp | Arg | Asp | Ile | Val | Arg | Asp | Arg | Asp | Ala | Glu | Ile | Val | Val | |
| | | | 165 | | | | | 170 | | | | | 175 | | | |

| aag | gac | aat | ggc | aga | agc | tgt | ccc | ccc | tgt | cat | gag | gtt | tgc | aag | ggg | 576 |
|---|---|---|---|---|---|---|---|---|---|---|---|---|---|---|---|---|
| Lys | Asp | Asn | Gly | Arg | Ser | Cys | Pro | Pro | Cys | His | Glu | Val | Cys | Lys | Gly | |
| | | 180 | | | | | 185 | | | | | 190 | | | | |

| cga | tgc | tgg | ggt | cct | gga | tca | gaa | gac | tgc | cag | aca | ttg | acc | aag | acc | 624 |
|---|---|---|---|---|---|---|---|---|---|---|---|---|---|---|---|---|
| Arg | Cys | Trp | Gly | Pro | Gly | Ser | Glu | Asp | Cys | Gln | Thr | Leu | Thr | Lys | Thr | |
| | 195 | | | | | 200 | | | | | 205 | | | | | |

| atc | tgt | gct | cct | cag | tgt | aat | ggt | cac | tgc | ttt | ggg | ccc | aac | ccc | aac | 672 |
|---|---|---|---|---|---|---|---|---|---|---|---|---|---|---|---|---|
| Ile | Cys | Ala | Pro | Gln | Cys | Asn | Gly | His | Cys | Phe | Gly | Pro | Asn | Pro | Asn | |
| 210 | | | | | 215 | | | | | 220 | | | | | | |

| cag | tgc | tgc | cat | gat | gag | tgt | gcc | ggg | ggc | tgc | tca | ggc | cct | cag | gac | 720 |
|---|---|---|---|---|---|---|---|---|---|---|---|---|---|---|---|---|
| Gln | Cys | Cys | His | Asp | Glu | Cys | Ala | Gly | Gly | Cys | Ser | Gly | Pro | Gln | Asp | |
| 225 | | | | | 230 | | | | | 235 | | | | | 240 | |

| aca | gac | tgc | ttt | gcc | tgc | cgg | cac | ttc | aat | gac | agt | gga | gcc | tgt | gta | 768 |
|---|---|---|---|---|---|---|---|---|---|---|---|---|---|---|---|---|
| Thr | Asp | Cys | Phe | Ala | Cys | Arg | His | Phe | Asn | Asp | Ser | Gly | Ala | Cys | Val | |
| | | | 245 | | | | | 250 | | | | | 255 | | | |

```
                                              -continued cct cgc tgt cca cag cct ctt gtc tac aac aag cta act ttc cag ctg       816
Pro Arg Cys Pro Gln Pro Leu Val Tyr Asn Lys Leu Thr Phe Gln Leu
        260                 265                 270 gaa ccc aat ccc cac acc aag tat cag tat gga gga gtt tgt gta gcc       864
Glu Pro Asn Pro His Thr Lys Tyr Gln Tyr Gly Gly Val Cys Val Ala
    275                 280                 285 agc tgt ccc cat aac ttt gtg gtg gat caa aca tcc tgt gtc agg gcc       912
Ser Cys Pro His Asn Phe Val Val Asp Gln Thr Ser Cys Val Arg Ala
290                 295                 300 tgt cct cct gac aag atg gaa gta gat aaa aat ggg ctc aag atg tgt       960
Cys Pro Pro Asp Lys Met Glu Val Asp Lys Asn Gly Leu Lys Met Cys
305                 310                 315                 320 gag cct tgt ggg gga cta tgt ccc aaa gcc tgt gag gga aca ggc tct      1008
Glu Pro Cys Gly Gly Leu Cys Pro Lys Ala Cys Glu Gly Thr Gly Ser
                325                 330                 335 ggg agc cgc ttc cag act gtg gac tcg agc aac att gat gga ttt gtg      1056
Gly Ser Arg Phe Gln Thr Val Asp Ser Ser Asn Ile Asp Gly Phe Val
            340                 345                 350 aac tgc acc aag atc ctg ggc aac ctg gac ttt ctg atc acc ggc ctc      1104
Asn Cys Thr Lys Ile Leu Gly Asn Leu Asp Phe Leu Ile Thr Gly Leu
        355                 360                 365 aat gga gac ccc tgg cac aag atc cct gcc ctg gac cca gag aag ctc      1152
Asn Gly Asp Pro Trp His Lys Ile Pro Ala Leu Asp Pro Glu Lys Leu
    370                 375                 380 aat gtc ttc cgg aca gta cgg gag atc aca ggt tac ctg aac atc cag      1200
Asn Val Phe Arg Thr Val Arg Glu Ile Thr Gly Tyr Leu Asn Ile Gln
385                 390                 395                 400 tcc tgg ccg ccc cac atg cac aac ttc agt gtt ttt tcc aat ttg aca      1248
Ser Trp Pro Pro His Met His Asn Phe Ser Val Phe Ser Asn Leu Thr
                405                 410                 415 acc att gga ggc aga agc ctc tac aac cgg ggc ttc tca ttg ttg atc      1296
Thr Ile Gly Gly Arg Ser Leu Tyr Asn Arg Gly Phe Ser Leu Leu Ile
            420                 425                 430 atg aag aac ttg aat gtc aca tct ctg ggc ttc cga tcc ctg aag gaa      1344
Met Lys Asn Leu Asn Val Thr Ser Leu Gly Phe Arg Ser Leu Lys Glu
        435                 440                 445 att agt gct ggg cgt atc tat ata agt gcc aat agg cag ctc tgc tac      1392
Ile Ser Ala Gly Arg Ile Tyr Ile Ser Ala Asn Arg Gln Leu Cys Tyr
    450                 455                 460 cac cac tct ttg aac tgg acc aag gtg ctt cgg ggg cct acg gaa gag      1440
His His Ser Leu Asn Trp Thr Lys Val Leu Arg Gly Pro Thr Glu Glu
465                 470                 475                 480 cga cta gac atc aag cat aat cgg ccg cgc aga gac tgc gtg gca gag      1488
Arg Leu Asp Ile Lys His Asn Arg Pro Arg Arg Asp Cys Val Ala Glu
                485                 490                 495 ggc aaa gtg tgt gac cca ctg tgc tcc tct ggg gga tgc tgg ggc cca      1536
Gly Lys Val Cys Asp Pro Leu Cys Ser Ser Gly Gly Cys Trp Gly Pro
            500                 505                 510 ggc cct ggt cag tgc ttg tcc tgt cga aat tat agc cga gga ggt gtc      1584
Gly Pro Gly Gln Cys Leu Ser Cys Arg Asn Tyr Ser Arg Gly Gly Val
        515                 520                 525 tgt gtg acc cac tgc aac ttt ctg aat ggg gag cct cga gaa ttt gcc      1632
Cys Val Thr His Cys Asn Phe Leu Asn Gly Glu Pro Arg Glu Phe Ala
    530                 535                 540 cat gag gcc gaa tgc ttc tcc tgc cac ccg gaa tgc caa ccc atg ggg      1680
His Glu Ala Glu Cys Phe Ser Cys His Pro Glu Cys Gln Pro Met Gly
545                 550                 555                 560 ggc act gcc aca tgc aat ggc tcg ggc tct gat act tgt gct caa tgt      1728
Gly Thr Ala Thr Cys Asn Gly Ser Gly Ser Asp Thr Cys Ala Gln Cys
                565                 570                 575
```

```
gcc cat ttt cga gat ggg ccc cac tgt gtg agc agc tgc ccc cat gga    1776
Ala His Phe Arg Asp Gly Pro His Cys Val Ser Ser Cys Pro His Gly
        580                 585                 590 gtc cta ggt gcc aag ggc cca atc tac aag tac cca gat gtt cag aat    1824
Val Leu Gly Ala Lys Gly Pro Ile Tyr Lys Tyr Pro Asp Val Gln Asn
    595                 600                 605 gaa tgt cgg ccc tgc cat gag aac tgc acc cag ggg tgt aaa gga cca    1872
Glu Cys Arg Pro Cys His Glu Asn Cys Thr Gln Gly Cys Lys Gly Pro
610                 615                 620 gag ctt caa gac tgt tta gga caa aca ctg gtg ctg atc ggc aaa acc    1920
Glu Leu Gln Asp Cys Leu Gly Gln Thr Leu Val Leu Ile Gly Lys Thr
625                 630                 635                 640 cat ctg aca atg gct ttg aca gtg ata gca gga ttg gta gtg att ttc    1968
His Leu Thr Met Ala Leu Thr Val Ile Ala Gly Leu Val Val Ile Phe
                645                 650                 655 atg atg ctg ggc ggc act ttt ctc tac tgg cgt ggg cgc cgg att cag    2016
Met Met Leu Gly Gly Thr Phe Leu Tyr Trp Arg Gly Arg Arg Ile Gln
                660                 665                 670 aat aaa agg gct atg agg cga tac ttg gaa cgg ggt gag agc ata gag    2064
Asn Lys Arg Ala Met Arg Arg Tyr Leu Glu Arg Gly Glu Ser Ile Glu
            675                 680                 685 cct ctg gac ccc agt gag aag gct aac aaa gtc ttg gcc aga atc ttc    2112
Pro Leu Asp Pro Ser Glu Lys Ala Asn Lys Val Leu Ala Arg Ile Phe
690                 695                 700 aaa gag aca gag cta agg aag ctt aaa gtg ctt ggc tcg ggt gtc ttt    2160
Lys Glu Thr Glu Leu Arg Lys Leu Lys Val Leu Gly Ser Gly Val Phe
705                 710                 715                 720 gga act gtg cac aaa gga gtg tgg atc cct gag ggt gaa tca atc aag    2208
Gly Thr Val His Lys Gly Val Trp Ile Pro Glu Gly Glu Ser Ile Lys
                725                 730                 735 att cca gtc tgc att aaa gtc att gag gac aag agt gga cgg cag agt    2256
Ile Pro Val Cys Ile Lys Val Ile Glu Asp Lys Ser Gly Arg Gln Ser
                740                 745                 750 ttt caa gct gtg aca gat cat atg ctg gcc att ggc agc ctg gac cat    2304
Phe Gln Ala Val Thr Asp His Met Leu Ala Ile Gly Ser Leu Asp His
            755                 760                 765 gcc cac att gta agg ctg ctg gga cta tgc cca ggg tca tct ctg cag    2352
Ala His Ile Val Arg Leu Leu Gly Leu Cys Pro Gly Ser Ser Leu Gln
770                 775                 780 ctt gtc act caa tat ttg cct ctg ggt tct ctg ctg gat cat gtg aga    2400
Leu Val Thr Gln Tyr Leu Pro Leu Gly Ser Leu Leu Asp His Val Arg
785                 790                 795                 800 caa cac cgg ggg gca ctg ggg cca cag ctg ctc aac tgg gga gta        2448
Gln His Arg Gly Ala Leu Gly Pro Gln Leu Leu Asn Trp Gly Val
                805                 810                 815 caa att gcc aag gga atg tac tac ctt gag gaa cat ggt atg gtg cat    2496
Gln Ile Ala Lys Gly Met Tyr Tyr Leu Glu Glu His Gly Met Val His
            820                 825                 830 aga aac ctg gct gcc cga aac gtg cta ctc aag tca ccc agt cag gtt    2544
Arg Asn Leu Ala Ala Arg Asn Val Leu Leu Lys Ser Pro Ser Gln Val
835                 840                 845 cag gtg gca gat ttt ggt gtg gct gac ctg ctg cct cct gat gat aag    2592
Gln Val Ala Asp Phe Gly Val Ala Asp Leu Leu Pro Pro Asp Asp Lys
850                 855                 860 cag ctg cta tac agt gag gcc aag act cca att aag tgg atg gcc ctt    2640
Gln Leu Leu Tyr Ser Glu Ala Lys Thr Pro Ile Lys Trp Met Ala Leu
865                 870                 875                 880 gag agt atc cac ttt ggg aaa tac aca cac cag agt gat gtc tgg agc    2688
Glu Ser Ile His Phe Gly Lys Tyr Thr His Gln Ser Asp Val Trp Ser
```

|  |  |
|---|---|
| ```
                    885                 890                 895
tat ggt gtg aca gtt tgg gag ttg atg acc ttc ggg gca gag ccc tat
Tyr Gly Val Thr Val Trp Glu Leu Met Thr Phe Gly Ala Glu Pro Tyr
            900                 905                 910 gca ggg cta cga ttg gct gaa gta cca gac ctg cta gag aag ggg gag
Ala Gly Leu Arg Leu Ala Glu Val Pro Asp Leu Leu Glu Lys Gly Glu
        915                 920                 925 cgg ttg gca cag ccc cag atc tgc aca att gat gtc tac atg gtg atg
Arg Leu Ala Gln Pro Gln Ile Cys Thr Ile Asp Val Tyr Met Val Met
    930                 935                 940 gtc aag tgt tgg atg att gat gag aac att cgc cca acc ttt aaa gaa
Val Lys Cys Trp Met Ile Asp Glu Asn Ile Arg Pro Thr Phe Lys Glu
945                 950                 955                 960 cta gcc aat gag ttc acc agg atg gcc cga gac cca cca cgg tat ctg
Leu Ala Asn Glu Phe Thr Arg Met Ala Arg Asp Pro Pro Arg Tyr Leu
                965                 970                 975 gtc ata aag aga gag agt ggg cct gga ata gcc cct ggg cca gag ccc
Val Ile Lys Arg Glu Ser Gly Pro Gly Ile Ala Pro Gly Pro Glu Pro
            980                 985                 990 cat ggt ctg aca aac aag aag cta gag gaa gta gag ctg gag cca gaa
His Gly Leu Thr Asn Lys Lys Leu Glu Glu Val Glu Leu Glu Pro Glu
        995                 1000                1005 cta gac cta gac cta gac ttg gaa gca gag gag gac aac ctg gca acc
Leu Asp Leu Asp Leu Asp Leu Glu Ala Glu Glu Asp Asn Leu Ala Thr
    1010                1015                1020 acc aca ctg ggc tcc gcc ctc agc cta cca gtt gga aca ctt aat cgg
Thr Thr Leu Gly Ser Ala Leu Ser Leu Pro Val Gly Thr Leu Asn Arg
1025                1030                1035                1040 cca cgt ggg agc cag agc ctt tta agt cca tca tct gga tac atg ccc
Pro Arg Gly Ser Gln Ser Leu Leu Ser Pro Ser Ser Gly Tyr Met Pro
                1045                1050                1055 atg aac cag ggt aat ctt ggg ggg tct tgc cag gag tct gca gtt tct
Met Asn Gln Gly Asn Leu Gly Gly Ser Cys Gln Glu Ser Ala Val Ser
            1060                1065                1070 ggg agc agt gaa cgg tgc ccc cgt cca gtc tct cta cac cca atg cca
Gly Ser Ser Glu Arg Cys Pro Arg Pro Val Ser Leu His Pro Met Pro
        1075                1080                1085 cgg gga tgc ctg gca tca gag tca tca gag ggg cat gta aca ggc tct
Arg Gly Cys Leu Ala Ser Glu Ser Ser Glu Gly His Val Thr Gly Ser
    1090                1095                1100 gag gct gag ctc cag gag aaa gtg tca atg tgt aga agc cgg agc agg
Glu Ala Glu Leu Gln Glu Lys Val Ser Met Cys Arg Ser Arg Ser Arg
1105                1110                1115                1120 agc cgg agc cca cgg cca cgc gga gat agc gcc tac cat tcc cag cgc
Ser Arg Ser Pro Arg Pro Arg Gly Asp Ser Ala Tyr His Ser Gln Arg
                1125                1130                1135 cac agt ctg ctg act cct gtt acc cca ctc tcc cca ccc ggg tta gag
His Ser Leu Leu Thr Pro Val Thr Pro Leu Ser Pro Pro Gly Leu Glu
            1140                1145                1150 gaa gag gat gtc aac ggt tat gtc atg cca gat aca cac ctc aaa ggt
Glu Glu Asp Val Asn Gly Tyr Val Met Pro Asp Thr His Leu Lys Gly
        1155                1160                1165 act ccc tcc tcc cgg gaa ggc acc ctt tct tca gtg ggt ctc agt tct
Thr Pro Ser Ser Arg Glu Gly Thr Leu Ser Ser Val Gly Leu Ser Ser
    1170                1175                1180 gtc ctg ggt act gaa gaa gaa gat gaa gat gag gag tat gaa tac atg
Val Leu Gly Thr Glu Glu Glu Asp Glu Asp Glu Glu Tyr Glu Tyr Met
1185                1190                1195                1200 aac cgg agg aga agg cac agt cca cct cat ccc cct agg cca agt tcc
``` | 2736<br><br>2784<br><br>2832<br><br>2880<br><br>2928<br><br>2976<br><br>3024<br><br>3072<br><br>3120<br><br>3168<br><br>3216<br><br>3264<br><br>3312<br><br>3360<br><br>3408<br><br>3456<br><br>3504<br><br>3552<br><br>3600<br><br>3648 |

```
                                                          -continued

Asn Arg Arg Arg Arg His Ser Pro Pro His Pro Arg Pro Ser Ser
                1205                1210                1215 ctt gag gag ctg ggt tat gag tac atg gat gtg ggg tca gac ctc agt     3696
Leu Glu Glu Leu Gly Tyr Glu Tyr Met Asp Val Gly Ser Asp Leu Ser
            1220                1225                1230 gcc tct ctg ggc agc aca cag agt tgc cca ctc cac cct gta ccc atc    3744
Ala Ser Leu Gly Ser Thr Gln Ser Cys Pro Leu His Pro Val Pro Ile
        1235                1240                1245 atg ccc act gca ggc aca act cca gat gaa gac tat gaa tat atg aat    3792
Met Pro Thr Ala Gly Thr Thr Pro Asp Glu Asp Tyr Glu Tyr Met Asn
    1250                1255                1260 cgg caa cga gat gga ggt ggt cct ggg ggt gat tat gca gcc atg ggg    3840
Arg Gln Arg Asp Gly Gly Gly Pro Gly Gly Asp Tyr Ala Ala Met Gly
1265                1270                1275                1280 gcc tgc cca gca tct gag caa ggg tat gaa gag atg aga gct ttt cag    3888
Ala Cys Pro Ala Ser Glu Gln Gly Tyr Glu Glu Met Arg Ala Phe Gln
                1285                1290                1295 ggg cct gga cat cag gcc ccc cat gtc cat tat gcc cgc cta aaa act    3936
Gly Pro Gly His Gln Ala Pro His Val His Tyr Ala Arg Leu Lys Thr
            1300                1305                1310 cta cgt agc tta gag gct aca gac tct gcc ttt gat aac cct gat tac    3984
Leu Arg Ser Leu Glu Ala Thr Asp Ser Ala Phe Asp Asn Pro Asp Tyr
        1315                1320                1325 tgg cat agc agg ctt ttc ccc aag gct aat gcc cag aga acg            4026
Trp His Ser Arg Leu Phe Pro Lys Ala Asn Ala Gln Arg Thr
    1330                1335                1340

<210> SEQ ID NO 2
<211> LENGTH: 1342
<212> TYPE: PRT
<213> ORGANISM: Homo sapiens

<400> SEQUENCE: 2

Met Arg Ala Asn Asp Ala Leu Gln Val Leu Gly Leu Leu Phe Ser Leu
 1               5                  10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190
```

```
Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
        210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
            245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
        290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
            355                 360                 365

Asn Gly Asp Pro Trp His Lys Ile Pro Ala Leu Asp Pro Glu Lys Leu
        370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
        435                 440                 445

Ile Ser Ala Gly Arg Ile Tyr Ile Ser Ala Asn Arg Gln Leu Cys Tyr
450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                485                 490                 495

Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Gly Gly Val
            515                 520                 525

Cys Val Thr His Cys Asn Phe Leu Asn Gly Glu Pro Arg Glu Phe Ala
530                 535                 540

His Glu Ala Glu Cys Phe Ser Cys His Pro Glu Cys Gln Pro Met Gly
545                 550                 555                 560

Gly Thr Ala Thr Cys Asn Gly Ser Gly Ser Asp Thr Cys Ala Gln Cys
                565                 570                 575

Ala His Phe Arg Asp Gly Pro His Cys Val Ser Ser Cys Pro His Gly
            580                 585                 590

Val Leu Gly Ala Lys Gly Pro Ile Tyr Lys Tyr Pro Asp Val Gln Asn
        595                 600                 605

Glu Cys Arg Pro Cys His Glu Asn Cys Thr Gln Gly Cys Lys Gly Pro
```

-continued

```
            610                 615                 620
Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                645                 650                 655

Met Met Leu Gly Gly Thr Phe Leu Tyr Trp Arg Gly Arg Arg Ile Gln
            660                 665                 670

Asn Lys Arg Ala Met Arg Arg Tyr Leu Glu Arg Gly Glu Ser Ile Glu
        675                 680                 685

Pro Leu Asp Pro Ser Glu Lys Ala Asn Lys Val Leu Ala Arg Ile Phe
    690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
        755                 760                 765

Ala His Ile Val Arg Leu Leu Gly Leu Cys Pro Gly Ser Ser Leu Gln
    770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
                805                 810                 815

Gln Ile Ala Lys Gly Met Tyr Tyr Leu Glu Glu His Gly Met Val His
            820                 825                 830

Arg Asn Leu Ala Ala Arg Asn Val Leu Leu Lys Ser Pro Ser Gln Val
        835                 840                 845

Gln Val Ala Asp Phe Gly Val Ala Asp Leu Leu Pro Pro Asp Asp Lys
    850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
            900                 905                 910

Ala Gly Leu Arg Leu Ala Glu Val Pro Asp Leu Leu Glu Lys Gly Glu
        915                 920                 925

Arg Leu Ala Gln Pro Gln Ile Cys Thr Ile Asp Val Tyr Met Val Met
    930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
                965                 970                 975

Val Ile Lys Arg Glu Ser Gly Pro Gly Ile Ala Pro Gly Pro Glu Pro
            980                 985                 990

His Gly Leu Thr Asn Lys Lys Leu Glu Glu Val Glu Leu Glu Pro Glu
        995                 1000                1005

Leu Asp Leu Asp Leu Asp Leu Glu Ala Glu Glu Asp Asn Leu Ala Thr
    1010                1015                1020

Thr Thr Leu Gly Ser Ala Leu Ser Leu Pro Val Gly Thr Leu Asn Arg
1025                1030                1035                1040
```

-continued

Pro Arg Gly Ser Gln Ser Leu Leu Ser Pro Ser Ser Gly Tyr Met Pro
         1045                1050                1055

Met Asn Gln Gly Asn Leu Gly Gly Ser Cys Gln Glu Ser Ala Val Ser
         1060                1065                1070

Gly Ser Ser Glu Arg Cys Pro Arg Pro Val Ser Leu His Pro Met Pro
         1075                1080                1085

Arg Gly Cys Leu Ala Ser Glu Ser Ser Glu Gly His Val Thr Gly Ser
         1090                1095                1100

Glu Ala Glu Leu Gln Glu Lys Val Ser Met Cys Arg Ser Arg Ser Arg
1105                1110                1115                1120

Ser Arg Ser Pro Arg Pro Arg Gly Asp Ser Ala Tyr His Ser Gln Arg
         1125                1130                1135

His Ser Leu Leu Thr Pro Val Thr Pro Leu Ser Pro Gly Leu Glu
         1140                1145                1150

Glu Glu Asp Val Asn Gly Tyr Val Met Pro Asp Thr His Leu Lys Gly
         1155                1160                1165

Thr Pro Ser Ser Arg Glu Gly Thr Leu Ser Ser Val Gly Leu Ser Ser
         1170                1175                1180

Val Leu Gly Thr Glu Glu Glu Asp Glu Asp Glu Glu Tyr Glu Tyr Met
1185                1190                1195                1200

Asn Arg Arg Arg Arg His Ser Pro Pro His Pro Pro Arg Pro Ser Ser
         1205                1210                1215

Leu Glu Glu Leu Gly Tyr Glu Tyr Met Asp Val Gly Ser Asp Leu Ser
         1220                1225                1230

Ala Ser Leu Gly Ser Thr Gln Ser Cys Pro Leu His Pro Val Pro Ile
         1235                1240                1245

Met Pro Thr Ala Gly Thr Thr Pro Asp Glu Asp Tyr Glu Tyr Met Asn
         1250                1255                1260

Arg Gln Arg Asp Gly Gly Gly Pro Gly Gly Asp Tyr Ala Ala Met Gly
1265                1270                1275                1280

Ala Cys Pro Ala Ser Glu Gln Gly Tyr Glu Glu Met Arg Ala Phe Gln
         1285                1290                1295

Gly Pro Gly His Gln Ala Pro His Val His Tyr Ala Arg Leu Lys Thr
         1300                1305                1310

Leu Arg Ser Leu Glu Ala Thr Asp Ser Ala Phe Asp Asn Pro Asp Tyr
         1315                1320                1325

Trp His Ser Arg Leu Phe Pro Lys Ala Asn Ala Gln Arg Thr
         1330                1335                1340

<210> SEQ ID NO 3
<211> LENGTH: 1935
<212> TYPE: DNA
<213> ORGANISM: Homo sapiens
<220> FEATURE:
<221> NAME/KEY: CDS
<222> LOCATION: (1)...(1935)

<400> SEQUENCE: 3

```
atg tcc gag cgc aaa gaa ggc aga ggc aaa ggg aag ggc aag aag aag       48
Met Ser Glu Arg Lys Glu Gly Arg Gly Lys Gly Lys Gly Lys Lys Lys
 1               5                  10                  15 gag cga ggc tcc ggc aag aag ccg gag tcc gcg gcg ggc agc cag agc       96
Glu Arg Gly Ser Gly Lys Lys Pro Glu Ser Ala Ala Gly Ser Gln Ser
             20                  25                  30 cca gcc ttg cct ccc caa ttg aaa gag atg aaa agc cag gaa tcg gct      144
Pro Ala Leu Pro Pro Gln Leu Lys Glu Met Lys Ser Gln Glu Ser Ala
```

-continued

```
                35                   40                   45
gca ggt tcc aaa cta gtc ctt cgg tgt gaa acc agt tct gaa tac tcc      192
Ala Gly Ser Lys Leu Val Leu Arg Cys Glu Thr Ser Ser Glu Tyr Ser
 50                   55                   60 tct ctc aga ttc aag tgg ttc aag aat ggg aat gaa ttg aat cga aaa      240
Ser Leu Arg Phe Lys Trp Phe Lys Asn Gly Asn Glu Leu Asn Arg Lys
 65                   70                   75                   80 aac aaa cca caa aat atc aag ata caa aaa aag cca ggg aag tca gaa      288
Asn Lys Pro Gln Asn Ile Lys Ile Gln Lys Lys Pro Gly Lys Ser Glu
                 85                   90                   95 ctt cgc att aac aaa gca tca ctg gct gat tct gga gag tat atg tgc      336
Leu Arg Ile Asn Lys Ala Ser Leu Ala Asp Ser Gly Glu Tyr Met Cys
             100                  105                  110 aaa gtg atc agc aaa tta gga aat gac agt gcc tct gcc aat atc acc      384
Lys Val Ile Ser Lys Leu Gly Asn Asp Ser Ala Ser Ala Asn Ile Thr
         115                  120                  125 atc gtg gaa tca aac gag atc atc act ggt atg cca gcc tca act gaa      432
Ile Val Glu Ser Asn Glu Ile Ile Thr Gly Met Pro Ala Ser Thr Glu
     130                  135                  140 gga gca tat gtg tct tca gag tct ccc att aga ata tca gta tcc aca      480
Gly Ala Tyr Val Ser Ser Glu Ser Pro Ile Arg Ile Ser Val Ser Thr
145                  150                  155                  160 gaa gga gca aat act tct tca tct aca tct aca tcc acc act ggg aca      528
Glu Gly Ala Asn Thr Ser Ser Ser Thr Ser Thr Ser Thr Thr Gly Thr
                 165                  170                  175 agc cat ctt gta aaa tgt gcg gag aag gag aaa act ttc tgt gtg aat      576
Ser His Leu Val Lys Cys Ala Glu Lys Glu Lys Thr Phe Cys Val Asn
             180                  185                  190 gga ggg gag tgc ttc atg gtg aaa gac ctt tca aac ccc tcg aga tac      624
Gly Gly Glu Cys Phe Met Val Lys Asp Leu Ser Asn Pro Ser Arg Tyr
         195                  200                  205 ttg tgc aag tgc cca aat gag ttt act ggt gat cgc tgc caa aac tac      672
Leu Cys Lys Cys Pro Asn Glu Phe Thr Gly Asp Arg Cys Gln Asn Tyr
     210                  215                  220 gta atg gcc agc ttc tac aag cat ctt ggg att gaa ttt atg gag gcg      720
Val Met Ala Ser Phe Tyr Lys His Leu Gly Ile Glu Phe Met Glu Ala
225                  230                  235                  240 gag gag ctg tac cag aag aga gtg ctg acc ata acc ggc atc tgc atc      768
Glu Glu Leu Tyr Gln Lys Arg Val Leu Thr Ile Thr Gly Ile Cys Ile
                 245                  250                  255 gcc ctc ctt gtg gtc ggc atc atg tgt gtg gtg gcc tac tgc aaa acc      816
Ala Leu Leu Val Val Gly Ile Met Cys Val Val Ala Tyr Cys Lys Thr
             260                  265                  270 aag aaa cag cgg aaa aag ctg cat gac cgt ctt cgg cag agc ctt cgg      864
Lys Lys Gln Arg Lys Lys Leu His Asp Arg Leu Arg Gln Ser Leu Arg
         275                  280                  285 tct gaa cga aac aat atg atg aac att gcc aat ggg cct cac cat cct      912
Ser Glu Arg Asn Asn Met Met Asn Ile Ala Asn Gly Pro His His Pro
     290                  295                  300 aac cca ccc ccc gag aat gtc cag ctg gtg aat caa tac gta tct aaa      960
Asn Pro Pro Pro Glu Asn Val Gln Leu Val Asn Gln Tyr Val Ser Lys
305                  310                  315                  320 aac gtc atc tcc agt gag cat att gtt gag aga gaa gca gag aca tcc     1008
Asn Val Ile Ser Ser Glu His Ile Val Glu Arg Glu Ala Glu Thr Ser
                 325                  330                  335 ttt tcc acc agt cac tat act tcc aca gcc cat cac tcc act act gtc     1056
Phe Ser Thr Ser His Tyr Thr Ser Thr Ala His His Ser Thr Thr Val
             340                  345                  350 acc cag act cct agc cac agc tgg agc aac gga cac act gaa agc atc     1104
```

```
                Thr Gln Thr Pro Ser His Ser Trp Ser Asn Gly His Thr Glu Ser Ile
                            355                 360                 365 ctt tcc gaa agc cac tct gta atc gtg atg tca tcc gta gaa aac agt              1152
Leu Ser Glu Ser His Ser Val Ile Val Met Ser Ser Val Glu Asn Ser
370                 375                 380 agg cac agc agc cca act ggg ggc cca aga gga cgt ctt aat ggc aca              1200
Arg His Ser Ser Pro Thr Gly Gly Pro Arg Gly Arg Leu Asn Gly Thr
385                 390                 395                 400 gga ggc cct cgt gaa tgt aac agc ttc ctc agg cat gcc aga gaa acc              1248
Gly Gly Pro Arg Glu Cys Asn Ser Phe Leu Arg His Ala Arg Glu Thr
                405                 410                 415 cct gat tcc tac cga gac tct cct cat agt gaa agg tat gtg tca gcc              1296
Pro Asp Ser Tyr Arg Asp Ser Pro His Ser Glu Arg Tyr Val Ser Ala
            420                 425                 430 atg acc acc ccg gct cgt atg tca cct gta gat ttc cac acg cca agc              1344
Met Thr Thr Pro Ala Arg Met Ser Pro Val Asp Phe His Thr Pro Ser
        435                 440                 445 tcc ccc aaa tcg ccc cct tcg gaa atg tct cca ccc gtg tcc agc atg              1392
Ser Pro Lys Ser Pro Pro Ser Glu Met Ser Pro Pro Val Ser Ser Met
    450                 455                 460 acg gtg tcc atg cct tcc atg gcg gtc agc ccc ttc atg gaa gaa gag              1440
Thr Val Ser Met Pro Ser Met Ala Val Ser Pro Phe Met Glu Glu Glu
465                 470                 475                 480 aga cct cta ctt ctc gtg aca cca cca agg ctg cgg gag aag aag ttt              1488
Arg Pro Leu Leu Leu Val Thr Pro Pro Arg Leu Arg Glu Lys Lys Phe
                485                 490                 495 gac cat cac cct cag cag ttc agc tcc ttc cac cac aac ccc gcg cat              1536
Asp His His Pro Gln Gln Phe Ser Ser Phe His His Asn Pro Ala His
            500                 505                 510 gac agt aac agc ctc cct gct agc ccc ttg agg ata gtg gag gat gag              1584
Asp Ser Asn Ser Leu Pro Ala Ser Pro Leu Arg Ile Val Glu Asp Glu
        515                 520                 525 gag tat gaa acg acc caa gag tac gag cca gcc caa gag cct gtt aag              1632
Glu Tyr Glu Thr Thr Gln Glu Tyr Glu Pro Ala Gln Glu Pro Val Lys
    530                 535                 540 aaa ctc gcc aat agc cgg cgg gcc aaa aga acc aag ccc aat ggc cac              1680
Lys Leu Ala Asn Ser Arg Arg Ala Lys Arg Thr Lys Pro Asn Gly His
545                 550                 555                 560 att gct aac aga ttg gaa gtg gac agc aac aca agc tcc cag agc agt              1728
Ile Ala Asn Arg Leu Glu Val Asp Ser Asn Thr Ser Ser Gln Ser Ser
                565                 570                 575 aac tca gag agt gaa aca gaa gat gaa aga gta ggt gaa gat acg cct              1776
Asn Ser Glu Ser Glu Thr Glu Asp Glu Arg Val Gly Glu Asp Thr Pro
            580                 585                 590 ttc ctg ggc ata cag aac ccc ctg gca gcc agt ctt gag gca aca cct              1824
Phe Leu Gly Ile Gln Asn Pro Leu Ala Ala Ser Leu Glu Ala Thr Pro
        595                 600                 605 gcc ttc cgc ctg gct gac agc agg act aac cca gca ggc cgc ttc tcg              1872
Ala Phe Arg Leu Ala Asp Ser Arg Thr Asn Pro Ala Gly Arg Phe Ser
    610                 615                 620 aca cag gaa gaa atc cag gcc agg ctg tct agt gta att gct aac caa              1920
Thr Gln Glu Glu Ile Gln Ala Arg Leu Ser Ser Val Ile Ala Asn Gln
625                 630                 635                 640 gac cct att gct gta                                                          1935
Asp Pro Ile Ala Val
                645

<210> SEQ ID NO 4
<211> LENGTH: 645
<212> TYPE: PRT
```

<213> ORGANISM: Homo sapiens

<400> SEQUENCE: 4

```
Met Ser Glu Arg Lys Glu Gly Arg Gly Lys Gly Lys Gly Lys Lys Lys
  1               5                  10                  15
Glu Arg Gly Ser Gly Lys Lys Pro Glu Ser Ala Ala Gly Ser Gln Ser
             20                  25                  30
Pro Ala Leu Pro Pro Gln Leu Lys Glu Met Lys Ser Gln Glu Ser Ala
         35                  40                  45
Ala Gly Ser Lys Leu Val Leu Arg Cys Glu Thr Ser Ser Glu Tyr Ser
 50                  55                  60
Ser Leu Arg Phe Lys Trp Phe Lys Asn Gly Asn Glu Leu Asn Arg Lys
 65                  70                  75                  80
Asn Lys Pro Gln Asn Ile Lys Ile Gln Lys Lys Pro Gly Lys Ser Glu
                 85                  90                  95
Leu Arg Ile Asn Lys Ala Ser Leu Ala Asp Ser Gly Glu Tyr Met Cys
            100                 105                 110
Lys Val Ile Ser Lys Leu Gly Asn Asp Ser Ala Ser Ala Asn Ile Thr
        115                 120                 125
Ile Val Glu Ser Asn Glu Ile Ile Thr Gly Met Pro Ala Ser Thr Glu
130                 135                 140
Gly Ala Tyr Val Ser Ser Glu Ser Pro Ile Arg Ile Ser Val Ser Thr
145                 150                 155                 160
Glu Gly Ala Asn Thr Ser Ser Ser Thr Ser Thr Ser Thr Thr Gly Thr
                165                 170                 175
Ser His Leu Val Lys Cys Ala Glu Lys Glu Lys Thr Phe Cys Val Asn
            180                 185                 190
Gly Gly Glu Cys Phe Met Val Lys Asp Leu Ser Asn Pro Ser Arg Tyr
        195                 200                 205
Leu Cys Lys Cys Pro Asn Glu Phe Thr Gly Asp Arg Cys Gln Asn Tyr
    210                 215                 220
Val Met Ala Ser Phe Tyr Lys His Leu Gly Ile Glu Phe Met Glu Ala
225                 230                 235                 240
Glu Glu Leu Tyr Gln Lys Arg Val Leu Thr Ile Thr Gly Ile Cys Ile
                245                 250                 255
Ala Leu Leu Val Val Gly Ile Met Cys Val Val Ala Tyr Cys Lys Thr
            260                 265                 270
Lys Lys Gln Arg Lys Lys Leu His Asp Arg Leu Arg Gln Ser Leu Arg
        275                 280                 285
Ser Glu Arg Asn Asn Met Met Asn Ile Ala Asn Gly Pro His His Pro
290                 295                 300
Asn Pro Pro Pro Glu Asn Val Gln Leu Val Asn Gln Tyr Val Ser Lys
305                 310                 315                 320
Asn Val Ile Ser Ser Glu His Ile Val Glu Arg Glu Ala Glu Thr Ser
                325                 330                 335
Phe Ser Thr Ser His Tyr Thr Ser Thr Ala His His Ser Thr Thr Val
            340                 345                 350
Thr Gln Thr Pro Ser His Ser Trp Ser Asn Gly His Thr Glu Ser Ile
        355                 360                 365
Leu Ser Glu Ser His Ser Val Ile Val Met Ser Ser Val Glu Asn Ser
    370                 375                 380
Arg His Ser Ser Pro Thr Gly Gly Pro Arg Gly Arg Leu Asn Gly Thr
385                 390                 395                 400
```

-continued

```
Gly Gly Pro Arg Glu Cys Asn Ser Phe Leu Arg His Ala Arg Glu Thr
            405                 410                 415

Pro Asp Ser Tyr Arg Asp Ser Pro His Ser Glu Arg Tyr Val Ser Ala
        420                 425                 430

Met Thr Thr Pro Ala Arg Met Ser Pro Val Asp Phe His Thr Pro Ser
            435                 440                 445

Ser Pro Lys Ser Pro Pro Ser Glu Met Ser Pro Val Ser Ser Met
    450                 455                 460

Thr Val Ser Met Pro Ser Met Ala Val Ser Pro Phe Met Glu Glu Glu
465                 470                 475                 480

Arg Pro Leu Leu Leu Val Thr Pro Pro Arg Leu Arg Glu Lys Lys Phe
                485                 490                 495

Asp His His Pro Gln Gln Phe Ser Ser Phe His His Asn Pro Ala His
            500                 505                 510

Asp Ser Asn Ser Leu Pro Ala Ser Pro Leu Arg Ile Val Glu Asp Glu
        515                 520                 525

Glu Tyr Glu Thr Thr Gln Glu Tyr Glu Pro Ala Gln Glu Pro Val Lys
    530                 535                 540

Lys Leu Ala Asn Ser Arg Arg Ala Lys Arg Thr Lys Pro Asn Gly His
545                 550                 555                 560

Ile Ala Asn Arg Leu Glu Val Asp Ser Asn Thr Ser Ser Gln Ser Ser
                565                 570                 575

Asn Ser Glu Ser Glu Thr Glu Asp Glu Arg Val Gly Glu Asp Thr Pro
            580                 585                 590

Phe Leu Gly Ile Gln Asn Pro Leu Ala Ala Ser Leu Glu Ala Thr Pro
        595                 600                 605

Ala Phe Arg Leu Ala Asp Ser Arg Thr Asn Pro Ala Gly Arg Phe Ser
    610                 615                 620

Thr Gln Glu Glu Ile Gln Ala Arg Leu Ser Ser Val Ile Ala Asn Gln
625                 630                 635                 640

Asp Pro Ile Ala Val
                645

<210> SEQ ID NO 5
<211> LENGTH: 3765
<212> TYPE: DNA
<213> ORGANISM: Homo sapiens
<220> FEATURE:
<221> NAME/KEY: CDS
<222> LOCATION: (1)...(3765)

<400> SEQUENCE: 5 atg gag ctg gcg gcc ttg tgc cgc tgg ggg ctc ctc ctc gcc ctc ttg      48
Met Glu Leu Ala Ala Leu Cys Arg Trp Gly Leu Leu Leu Ala Leu Leu
1               5                   10                  15 ccc ccc gga gcc gcg agc acc caa gtg tgc acc ggc aca gac atg aag      96
Pro Pro Gly Ala Ala Ser Thr Gln Val Cys Thr Gly Thr Asp Met Lys
            20                  25                  30 ctg cgg ctc cct gcc agt ccc gag acc cac ctg gac atg ctc cgc cac     144
Leu Arg Leu Pro Ala Ser Pro Glu Thr His Leu Asp Met Leu Arg His
        35                  40                  45 ctc tac cag ggc tgc cag gtg gtg cag gga aac ctg gaa ctc acc tac     192
Leu Tyr Gln Gly Cys Gln Val Val Gln Gly Asn Leu Glu Leu Thr Tyr
    50                  55                  60 ctg ccc acc aat gcc agc ctg tcc ttc ctg cag gat atc cag gag gtg     240
Leu Pro Thr Asn Ala Ser Leu Ser Phe Leu Gln Asp Ile Gln Glu Val
65                  70                  75                  80
```

```
cag ggc tac gtg ctc atc gct cac aac caa gtg agg cag gtc cca ctg    288
Gln Gly Tyr Val Leu Ile Ala His Asn Gln Val Arg Gln Val Pro Leu
             85                  90                  95 cag agg ctg cgg att gtg cga ggc acc cag ctc ttt gag gac aac tat    336
Gln Arg Leu Arg Ile Val Arg Gly Thr Gln Leu Phe Glu Asp Asn Tyr
            100                 105                 110 gcc ctg gcc gtg cta gac aat gga gac ccg ctg aac aat acc acc cct    384
Ala Leu Ala Val Leu Asp Asn Gly Asp Pro Leu Asn Asn Thr Thr Pro
        115                 120                 125 gtc aca ggg gcc tcc cca gga ggc ctg cgg gag ctg cag ctt cga agc    432
Val Thr Gly Ala Ser Pro Gly Gly Leu Arg Glu Leu Gln Leu Arg Ser
    130                 135                 140 ctc aca gag atc ttg aaa gga ggg gtc ttg atc cag cgg aac ccc cag    480
Leu Thr Glu Ile Leu Lys Gly Gly Val Leu Ile Gln Arg Asn Pro Gln
145                 150                 155                 160 ctc tgc tac cag gac acg att ttg tgg aag gac atc ttc cac aag aac    528
Leu Cys Tyr Gln Asp Thr Ile Leu Trp Lys Asp Ile Phe His Lys Asn
                165                 170                 175 aac cag ctg gct ctc aca ctg ata gac acc aac cgc tct cgg gcc tgc    576
Asn Gln Leu Ala Leu Thr Leu Ile Asp Thr Asn Arg Ser Arg Ala Cys
            180                 185                 190 cac ccc tgt tct ccg atg tgt aag ggc tcc cgc tgt tgg gga gag agt    624
His Pro Cys Ser Pro Met Cys Lys Gly Ser Arg Cys Trp Gly Glu Ser
        195                 200                 205 tct gag gat tgt cag agc ctg acg cgc act gtc tgt gcc ggt ggc tgt    672
Ser Glu Asp Cys Gln Ser Leu Thr Arg Thr Val Cys Ala Gly Gly Cys
    210                 215                 220 gcc cgc tgc aag ggg cca ctg ccc act gac tgc tgc cat gag cag tgt    720
Ala Arg Cys Lys Gly Pro Leu Pro Thr Asp Cys Cys His Glu Gln Cys
225                 230                 235                 240 gct gcc ggc tgc acg ggc ccc aag cac tct gac tgc ctg gcc tgc ctc    768
Ala Ala Gly Cys Thr Gly Pro Lys His Ser Asp Cys Leu Ala Cys Leu
                245                 250                 255 cac ttc aac cac agt ggc atc tgt gag ctg cac tgc cca gcc ctg gtc    816
His Phe Asn His Ser Gly Ile Cys Glu Leu His Cys Pro Ala Leu Val
            260                 265                 270 acc tac aac aca gac acg ttt gag tcc atg ccc aat ccc gag ggc cgg    864
Thr Tyr Asn Thr Asp Thr Phe Glu Ser Met Pro Asn Pro Glu Gly Arg
        275                 280                 285 tat aca ttc ggc gcc agc tgt gtg act gcc tgt ccc tac aac tac ctt    912
Tyr Thr Phe Gly Ala Ser Cys Val Thr Ala Cys Pro Tyr Asn Tyr Leu
    290                 295                 300 tct acg gac gtg gga tcc tgc acc ctc gtc tgc ccc ctg cac aac caa    960
Ser Thr Asp Val Gly Ser Cys Thr Leu Val Cys Pro Leu His Asn Gln
305                 310                 315                 320 gag gtg aca gca gag gat gga aca cag cgg tgt gag aag tgc agc aag    1008
Glu Val Thr Ala Glu Asp Gly Thr Gln Arg Cys Glu Lys Cys Ser Lys
                325                 330                 335 ccc tgt gcc cga gtg tgc tat ggt ctg ggc atg gag cac ttg cga gag    1056
Pro Cys Ala Arg Val Cys Tyr Gly Leu Gly Met Glu His Leu Arg Glu
            340                 345                 350 gtg agg gca gtt acc agt gcc aat atc cag gag ttt gct ggc tgc aag    1104
Val Arg Ala Val Thr Ser Ala Asn Ile Gln Glu Phe Ala Gly Cys Lys
        355                 360                 365 aag atc ttt ggg agc ctg gca ttt ctg ccg gag agc ttt gat ggg gac    1152
Lys Ile Phe Gly Ser Leu Ala Phe Leu Pro Glu Ser Phe Asp Gly Asp
    370                 375                 380 cca gcc tcc aac act gcc ccg ctc cag cca gag cag ctc caa gtg ttt    1200
Pro Ala Ser Asn Thr Ala Pro Leu Gln Pro Glu Gln Leu Gln Val Phe
385                 390                 395                 400
```

```
gag act ctg gaa gag atc aca ggt tac cta tac atc tca gca tgg ccg    1248
Glu Thr Leu Glu Glu Ile Thr Gly Tyr Leu Tyr Ile Ser Ala Trp Pro
            405                 410                 415 gac agc ctg cct gac ctc agc gtc ttc cag aac ctg caa gta atc cgg    1296
Asp Ser Leu Pro Asp Leu Ser Val Phe Gln Asn Leu Gln Val Ile Arg
        420                 425                 430 gga cga att ctg cac aat ggc gcc tac tcg ctg acc ctg caa ggg ctg    1344
Gly Arg Ile Leu His Asn Gly Ala Tyr Ser Leu Thr Leu Gln Gly Leu
            435                 440                 445 ggc atc agc tgg ctg ggg ctg cgc tca ctg agg gaa ctg ggc agt gga    1392
Gly Ile Ser Trp Leu Gly Leu Arg Ser Leu Arg Glu Leu Gly Ser Gly
        450                 455                 460 ctg gcc ctc atc cac cat aac acc cac ctc tgc ttc gtg cac acg gtg    1440
Leu Ala Leu Ile His His Asn Thr His Leu Cys Phe Val His Thr Val
465                 470                 475                 480 ccc tgg gac cag ctc ttt cgg aac ccg cac caa gct ctg ctc cac act    1488
Pro Trp Asp Gln Leu Phe Arg Asn Pro His Gln Ala Leu Leu His Thr
            485                 490                 495 gcc aac cgg cca gag gac gag tgt gtg ggc gag ggc ctg gcc tgc cac    1536
Ala Asn Arg Pro Glu Asp Glu Cys Val Gly Glu Gly Leu Ala Cys His
        500                 505                 510 cag ctg tgc gcc cga ggg cac tgc tgg ggt cca ggg ccc acc cag tgt    1584
Gln Leu Cys Ala Arg Gly His Cys Trp Gly Pro Gly Pro Thr Gln Cys
            515                 520                 525 gtc aac tgc agc cag ttc ctt cgg ggc cag gag tgc gtg gag gaa tgc    1632
Val Asn Cys Ser Gln Phe Leu Arg Gly Gln Glu Cys Val Glu Glu Cys
        530                 535                 540 cga gta ctg cag ggg ctc ccc agg gag tat gtg aat gcc agg cac tgt    1680
Arg Val Leu Gln Gly Leu Pro Arg Glu Tyr Val Asn Ala Arg His Cys
545                 550                 555                 560 ttg ccg tgc cac cct gag tgt cag ccc cag aat ggc tca gtg acc tgt    1728
Leu Pro Cys His Pro Glu Cys Gln Pro Gln Asn Gly Ser Val Thr Cys
            565                 570                 575 ttt gga ccg gag gct gac cag tgt gtg gcc tgt gcc cac tat aag gac    1776
Phe Gly Pro Glu Ala Asp Gln Cys Val Ala Cys Ala His Tyr Lys Asp
        580                 585                 590 cct ccc ttc tgc gtg gcc cgc tgc ccc agc ggt gtg aaa cct gac ctc    1824
Pro Pro Phe Cys Val Ala Arg Cys Pro Ser Gly Val Lys Pro Asp Leu
            595                 600                 605 tcc tac atg ccc atc tgg aag ttt cca gat gag gag ggc gca tgc cag    1872
Ser Tyr Met Pro Ile Trp Lys Phe Pro Asp Glu Glu Gly Ala Cys Gln
        610                 615                 620 cct tgc ccc atc aac tgc acc cac tcc tgt gtg gac ctg gat gac aag    1920
Pro Cys Pro Ile Asn Cys Thr His Ser Cys Val Asp Leu Asp Asp Lys
625                 630                 635                 640 ggc tgc ccc gcc gag cag aga gcc agc cct ctg acg tcc atc gtc tct    1968
Gly Cys Pro Ala Glu Gln Arg Ala Ser Pro Leu Thr Ser Ile Val Ser
            645                 650                 655 gcg gtg gtt ggc att ctg ctg gtc gtg gtc ttg ggg gtg gtc ttt ggg    2016
Ala Val Val Gly Ile Leu Leu Val Val Val Leu Gly Val Val Phe Gly
        660                 665                 670 atc ctc atc aag cga cgg cag cag aag atc cgg aag tac acg atg cgg    2064
Ile Leu Ile Lys Arg Arg Gln Gln Lys Ile Arg Lys Tyr Thr Met Arg
            675                 680                 685 aga ctg ctg cag gaa acg gag ctg gtg gag ccg ctg aca cct agc gga    2112
Arg Leu Leu Gln Glu Thr Glu Leu Val Glu Pro Leu Thr Pro Ser Gly
        690                 695                 700 gcg atg ccc aac cag gcg cag atg cgg atc ctg aaa gag acg gag ctg    2160
Ala Met Pro Asn Gln Ala Gln Met Arg Ile Leu Lys Glu Thr Glu Leu
```

```
                                                           -continued
705               710               715               720
agg aag gtg aag gtg ctt gga tct ggc gct ttt ggc aca gtc tac aag           2208
Arg Lys Val Lys Val Leu Gly Ser Gly Ala Phe Gly Thr Val Tyr Lys
                725               730               735 ggc atc tgg atc cct gat ggg gag aat gtg aaa att cca gtg gcc atc           2256
Gly Ile Trp Ile Pro Asp Gly Glu Asn Val Lys Ile Pro Val Ala Ile
            740               745               750 aaa gtg ttg agg gaa aac aca tcc ccc aaa gcc aac aaa gaa atc tta           2304
Lys Val Leu Arg Glu Asn Thr Ser Pro Lys Ala Asn Lys Glu Ile Leu
        755               760               765 gac gaa gca tac gtg atg gct ggt gtg ggc tcc cca tat gtc tcc cgc           2352
Asp Glu Ala Tyr Val Met Ala Gly Val Gly Ser Pro Tyr Val Ser Arg
    770               775               780 ctt ctg ggc atc tgc ctg aca tcc acg gtg cag ctg gtg aca cag ctt           2400
Leu Leu Gly Ile Cys Leu Thr Ser Thr Val Gln Leu Val Thr Gln Leu
785               790               795               800 atg ccc tat ggc tgc ctc tta gac cat gtc cgg gaa aac cgc gga cgc           2448
Met Pro Tyr Gly Cys Leu Leu Asp His Val Arg Glu Asn Arg Gly Arg
                805               810               815 ctg ggc tcc cag gac ctg ctg aac tgg tgt atg cag att gcc aag ggg           2496
Leu Gly Ser Gln Asp Leu Leu Asn Trp Cys Met Gln Ile Ala Lys Gly
            820               825               830 atg agc tac ctg gag gat gtg cgg ctc gta cac agg gac ttg gcc gct           2544
Met Ser Tyr Leu Glu Asp Val Arg Leu Val His Arg Asp Leu Ala Ala
        835               840               845 cgg aac gtg ctg gtc aag agt ccc aac cat gtc aaa att aca gac ttc           2592
Arg Asn Val Leu Val Lys Ser Pro Asn His Val Lys Ile Thr Asp Phe
    850               855               860 ggg ctg gct cgg ctg ctg gac att gac gag aca gag tac cat gca gat           2640
Gly Leu Ala Arg Leu Leu Asp Ile Asp Glu Thr Glu Tyr His Ala Asp
865               870               875               880 ggg ggc aag gtg ccc atc aag tgg atg gcg ctg gag tcc att ctc cgc           2688
Gly Gly Lys Val Pro Ile Lys Trp Met Ala Leu Glu Ser Ile Leu Arg
                885               890               895 cgg cgg ttc acc cac cag agt gat gtg tgg agt tat ggt gtg act gtg           2736
Arg Arg Phe Thr His Gln Ser Asp Val Trp Ser Tyr Gly Val Thr Val
            900               905               910 tgg gag ctg atg act ttt ggg gcc aaa cct tac gat ggg atc cca gcc           2784
Trp Glu Leu Met Thr Phe Gly Ala Lys Pro Tyr Asp Gly Ile Pro Ala
        915               920               925 cgg gag atc cct gac ctg ctg gaa aag ggg gag cgg ctg ccc cag ccc           2832
Arg Glu Ile Pro Asp Leu Leu Glu Lys Gly Glu Arg Leu Pro Gln Pro
    930               935               940 ccc atc tgc acc att gat gtc tac atg atc atg gtc aaa tgt tgg atg           2880
Pro Ile Cys Thr Ile Asp Val Tyr Met Ile Met Val Lys Cys Trp Met
945               950               955               960 att gac tct gaa tgt cgg cca aga ttc cgg gag ttg gtg tct gaa ttc           2928
Ile Asp Ser Glu Cys Arg Pro Arg Phe Arg Glu Leu Val Ser Glu Phe
                965               970               975 tcc cgc atg gcc agg gac ccc cag cgc ttt gtg gtc atc cag aat gag           2976
Ser Arg Met Ala Arg Asp Pro Gln Arg Phe Val Val Ile Gln Asn Glu
            980               985               990 gac ttg ggc cca gcc agt ccc ttg gac agc acc ttc tac cgc tca ctg           3024
Asp Leu Gly Pro Ala Ser Pro Leu Asp Ser Thr Phe Tyr Arg Ser Leu
        995               1000              1005 ctg gag gac gat gac atg ggg gac ctg gtg gat gct gag gag tat ctg           3072
Leu Glu Asp Asp Asp Met Gly Asp Leu Val Asp Ala Glu Glu Tyr Leu
    1010              1015              1020 gta ccc cag cag ggc ttc ttc tgt cca gac cct gcc ccg ggc gct ggg           3120
```

```
Val Pro Gln Gln Gly Phe Phe Cys Pro Asp Pro Ala Pro Gly Ala Gly
1025                1030                1035                1040 ggc atg gtc cac cac agg cac cgc agc tca tct acc agg agt ggc ggt     3168
Gly Met Val His His Arg His Arg Ser Ser Ser Thr Arg Ser Gly Gly
                    1045                1050                1055 ggg gac ctg aca cta ggg ctg gag ccc tct gaa gag gag gcc ccc agg     3216
Gly Asp Leu Thr Leu Gly Leu Glu Pro Ser Glu Glu Glu Ala Pro Arg
                1060                1065                1070 tct cca ctg gca ccc tcc gaa ggg gct ggc tcc gat gta ttt gat ggt     3264
Ser Pro Leu Ala Pro Ser Glu Gly Ala Gly Ser Asp Val Phe Asp Gly
            1075                1080                1085 gac ctg gga atg ggg gca gcc aag ggg ctg caa agc ctc ccc aca cat     3312
Asp Leu Gly Met Gly Ala Ala Lys Gly Leu Gln Ser Leu Pro Thr His
        1090                1095                1100 gac ccc agc cct cta cag cgg tac agt gag gac ccc aca gta ccc ctg     3360
Asp Pro Ser Pro Leu Gln Arg Tyr Ser Glu Asp Pro Thr Val Pro Leu
1105                1110                1115                1120 ccc tct gag act gat ggc tac gtt gcc ccc ctg acc tgc agc ccc cag     3408
Pro Ser Glu Thr Asp Gly Tyr Val Ala Pro Leu Thr Cys Ser Pro Gln
                1125                1130                1135 cct gaa tat gtg aac cag cca gat gtt cgg ccc cag ccc cct tcg ccc     3456
Pro Glu Tyr Val Asn Gln Pro Asp Val Arg Pro Gln Pro Pro Ser Pro
            1140                1145                1150 cga gag ggc cct ctg cct gct gcc cga cct gct ggt gcc act ctg gaa     3504
Arg Glu Gly Pro Leu Pro Ala Ala Arg Pro Ala Gly Ala Thr Leu Glu
        1155                1160                1165 agg gcc aag act ctc tcc cca ggg aag aat ggg gtc gtc aaa gac gtt     3552
Arg Ala Lys Thr Leu Ser Pro Gly Lys Asn Gly Val Val Lys Asp Val
1170                1175                1180 ttt gcc ttt ggg ggt gcc gtg gag aac ccc gag tac ttg aca ccc cag     3600
Phe Ala Phe Gly Gly Ala Val Glu Asn Pro Glu Tyr Leu Thr Pro Gln
1185                1190                1195                1200 gga gga gct gcc cct cag ccc cac cct cct cct gcc ttc agc cca gcc     3648
Gly Gly Ala Ala Pro Gln Pro His Pro Pro Pro Ala Phe Ser Pro Ala
                1205                1210                1215 ttc gac aac ctc tat tac tgg gac cag gac cca cca gag cgg ggg gct     3696
Phe Asp Asn Leu Tyr Tyr Trp Asp Gln Asp Pro Pro Glu Arg Gly Ala
            1220                1225                1230 cca ccc agc acc ttc aaa ggg aca cct acg gca gag aac cca gag tac     3744
Pro Pro Ser Thr Phe Lys Gly Thr Pro Thr Ala Glu Asn Pro Glu Tyr
        1235                1240                1245 ctg ggt ctg gac gtg cca gtg                                         3765
Leu Gly Leu Asp Val Pro Val
    1250                1255

<210> SEQ ID NO 6
<211> LENGTH: 1255
<212> TYPE: PRT
<213> ORGANISM: Homo sapiens

<400> SEQUENCE: 6

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60
```

-continued

```
Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
```

```
                    485               490               495
Ala Asn Arg Pro Glu Asp Glu Cys Val Gly Glu Gly Leu Ala Cys His
                500               505               510

Gln Leu Cys Ala Arg Gly His Cys Trp Gly Pro Gly Pro Thr Gln Cys
            515               520               525

Val Asn Cys Ser Gln Phe Leu Arg Gly Gln Glu Cys Val Glu Glu Cys
        530               535               540

Arg Val Leu Gln Gly Leu Pro Arg Glu Tyr Val Asn Ala Arg His Cys
545               550               555               560

Leu Pro Cys His Pro Glu Cys Gln Pro Gln Asn Gly Ser Val Thr Cys
                565               570               575

Phe Gly Pro Glu Ala Asp Gln Cys Val Ala Cys Ala His Tyr Lys Asp
            580               585               590

Pro Pro Phe Cys Val Ala Arg Cys Pro Ser Gly Val Lys Pro Asp Leu
        595               600               605

Ser Tyr Met Pro Ile Trp Lys Phe Pro Asp Glu Glu Gly Ala Cys Gln
    610               615               620

Pro Cys Pro Ile Asn Cys Thr His Ser Cys Val Asp Leu Asp Asp Lys
625               630               635               640

Gly Cys Pro Ala Glu Gln Arg Ala Ser Pro Leu Thr Ser Ile Val Ser
                645               650               655

Ala Val Val Gly Ile Leu Leu Val Val Leu Gly Val Val Phe Gly
            660               665               670

Ile Leu Ile Lys Arg Arg Gln Gln Lys Ile Arg Lys Tyr Thr Met Arg
        675               680               685

Arg Leu Leu Gln Glu Thr Glu Leu Val Glu Pro Leu Thr Pro Ser Gly
    690               695               700

Ala Met Pro Asn Gln Ala Gln Met Arg Ile Leu Lys Glu Thr Glu Leu
705               710               715               720

Arg Lys Val Lys Val Leu Gly Ser Gly Ala Phe Gly Thr Val Tyr Lys
                725               730               735

Gly Ile Trp Ile Pro Asp Gly Glu Asn Val Lys Ile Pro Val Ala Ile
            740               745               750

Lys Val Leu Arg Glu Asn Thr Ser Pro Lys Ala Asn Lys Glu Ile Leu
        755               760               765

Asp Glu Ala Tyr Val Met Ala Gly Val Gly Ser Pro Tyr Val Ser Arg
    770               775               780

Leu Leu Gly Ile Cys Leu Thr Ser Thr Val Gln Leu Val Thr Gln Leu
785               790               795               800

Met Pro Tyr Gly Cys Leu Leu Asp His Val Arg Glu Asn Arg Gly Arg
                805               810               815

Leu Gly Ser Gln Asp Leu Leu Asn Trp Cys Met Gln Ile Ala Lys Gly
            820               825               830

Met Ser Tyr Leu Glu Asp Val Arg Leu Val His Arg Asp Leu Ala Ala
        835               840               845

Arg Asn Val Leu Val Lys Ser Pro Asn His Val Lys Ile Thr Asp Phe
    850               855               860

Gly Leu Ala Arg Leu Leu Asp Ile Asp Glu Thr Glu Tyr His Ala Asp
865               870               875               880

Gly Gly Lys Val Pro Ile Lys Trp Met Ala Leu Glu Ser Ile Leu Arg
                885               890               895

Arg Arg Phe Thr His Gln Ser Asp Val Trp Ser Tyr Gly Val Thr Val
            900               905               910
```

```
Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
            965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr Leu
            1010                1015                1020

Val Pro Gln Gln Gly Phe Phe Cys Pro Asp Pro Ala Pro Gly Ala Gly
1025                1030                1035                1040

Gly Met Val His His Arg His Arg Ser Ser Ser Thr Arg Ser Gly Gly
            1045                1050                1055

Gly Asp Leu Thr Leu Gly Leu Glu Pro Ser Glu Glu Glu Ala Pro Arg
            1060                1065                1070

Ser Pro Leu Ala Pro Ser Glu Gly Ala Gly Ser Asp Val Phe Asp Gly
            1075                1080                1085

Asp Leu Gly Met Gly Ala Ala Lys Gly Leu Gln Ser Leu Pro Thr His
            1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
            1125                1130                1135

Pro Glu Tyr Val Asn Gln Pro Asp Val Arg Pro Gln Pro Pro Ser Pro
            1140                1145                1150

Arg Glu Gly Pro Leu Pro Ala Ala Arg Pro Ala Gly Ala Thr Leu Glu
            1155                1160                1165

Arg Ala Lys Thr Leu Ser Pro Gly Lys Asn Gly Val Val Lys Asp Val
            1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Ala Phe Ser Pro Ala
            1205                1210                1215

Phe Asp Asn Leu Tyr Tyr Trp Asp Gln Asp Pro Pro Glu Arg Gly Ala
            1220                1225                1230

Pro Pro Ser Thr Phe Lys Gly Thr Pro Thr Ala Glu Asn Pro Glu Tyr
            1235                1240                1245

Leu Gly Leu Asp Val Pro Val
            1250                1255

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
ctagtctcta gatccgaggt gggcaactct                              30
```

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
taccgatcta gatttcggac agagaccccc                                      30

<210> SEQ ID NO 9
<211> LENGTH: 27
<212> TYPE: DNA
<213> ORGANISM: Artificial Sequence
<220> FEATURE:
<223> OTHER INFORMATION: primer

<400> SEQUENCE: 9
ctactctcta gatccgaggg caactct                                         27

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10
taccgatcta gatttcggac agagaccccc                                      30

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
gcgatgctgc gaaccaatac c                                               21

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
ggtattggtt cgcagcatcg c                                               21

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
cgatgctgag gcccaatacc ag                                              22

<210> SEQ ID NO 14
<211> LENGTH: 22
<212> TYPE: DNA
<213> ORGANISM: Artificial Sequence
<220> FEATURE:
<223> OTHER INFORMATION: primer

```
<400> SEQUENCE: 14
ctggtattgg cgctcagcat cg                                          22

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
gacactgtac gcgctctacg ag                                          22

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
ctcgtagagc cggtacagtg tc                                          22

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
gggaaccttg cgattgtgct c                                           21

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
gagcacaatc gcaaggttcc c                                           21

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
cttgagattg cgctcacgg                                              19

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
cgtgagcgca atctcaaggt                                             20

<210> SEQ ID NO 21
```

```
<211> LENGTH: 24
<212> TYPE: DNA
<213> ORGANISM: Artificial Sequence
<220> FEATURE:
<223> OTHER INFORMATION: primer

<400> SEQUENCE: 21
ccatgaatga agcctctact ctac                                              24

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22
gtagagtaga gcgttcattc atgg                                              24

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
gacccaggcc tacgatggga a                                                 21

<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24
cttcccatcg taggcctggg tc                                                22
```

METHODS AND MATERIALS FOR CHARACTERIZING AND MODULATING INTERACTION BETWEEN HEREGULIN AND HER3

RELATED APPLICATIONS

This application is a divisional application that claims the benefit under 35 U.S.C. § 120 of U.S. patent application Ser. No. 10/207,498, filed Jul. 29,2002 (now U.S. Pat. No. 7,125,680), which claims priority under Section 119(e) from U.S. Provisional Application Ser. No. 60/308,341 filed Jul. 27, 2001, the contents of each of which are incorporated herein by reference.

STATEMENT OF GOVERNMENT SUPPORT

This invention was made with support from GM031299 from the National Institues of Health. The government has certain rights to this invention.

FIELD OF THE INVENTION

This invention relates generally to HER3 compositions, and to methods of using HER3 compositions to modulate the interaction between heregulin and HER3 and for example, the biological activities of heregulin and HER3. The invention also relates to methods of identifying molecules that bind to the heregulin binding site of HER3. The invention also relates to methods for in vitro, in situ, and/or in vivo diagnosis and/or treatment of mammalian cells or pathological conditions associated with HER3 and heregulin.

BACKGROUND OF THE INVENTION

Cancers are the second most prevalent cause of death in the United States, causing 450,000 deaths per year. One in three Americans will develop cancer, and one in five will die of cancer. While substantial progress has been made in identifying some of the likely environmental and hereditary causes of cancer, there is a need for substantial improvement in the diagnosis and therapy for cancer and related diseases and disorders.

A number of so-called cancer genes, i.e., genes that have been implicated in the etiology of cancer, have been identified in connection with hereditary forms of cancer and in a large number of well-studied tumor cells. Cancer genes are broadly classified into "oncogenes" which, when activated, promote tumorigenesis, and "tumor suppressor genes" which, when damaged, fail to suppress tumorigenesis. While these classifications provide a useful method for conceptualizing tumorigenesis, it is also possible that a particular gene may play differing roles depending upon the particular allelic form of that gene, its regulatory elements, the genetic background and the tissue environment in which it is operating. Human epidermal growth factor receptor 3 is one of these genes implicated in the etiology of cancer (see, e.g. Munster et al., Cancer Res. Jun. 1, 2002; 62(11):3132-7; Menard et al. J Cell Physiol 2000 February; 182(2):150-62; Basso et al., Oncogene 2002 Feb. 14, 2002; 21(8):1159-66; and Yarden Oncology 2001; 61 Suppl 2:1-13).

Human epidermal growth factor receptor 3 (HER3) (see, e.g. Kraus et al., (1989) Proc. Natl. Acad. Sci. U.S.A. 86, 9193-9197) is a member of the type I receptor tyrosine kinase (RTK) family, which also includes EGFR, HER2/neu, and HER4 (see, e.g. Ullrich et al., (1984) Nature 309, 418-425; Schechter et al., (1985) Science 229, 976-978; Plowman et al., (1993) Proc. Natl. Acad. Sci. U.S.A. 90, 1746-1750). HER3 forms heterodimers with other members of the type I RTK family, including the HER2/neu receptor (see, e.g. Sliwkowski et al., (1994) J. Biol. Chem. 269, 14661-14665; Fitzpatrick et al., (1998) FEBS Lett. 431, 102-106; Heldin, C. H. (1995) Cell 80, 213-223; Tzahar et al., (1997) EMBO J. 16, 938-4950). The HER2/neu receptor is amplified and overexpressed in 25-30% of human breast and 8-11% off human ovarian cancers. This overexpression correlates with increased morbidity and mortality, and there is evidence that the overexpressed HER2 receptor leads to aggressive malignancies (see, e.g. Slamon et al., (1987) Science 235, 177-182; Slamon et al., (1989) Science 244, 707-712; Plowman et al., (1993) Nature 366, 473-475; Dougall et al., (1996) DNA Cell Biol. 15, 31-40).

Cells expressing only HER2 receptors alone and not other members of the EGFR family fail to bind heregulin, but HER2/neu has high tyrosine kinase activity. HER3 is a kinase defective receptor (see, e.g. Guy et al. (1994) *Proc Natl Acad Sci USA* 91(17), 8132-6), but has binding affinity for heregulin (see, e.g. Carraway et al. (1994) *J Biol Chem* 269(19), 14303-6). The HER2/HER3 heterodimer forms a high affinity heregulin receptor with tyrosine kinase activity. Heregulin binding to cells that display the HER2/HER3 heterodimer causes a mitogenic response both in vitro and in vivo, so understanding this interaction is of medical importance (see, e.g. Aguilar et al., (1999) Oncogene 18, 6050-6062; Sliwkowski et al. (1994) *J Biol Chem* 269(20), 14661-5; Heldin, C. H. (1995) *Cell* 80(2), 213-23; Tzahar et al. (1997) *Embo J* 16(16), 4938-50). Alternate transcripts of HER3 isolated from an ovarian carcinoma-derived cell line have been identified which encode truncated forms of the extracellular domain of HER3, including three clones where the protein products were soluble secreted proteins (see, e.g. Lee, H., and Maihle, N. J. (1998) *Oncogene* 16(25), 3243-52). A naturally occurring secreted form of HER3 has been found to inhibit heregulin-stimulated activation of HER3 (see, e.g. Lee et al. (2001) *Cancer Res* 61(11), 4467-73). This provides evidence that HER3 could be an important target in breast cancer therapy.

Type I receptor tyrosine kinases typically contain four extracellular domains, a single hydrophobic transmembrane segment, and a cytoplasmic tyrosine kinase domain (see, e.g. Ullrich, A., and Schlessinger, J. (1990) Cell 61, 203-212). HER2/neu is a very active tyrosine kinase, but cells expressing HER2/neu alone, and not other members of the EGFR family, fail to bind heregulin. Conversely, the HER3 receptor binds heregulin but has low tyrosine kinase activity (see, e.g. Guy et al., (1994) Proc. Natl. Acad. Sci. U.S.A. 91, 8132-8136; Carraway et al., (1994) J. Biol. Chem. 269, 14303-14306). As noted above, the HER2/HER3 heterodimer is a high affinity heregulin binding complex with signaling activity through the HER-2 kinase domain. To date, the domains of HER3 involved in ligand binding and heterodimerization have not been identified.

Thus far, the high carbohydrate content (see, e.g. Horan et al., (1995) J. Biol. Chem. 270, 24604-24608) and the relatively large size (~180 kDa) of the receptors in the EGFR family have frustrated structural analysis by x-ray crystallography and NMR, so other methods have been sought to illuminate the structure and function of HER3. The extracellular domains (ECDs) of the type I RTKs have been divided into four domains: I, II, III, and IV, based on sequence analysis (see, e.g. Yarden, Y., and Ullrich, A. (1988) Annu. Rev. Biochem. 57, 443-478). Domains II and IV are cysteine-rich and are similar in sequence. Domains I and III also have sequence similarity (see, e.g. Yarden, Y., and Ullrich, A. (1988) Annu. Rev. Biochem. 57, 443-478; Lax et al., (1988) Mol. Cell. Biol. 8, 1970-1978). Little is known about the specific function of each domain except in EGFR, where several lines of evidence provide evidence that the major determinants for EGF binding lie in domain III. These lines of evidence include the following: 1) the exchange of domain III in chicken EGFR for domain III from human EGFR confers binding of human EGF (see, e.g. Lax et al., (1989) EMBO J. 8, 421-427; Lax et al., (1991) Cell Regul. 2, 337-345); 2) monoclonal antibodies that recognize residues in domain III prevent EGF binding to EGFR (see, e.g. Wu et al., (1989) J. Biol. Chem. 264, 17469-17475); 3) cross-linking of EGF to EGFR identified residues in domain III (see, e.g. Summerfield et al., (1996) J. Biol. Chem. 271, 19656-19659; Wu et al., (1990) Proc. Natl. Acad. Sci. U.S.A. 87, 3151-3155); and 4) limited proteolysis of the ECD of EGFR produced a fragment that encompassed domain III, which bound transforming growth factor, with the observation that binding could be enhanced by including portions of domain IV (see, e.g. Kohda et al., (1993) J. Biol. Chem. 268, 1976-1981). Additional studies from cross-linking experiments indicated that bound EGF is also close to tyrosine 101 in domain I of murine EGFR (see, e.g. Woltjer et al., (1992) Proc. Natl. Acad. Sci. U.S.A. 89, 7801-7805). Taken together, these experimental results provide evidence that domain I and III are close to the ligand-binding region in EGFR and that domain III contributes most of the binding. HER3 and EGFR have relatively high sequence identity (45% identity in the ECD) and belong to the same family of type 1 tyrosine kinase receptors; however, they bind a different subset of ligands and differ in preference for heterodimerization versus homodimerization (see, e.g. Tzahar et al., (1997) EMBO J. 16, 938-4950; Lemmon et al., (1997) EMBO J. 16, 281-294; Huang et al., (1998) Biochem. J. 331, 113-119; Alimandi et al., (1995) Oncogene 10, 1813-1821).

While the existing art provides a limited understanding of the structure of HER3 and the interaction between heregulin and HER3, this art does not delineate the domains in HER3 responsible for interacting with heregulin. Consequently there is a need in the art for the identification and characterization of the domains in HER3 involved in this interaction so that methods and materials for modulating this interaction can be generated. The disclosure provided herein meets this need.

SUMMARY OF THE INVENTION

The disclosure provided herein identifies and characterizes the domains in the HER3 receptor that interact with the heregulin ligand. In this context, the present invention provides antagonists or agonists of the HER3 receptor such as soluble HER3 variants and methods for using them. The antagonists and agonists described herein find utility for, among other things, in vitro, in situ, or in vivo diagnosis or treatment of mammalian cells or pathological conditions associated with the aberrant expression of heregulin and/or HER3.

A preferred embodiment of the invention is a HER3 variant polypeptide comprising an amino acid sequence which differs from the native sequence HER3 polypeptide sequence of SEQ ID NO: 2 and has one or more of amino acid substitutions at the following residue position(s) in SEQ ID NO: 2: E43; N44; K51; E64; V66; and V110. Another embodiment of the invention is a non-naturally occurring HER3 variant polypeptide consisting essentially of amino acid 20 to amino acid 329 of HER3 polypeptide sequence of SEQ ID NO: 2; wherein the HER3 variant polypeptide specifically binds to the heregulin polypeptide of SEQ ID NO: 4 and exhibits an impaired ability to interact with the HER2 polypeptide of SEQ ID NO: 6.

Related embodiments of this invention include an isolated nucleic acid comprising a nucleotide sequence encoding these HER3 variants, vectors comprising nucleic acids encoding these variants and host cells (e.g. E. coli) containing these vectors. Another related embodiment of the invention is a method of making HER3 variant polypeptide by providing a host cell comprising a vector encoding a HER3 variant, providing culture media, culturing the host cell in the culture media under conditions sufficient to express the HER3 variant polypeptide, recovering the HER3 variant polypeptide from the host cell or culture media, and then purifying the HER3 variant polypeptide. Optionally the HER3 variant polypeptide is conjugated or linked to one or more polyol groups.

The invention also provides methods of conducting screening assays to identify candidate molecules, such as small molecule compounds, polypeptides or antibodies, which act as agonists or antagonists with respect to the interaction between heregulin and HER3. One embodiment of the invention is a method of identifying a compound which specifically binds the heregulin binding domain in a HER3 variant polypeptide comprising amino acid 20 to amino acid 329 of HER3 polypeptide sequence of SEQ ID NO: 2 comprising contacting the HER3 variant polypeptide with a test compound under conditions favorable to binding and determining whether the test compound specifically binds to the HER3 variant polypeptide such that a compound which binds to the HER3 variant polypeptide can be identified. Optionally this method can further comprise determining whether the test compound inhibits the heregulin induced tyrosine kinase activity by contacting mammalian cells that express HER3 receptor with heregulin in the presence and absence of the test compound and then monitoring the mammalian cells for the tyrosine kinase activity associated with the HER2/HER3 polypeptide complex, wherein an inhibition in tyrosine kinase activity in the presence of the test compound as compared to the absence of the test compound identifies the test compound as an inhibitor of heregulin induced tyrosine kinase activity. Alternatively, the method can further comprise determining whether the test compound enhances the heregulin induced tyrosine kinase activity by contacting mammalian cells that express HER3 receptor with heregulin in the presence and absence of the test compound and then monitoring the mammalian cells for the tyrosine kinase activity associated with the HER3 polypeptide, wherein an increase in tyrosine kinase activity in the presence of the test compound as compared to the absence of the test compound identifies the test compound as an enhancer of heregulin induced tyrosine kinase activity.

Yet another embodiment of the invention is a method of determining whether a test compound modulates the interaction between heregulin polypeptide of SEQ ID NO: 2 and a HER3 variant polypeptide comprising amino acid 20 to amino acid 329 of SEQ ID NO: 2 by contacting the HER3 variant polypeptide with a test compound under conditions favorable to binding, contacting the HER3 variant polypeptide with heregulin under conditions favorable to binding and then comparing the binding interaction between the HER3 variant polypeptide and heregulin with the binding interaction between HER3 variant polypeptide and heregulin in the absence of the test compound such that a compound which modulates the interaction between heregulin and the HER3 variant polypeptide can be identified.

Another embodiment of the invention is a method of inhibiting the interaction between a heregulin polypeptide having the sequence shown in SEQ ID NO: 4 and HER3 polypeptide having the sequence shown in SEQ ID NO: 2 comprising exposing the heregulin polypeptide to a non-naturally occurring HER3 variant polypeptide comprising domains I and II of the HER3 polypeptide sequence of SEQ ID NO: 2; wherein the HER3 variant polypeptide specifically binds to the heregulin polypeptide of SEQ ID NO: 4; and exhibits an impaired ability to interact with the HER2 polypeptide of SEQ ID NO: 6. In preferred embodiments of the invention, the HER3 variant polypeptide has an amino acid substitution V110 in SEQ ID NO: 2.

Preferred embodiments of the invention also include anti-HER3 antibodies which are capable of specifically binding to the heregulin binding domain. In a preferred embodiment, the invention provides antibodies which specifically bind to a HER3 polypeptide and inhibit the binding of heregulin ligand to the HER3 receptor. Optionally, the antibodies are monoclonal antibodies.

In one embodiment of the invention, there are provided methods for the use of heregulin antagonists to block or neutralize the interaction between heregulin and HER3. For example, the invention provides a method comprising exposing a mammalian cell, such as an ovarian or breast cell, to one or more heregulin antagonists in an amount effective to decrease, neutralize or block activity of the heregulin ligand. The cell may be in cell culture or in a mammal, e.g. a mammal suffering from, for instance, cancer. Thus, the invention includes a method for treating a mammal suffering from a pathological condition such as cancer comprising administering an effective amount of one or more heregulin antagonists, as disclosed herein.

In addition, the invention provides methods of using HER3 agonists (e.g. anti-HER3 agonist antibodies which target the heregulin binding domain) to, for instance, stimulate or activate HER3 receptor. Such methods will be useful in treating pathological conditions characterized by or associated with insufficient HER3 expression or activity. The HER3 agonists typically comprise agonistic anti-HER3 antibodies or HER3 variant polypeptides. The agonistic activity of such HER3 agonists may comprise enhancing the activity of a native ligand for HER3 or activity which is the same as or substantially the same as (i.e., mimics) the activity of a native ligand for HER3. Typical methods of the invention include methods to treat pathological conditions or diseases in mammals associated with or resulting from increased or enhanced HER3 or heregulin expression and/or activity. In the methods of treatment, HER3 variant polypeptides may be administered which preferably block or reduce the respective receptor binding or activation by heregulin.

The invention also provides compositions which comprise one or more HER3 or heregulin agonists or antagonists. Optionally, the compositions of the invention will include pharmaceutically acceptable carriers or diluents. Preferably, the compositions will include one or more HER3 or heregulin antagonists or agonists in an amount which is therapeutically effective to treat a pathological condition or disease. Optionally, the compositions will include one or more HER3 agonists in an amount which is therapeutically effective to stimulate signal transduction by HER3.

The invention also provides articles of manufacture and kits which include one or more HER3 or heregulin antagonists or agonists.

BRIEF DESCRIPTION OF THE DRAWINGS

FIG. 8. Sequence alignment of domain I of HER3-ECD$^{I-IV}$, IR, and IGF-1R indicates the position of the proteolysis site (▼) in domain I of HER3-ECD$^{I-IV}$ relative to mutations (*) that decrease ligand binding in the IR. A naturally occurring mutation that decreases binding in IR is indicated by an open circle. The "hormone binding footprint" in the IGF-1R structure (43) is indicated by shaded areas in the sequence. This alignment shows that the proteolysis site HER3-ECD$^{I-IV}$ that is protected by hrg corresponds to the analogous putative ligand-binding region in domain L1 in IGF-1R.

DETAILED DESCRIPTION OF THE INVENTION

Figure 1:
FIG. 1. A, limited proteolysis of HER3-ECD$^{I-IV}$ generates two detectable fragments, which remain associated under oxidizing conditions. HER3-ECD$^{I-IV}$ was digested in the presence of trypsin (T) and analyzed in the Phast gel in the presence of the reducing agent β-ME. The proteolytic digest of HER3-ECD$^{I-IV}$ was analyzed on an SDS-PAGE Phast gel (10-15%) in the absence (lane 4) and the presence (lane 3) of the reducing agent β-ME. Nonproteolyzed HER3-ECD$^{I-IV}$ in the presence of β-ME is shown in lane 2. The two fragments in proteolyzed HER3-ECD$^{I-IV}$ remain linked by one or more disulfide bridges. B, a V5 antibody protects HER3-ECD$^{I-IV}$ from cleavage at the C terminus. When HER3-ECD$^{I-IV}$ is proteolyzed in the absence of the V5 antibody, the C terminus is digested and could not be visualized when probed for the V5 epitope. This gel shows HER3-ECD$^{I-IV}$ proteolyzed for the time indicated in the presence of an antibody against the V5 epitope tag, analyzed on a 4-15% polyacrylamide gradient gel, and transferred to a polyvinylidene difluoride membrane. The C-terminal fragment was identified by Western blotting using an antibody against the C-terminal V5 epitope. The V5 antibody protects the C terminus against proteolytic cleavage and shows that fragment 2 is the C-terminal fragment.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in see Ausubel et al., Current Protocols in Molecular Biology, Wiley Interscience Publishers, (1995) and Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

Briefly, the disclosure provided herein identifies domains I-II of HER3 as the major binding region for heregulin and identifies residue positions in HER3 that, when mutated, produce heregulin binding polypeptides which have an altered affinity for this ligand. Prior to this discovery, the region of ligand binding in HER3 was unknown. This domain localization is unexpected in view of observations of EGFR (in which the binding of its ligand occurs in domain III), a closely related receptor that has a sequence identity HER3 and which belongs in the same family of type 1 kinase receptors. See, e.g. Singer et al., JBC (2001), 276(47): 44266-44274. Various aspects and embodiments of the invention disclosed herein are provided in the description below.

I. Abbreviations

Abbreviations used include: HER, human epidermal growth factor receptor; ECD, extracellular domain; EGF, epidermal growth factor; EGFR, epidermal growth factor receptor; hrg, 60-residue EGF-like domain of human heregulin 1; IGF-1R, insulin growth factor-1 receptor; IR, insulin receptor; NA$_5$-hrg, binding-deficient hrg mutant; PBS, phosphate-buffered saline; RTK, receptor tyrosine kinase; trx-hrg, thioredoxin-heregulin fusion; β-ME, β-mercaptoethanol; PAGE, polyacrylamide gel electrophoresis; BSA, bovine serum albumin; MALDI, matrix-assisted laser desorption/ionization; SPR, surface plasmon resonance; MES, 4-morpholineethanesulfonic acid.

II. Definitions

The terms "HER3", "HER3 polypeptide" or "HER3 receptor" when used herein encompass "native sequence HER3 polypeptides" and "HER3 variants" (which are further defined herein). "HER3" is a designation given to those polypeptides which are encoded by the nucleic acid molecules comprising the polynucleotide sequences shown in SEQ ID NO: 1 and variants or fragments thereof, nucleic acid molecules comprising the sequence shown in the SEQ ID NO: 1. The HER3 polynucleotides and polypeptides of the invention may be isolated from a variety of sources, such as from human tissue types or from another source, or prepared by recombinant and/or synthetic methods. See, e.g. Plowman et al., PNAS (1990) 87: 4905-4909. As used herein, the term "polypeptide" means an amino acid polymer of at least 6 amino acids.

A "native sequence" HER3 polypeptide comprises a polypeptide having the same amino acid sequence as the corresponding HER3 polypeptide derived from nature. Such native sequence HER3 polypeptides can be isolated from nature or can be produced by recombinant and/or synthetic means. The term "native sequence HER3 polypeptide" specifically encompasses naturally-occurring truncated or secreted forms (e.g., an extracellular domain sequence), naturally-occurring variant forms (e.g., alternatively spliced forms) and naturally-occurring allelic variants of the polypeptide. The HER3 polypeptides of the invention include the HER3 polypeptide comprising or consisting of the contiguous sequence of amino acid residues 1 to 1342 of SEQ ID NO: 2.

A HER3 "extracellular domain" or "ECD" refers to a form of the HER3 polypeptide which is essentially free of the transmembrane and cytoplasmic domains. Ordinarily, a HER3 polypeptide ECD will have less than about 1% of such transmembrane and/or cytoplasmic domains and preferably, will have less than about 0.5% of such domains. It will be understood that any transmembrane domain(s) identified for the HER3 polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified.

Figure 10:
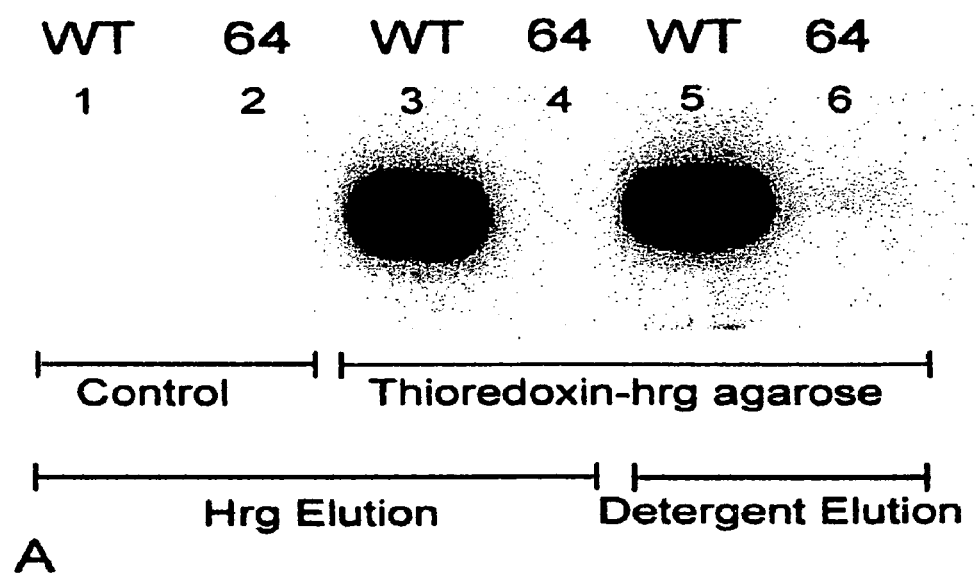
FIG. 10. A, HER3$^{I-II}$ and HER3$^{I-II\ E64A}$ were analyzed in a "pull down assay" in which S-tagged hrg was immobilized on S-protein resin (lanes 3-6) and HER3$^{I-II}$ could be specifically eluted with 1 µM hrg and detergent (lane 3 and 5), but HER3$^{I-II\ E64A}$ was not eluted by either 1 µM hrg or detergent (lane 4 and 6). Both HER3$^{I-II}$ and HER3$^{I-II\ E64A}$ showed little non-specific binding to S-protein resin without immobilized S-tagged hrg (lanes 1-2). This shows that HER3$^{I-II\ E64A}$ does not bind hrg. B, Recombinant HER3$^{I-II\ E64A}$ had no detectable binding greater than 500 nM to the immobilized hrg on the BIAcore chip while HER3$^{I-II}$ showed binding to immobilized trx-hrg with a calculated equilibrium dissociation constant of 68 nM. This shows that HER3$^{I-IIE64A}$ does not bind hrg.
Figure 10:
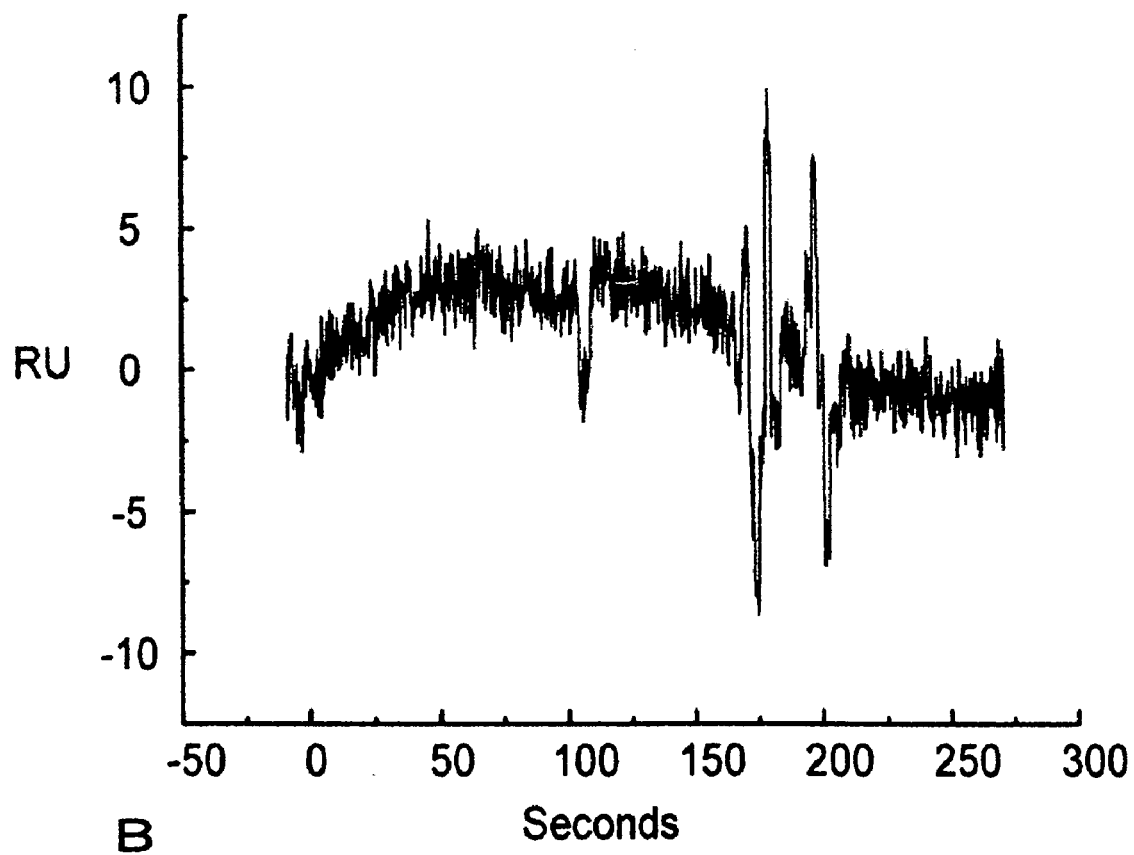

"HER3 variant" means a HER3 polypeptide having at least about 80% amino acid sequence identity with the amino acid sequence of a native sequence full length HER3 or HER3 ECD. Such HER3 variant polypeptides include, for instance, HER3 polypeptides wherein one or more amino acid residues are added, or deleted, at the N- and/or C-terminus, as well as within one or more internal domains, of the full-length amino acid sequence. Fragments of the HER3 ECD are also contemplated. Ordinarily, a HER3 variant polypeptide will have at least about 80% amino acid sequence identity, more preferably at least about 81% amino acid sequence identity, more preferably at least about 82% amino acid sequence identity, more preferably at least about 83% amino acid sequence identity, more preferably at least about 84% amino acid sequence identity, more preferably at least about 85% amino acid sequence identity, more preferably at least about 86% amino acid sequence identity, more preferably at least about 87% amino acid sequence identity, more preferably at least about 88% amino acid sequence identity, more preferably at least about 89% amino acid sequence identity, more preferably at least about 90% amino acid sequence identity, more preferably at least about 91% amino acid sequence identity, more preferably at least about 92% amino acid sequence identity, more preferably at least about 93% amino acid sequence identity, more preferably at least about 94% amino acid sequence identity, more preferably at least about 95% amino acid sequence identity, more preferably at least about 96% amino acid sequence identity, more preferably at least about 97% amino acid sequence identity, more preferably at least about 98% amino acid sequence identity and yet more preferably at least about 99% amino acid sequence identity with a HER3 polypeptide encoded by a nucleic acid molecule shown in FIG. 10 or a specified fragment thereof. HER3 variant polypeptides do not encompass the native HER3 polypeptide sequence. Ordinarily, HER3 variant polypeptides are at least about 10 amino acids in length, often at least about 20 amino acids in length, more often at least about 30 amino acids in length, more often at least about 40 amino acids in length, more often at least about 50 amino acids in length, more often at least about 60 amino acids in length, more often at least about 70 amino acids in length, more often at least about 80 amino acids in length, more often at least about 90 amino acids in length, more often at least about 100 amino acids in length, more often at least about 150 amino acids in length, more often at least about 200 amino acids in length, more often at least about 250 amino acids in length, more often at least about 300 amino acids in length, or more.

The terms "heregulin" or "heregulin polypeptide" when used herein encompass "native sequence heregulin polypeptides" and "heregulin variants". "Heregulin" is a designation given to those polypeptides which are encoded by the nucleic acid molecules comprising the polynucleotide sequences shown in SEQ ID NO: 3 and variants thereof, nucleic acid molecules comprising the sequence shown in the SEQ ID NO: 3, and variants thereof as well as fragments of the above which have the biological activity of the native sequence heregulin. Variants of heregulin will preferably have at least 80%, more preferably, at least 90%, and even more preferably, at least 95% amino acid sequence identity with the native sequence heregulin polypeptide shown in SEQ ID NO: 4. A "native sequence" heregulin polypeptide comprises a polypeptide having the same amino acid sequence as the corresponding heregulin polypeptide derived from nature. Such native sequence heregulin polypeptides can be isolated from nature or can be produced by recombinant and/or synthetic means.

The terms "HER2" or "HER2 polypeptide" when used herein encompass "native sequence HER2 polypeptides" and "HER2 variants". "HER2" is a designation given to those polypeptides which are encoded by the nucleic acid molecules comprising the polynucleotide sequences shown in SEQ ID NO: 5 and variants thereof, nucleic acid molecules comprising the sequence shown in the Figure SEQ ID NO: 5, and variants thereof as well as fragments of the above which have the biological activity of the native sequence HER2. Variants of HER2 will preferably have at least 80%, more preferably, at least 90%, and even more preferably, at least 95% amino acid sequence identity with the native sequence HER2 polypeptide shown in SEQ ID NO: 6. A "native sequence" HER2 polypeptide comprises a polypeptide having the same amino acid sequence as the corresponding HER2 polypeptide derived from nature. Such native sequence HER2 polypeptides can be isolated from nature or can be produced by recombinant and/or synthetic means.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired identity between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, are identified by those that: (1) employ low ionic strength and high temperature for washing, 0.015 M sodium chloride/0.0015 M sodium citrate/0.1% sodium dodecyl sulfate at 50° C.; (2) employ during hybridization a denaturing agent, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" are identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "amino acid" and "amino acids" refer to all naturally occurring L-alpha-amino acids. This definition is meant to include norleucine, ornithine, and homocysteine. The amino acids are identified by either the single-letter or three-letter designations:

| Asp | D | aspartic acid | Ile | I | isoleucine |
|---|---|---|---|---|---|
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

In the Sequence Listing and Figures, certain other single-letter or three-letter designations may be employed to refer to and identify two or more amino acids or nucleotides at a given position in the sequence.

"Percent (%) amino acid sequence identity" with respect to the ligand or receptor polypeptide sequences identified herein is defined as the percentage of amino acid residues in a candidate sequence that are identical with the amino acid residues in such a ligand or receptor sequence identified herein, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

The term "antagonist" is used in the broadest sense, and includes any molecule that partially or fully blocks, inhibits, or neutralizes one or more biological activities of heregulin polypeptide, HER3 polypeptide, or both heregulin and HER3, in vitro, in situ, or in vivo. Examples of such biological activities of heregulin and HER3 polypeptides include binding of heregulin to HER3 and activation of the mitogenic response that is observed when heregulin interacts with HER3, as reported in the literature (see, e.g. Lee et al., (2001) Cancer Research 61, 4467-4473; Aguilar et al., (1999) Oncogene 18, 6050-6052; Marte et al., Oncogene Jan. 5, 1995; 10(1):167-75; and Neve et al., Oncogene Mar. 23, 2000; 19(13):1647-56). An antagonist may function in a direct or indirect manner. For instance, the antagonist may function to partially or fully block, inhibit or neutralize one or more biological activities of heregulin polypeptide, HER3 polypeptide, or both heregulin and HER3, in vitro, in situ, or in vivo as a result of their direct interaction. The antagonist may also function indirectly to partially or fully block, inhibit or neutralize one or more biological activities of heregulin polypeptide, HER3 polypeptide, or both heregulin and HER3, in vitro, in situ, or in vivo as a result of, e.g., blocking or inhibiting another effector molecule. The antagonist molecule may comprise a "dual" antagonist activity wherein the molecule is capable of partially or fully blocking, inhibiting or neutralizing a biological activity of both heregulin and HER3.

The term "agonist" is used in the broadest sense, and includes any molecule that partially or fully enhances, stimulates or activates one or more biological activities of heregulin polypeptide, HER3 polypeptide, or both heregulin and HER3, in vitro, in sited, or in vivo. Examples of such biological activities of heregulin and HER3 may include activation of downstream signal transduction (see, e.g. Aguilar et al., (1999) Oncogene 18, 6050-6052; Marte et al., Oncogene Jan. 5, 1995; 10(1):167-75; and Neve et al., Oncogene 2000 Mar. 23; 19(13):1647-56). An agonist may function in a direct or indirect manner. For instance, the agonist may function to partially or fully enhance, stimulate or activate one or more biological activities of heregulin polypeptide, HER3 polypeptide, or both heregulin and HER3, in vitro, in situ, or in vivo as a result of its direct binding to heregulin or HER3, which causes receptor activation or signal transduction. The agonist may also function indirectly to partially or fully enhance, stimulate or activate one or more biological activities of heregulin polypeptide, HER3 polypeptide, or both heregulin and HER3, in vitro, in situ, or in vivo as a result of, e.g., stimulating another effector molecule which then causes heregulin or HER3 receptor activation or signal transduction. It is contemplated that an agonist may act as an enhancer molecule which functions indirectly to enhance or increase heregulin or HER3 activation or activity. For instance, the agonist may enhance activity of endogenous heregulin or HER3 in a mammal. This could be accomplished, for example, by pre-complexing heregulin or HER3 or by stabilizing complexes of the respective ligand with the heregulin or HER3 receptor (such as stabilizing native complex formed between heregulin and HER3).

The term "heregulin antagonist" or "HER3 antagonist" refers to any molecule that partially or fully blocks, inhibits, or neutralizes a biological activity of heregulin or HER3, respectively, or both heregulin and HER3, and include, but are not limited to, soluble forms of HER3 receptor or such as an extracellular domain sequence of HER3, HER3 receptor fusion proteins, covalently modified forms of HER3 receptor, covalently modified forms of HER3 receptor, HER3 variants, heregulin variants, HER3 receptor antibodies and heregulin antibodies. To determine whether a heregulin antagonist molecule partially or fully blocks, inhibits or neutralizes a biological activity of heregulin or HER3, assays may be conducted to assess the effect(s) of the antagonist molecule on, for example, binding of heregulin to HER3. Such assays may be conducted in known in vitro or in vivo assay formats, for instance, in cells expressing HER3. Preferably, the heregulin antagonist employed in the methods described herein will be capable of blocking or neutralizing at least one type of heregulin activity, which may optionally be determined in assays such as described herein. To determine whether an HER3 antagonist molecule partially or fully blocks, inhibits or neutralizes a biological activity of heregulin or HER3, assays may be conducted to assess the effect(s) of the antagonist molecule on, for example, binding of heregulin to HER3. Such assays may be conducted in known in vitro or in vivo formats, for instance, using cells transfected with HER3. Preferably, the HER3 antagonist employed in the methods described herein will be capable of blocking or neutralizing at least one type of HER3 activity. Optionally, a heregulin antagonist or HER3 antagonist will be capable of reducing or inhibiting binding of heregulin to HER3 by at least 50%, preferably, by at least 90%, more preferably by at least 99%, and most preferably, by 100%, as compared to a negative control molecule, in a binding assay. In one embodiment, the heregulin antagonist or HER3 antagonist will comprise antibodies which will competitively inhibit the binding of heregulin to HER3. Methods for determining antibody specificity and affinity by competitive inhibition are known in the art (see, e.g., Harlow et al., *Antibodies: A Laboratory Manual*, Cold Spring Harbor Laboratory Press, Cold Spring Harbor, N.Y. (1998); Colligan et al., *Current Protocols in Immunology*, Green Publishing Assoc., NY (1992; 1993); Muller, *Meth. Enzym.*, 92:589-601 (1983).

The term "heregulin agonist" or "HER3 agonist" refers to any molecule that partially or fully enhances, stimulates or activates a biological activity of heregulin or HER3, respectively, or both heregulin and HER3, and include, but are not limited to HER3 variant polypeptides and heregulin binding domain specific anti-HER3 receptor antibodies. To determine whether a heregulin agonist molecule partially or fully enhances, stimulates, or activates a biological activity of HER3, assays may be conducted to assess the effect(s) of the agonist molecule on, for example, HER3-expressing or HER3-transfected cells. Such assays may be conducted in known in vitro or in vivo assay formats. Preferably, the heregulin agonist employed in the methods described herein will be capable of enhancing or activating at least one type of heregulin activity, which may optionally be determined in assays such as described herein.

The term "antibody" is used in the broadest sense and specifically covers, for example, single monoclonal antibodies against heregulin and HER3 (e.g. those targeting the heregulin binding domain in HER3), antibody compositions with polyepitopic specificity, single chain antibodies, and fragments of antibodies. "Antibody" as used herein includes intact immunoglobulin or antibody molecules, polyclonal antibodies, multispecific antibodies (i.e., bispecific antibodies formed from at least two intact antibodies) and immunoglobulin fragments (such as Fab, F(ab')$_2$, or Fv), so long as they exhibit any of the desired agonistic or antagonistic properties described herein.

Antibodies are typically proteins or polypeptides which exhibit binding specificity to a specific antigen. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Chothia et al., *J. Mol. Biol.*, 186:651-663 (1985); Novotny and Haber, *Proc. Natl. Acad. Sci. USA*, 82:4592-4596 (1985)). The light chains of antibodies from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called alpha, delta, epsilon, gamma, and mu, respectively.

"Antibody fragments" comprise a portion of an intact antibody, generally the antigen binding or variable region of the intact antibody. Examples of antibody fragments include Fab, Fab', F(ab')2, and Fv fragments, diabodies, single chain antibody molecules, and multispecific antibodies formed from antibody fragments.

The term "variable" is used herein to describe certain portions of the variable domains which differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat, E. A. et al., *Sequences of Proteins of Immunological Interest*, National Institutes of Health, Bethesda, Md. (1987)). The constant domains are not involved directly in binding an antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include chimeric, hybrid and recombinant antibodies produced by splicing a variable (including hypervariable) domain of the antibody of interest with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity or properties. See, e.g. U.S. Pat. No. 4,816,567 and Mage et al., in *Monoclonal Antibody Production Techniques and Applications*, pp. 79-97 (Marcel Dekker, Inc.: New York, 1987).

The term "immunospecific" as used in "immunospecific binding of antibodies" for example, refers to the antigen specific binding interaction that occurs between the antigen-combining site of an antibody and the specific antigen recognized by that antibody.

"Isolated," when used to describe the various proteins disclosed herein, means protein that has been identified and separated and/or recovered from a component of its natural environment. Contaminant components of its natural environment are materials that would typically interfere with diagnostic or therapeutic uses for the protein, and may include enzymes, hormones, and other proteinaceous or non-proteinaceous solutes. In preferred embodiments, the protein will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated protein includes protein in situ within recombinant cells, since at least one component of the protein natural environment will not be present. Ordinarily, however, isolated protein will be prepared by at least one purification step.

"Treatment" or "therapy" refer to both therapeutic treatment and prophylactic or preventative measures.

"Mammal" for purposes of treatment or therapy refers to any animal classified as a mammal, including humans, domestic and farm animals, and zoo, sports, or pet animals, such as dogs, horses, cats, cows, etc. Preferably, the mammal is human.

"HER3-related pathological condition" and "heregulin-related pathological condition" refer to pathologies or conditions associated with abnormal levels of expression or activity of HER3 or heregulin, respectively, in excess of, or less than, levels of expression or activity in normal healthy mammals, where such excess or diminished levels occur in a systemic, localized, or particular tissue or cell type or location in the body. HER3-related pathological conditions and heregulin-related pathological conditions include syndromes characterized by disregulated cell growth such as cancer.

The terms "cancer", "cancerous", and "malignant" refer to or describe the physiological condition in mammals that is typically characterized by unregulated cell growth. Examples of cancer include but are not limited to, carcinoma including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, cervical cancer, ovarian cancer, liver cancer such as hepatic carcinoma and hepatoma, bladder cancer, breast cancer, colon cancer, colorectal cancer, endometrial carcinoma, myeloma (such as multiple myeloma), salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer. Optionally, the cancer will express, or have associated with the cancer cell, heregulin or HER3. By way of example, breast and ovarian cancers are among the cancers reported in the literature to express HER3.

II. Methods and Materials

The disclosure provided herein teaches that the EGF-like domain of heregulin (hrg) binds to domains I and II of HER3, in contrast to the EGF receptor, for which prior studies have shown that a construct consisting of domains III and portions of domain IV binds EGF. As illustrated in Example 2, a hrg binding site is identified by limited proteolysis of the recombinant extracellular domains of HER3 (HER3-ECD$^{I-IV}$) in both the presence and absence of hrg. In the absence of hrg, HER3-ECD$^{I-IV}$ is cleaved after position Tyr$^{50}$, near the beginning of domain I. Binding of hrg to HER3-ECD$^{I-IV}$ fully protects position Tyr$^{50}$ from proteolysis. To confirm that domain I contains a hrg binding site, a HER3 polypeptide comprising only domains I and II (and not domains III and IV) of HER3 (HER3-ECD$^{I-II}$) was generated. This HER3-ECD$^{I-II}$ polypeptide was then shown to bind hrg with 68 nM affinity. These data provide evidence that domains I and II of HER3-ECD$^{I-IV}$ act as a functional unit in folding and binding of hrg.

The biochemical findings reinforce the structural hypothesis that HER3-ECD$^{I-IV}$ is similar to the insulin-like growth factor-1 receptor (IGF-1R), as follows: 1) The protected cleavage site in HER3-ECD$^{I-IV}$ corresponds to a binding footprint in domain I of IGF-1R; 2) HER3-ECD$^{I-II}$ binds hrg with a 68 nM dissociation constant, supporting the hypothesis that domain I is involved in ligand binding; and 3) the large accessible surface area (1749 Å) of domain L1 of IGF-1R that is buried by domain S1, as well as the presence of conserved contacts in this interface of type 1 RTKs, provide evidences that domains L1 and S1 of IGF-1R function as a unit as observed for HER3-ECD$^{I-II}$. The results are consistent with a model wherein HER3 has a structure similar to IGF-1R and binds ligand at a site in corresponding domains.

In this context, the invention provides methods and materials for identifying molecules which bind to the heregulin binding site on HER3 as well as methods and materials for modulating heregulin and/or HER3 activity in mammalian cells. Typical methods for modulating heregulin and/or HER3 activity in mammalian cells comprise exposing the cells to a desired amount of antagonist or agonist that affects heregulin interaction with HER3. Preferably, the amount of antagonist or agonist employed will be an amount effective to affect the binding and/or activity of the respective ligand or respective receptor to achieve a therapeutic effect. This can be accomplished in vivo or ex vivo in accordance, for instance, with the methods described below and in the Examples. An exemplary condition or disorders to be treated with such antagonists or antagonists is a cancer whose malignant phenotype is associated with aberrant HER3 or heregulin expression.

Diagnostic methods are also provided herein. For instance, the antagonists or agonists may be employed to detect the respective binding partner (heregulin and HER3) or in mammals known to be or suspected of having a heregulin-related pathological condition or HER3-related pathological condition. The antagonist or agonist molecule may be used, e.g., in immunoassays to detect or quantitate heregulin or HER3 in a sample. A sample, such as cells obtained from a mammal, can be incubated in the presence of a labeled antagonist or agonist molecule, and detection of the labeled antagonist or agonist bound in the sample can be performed. Such assays, including various clinical assay procedures, are known in the art.

The antagonists and agonists which can be employed in the methods include, but are not limited to, soluble forms of HER3 receptor, HER3 receptor immunoadhesins, fusion proteins comprising HER3, covalently modified forms of heregulin and HER3, HER3 receptor variants anti-HER3 receptor antibodies that target the heregulin binding domain, and anti-heregulin antibodies that target the HER3 binding domain. Various techniques that can be employed for making the antagonists and agonists are described herein.

A. HER3 Polypeptides

The disclosure provided herein includes HER3 polypeptides such as the HER3-ECD$^{I-II}$ polypeptide discussed above as well as HER3 substitution variants such as those having an amino acid substitution at residue E64 and/or V110. The description below provides typical schemes for the production of HER3 polypeptides including HER3 polypeptide variants, by culturing cells transformed or transfected with a vector containing HER3 polypeptide encoding nucleic acid. It is, of course, contemplated that alternative methods, which are well known in the art, may be employed to prepare HER3 polypeptides. For instance, the HER3 polypeptide sequence, or portions thereof, may be produced by direct peptide synthesis using solid-phase techniques (see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)). In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of HER3 polypeptides may be chemically synthesized separately and combined using chemical or enzymatic methods to produce a full-length HER3 polypeptide.

This disclosure identifies amino acids in discontinuous segments in domain I of HER3 which appear to be critical for heregulin binding (see, e.g. Table 3). For example, a mutation at residue 64 appears to decrease all binding affinity in both recombinant HER3$^{I-IV\ E64A}$ and HER3$^{I-II\ E64A}$; while a mutation of V110A in and HER3$^{I-II}$ causes a 4 fold increase in heregulin binding affinity. Residues 64 and 110 are in domain I of HER3 and map to residues H30 and L81 in the hormone binding footprint in the IGF-1R. Residues H30 and L81 lie on different strands in IGF-1R, but are within 12A of each other. HER3 V110 and hrg V180 could form hydrophobic interactions, and HER3 E64 and hrg H178 could form a salt bridge with heregulin. These specific interactions could be disrupted by the mutations of E64A and V110A in HER3 as we observed in our biochemical experiments.

A preferred embodiment of the invention is a HER3 variant polypeptide comprising an amino acid sequence which differs from the native sequence HER3 polypeptide sequence of SEQ ID NO: 2 and has one or more of amino acid substitutions at the following residue position(s) in SEQ ID NO: 2: E43; N44; K51; E64; V66; and V110. Typically, the variant binds heregulin with an affinity different from a HER2 polypeptide that has no amino acid substitution at the enumerated position(s). Another preferred embodiment of the invention is a HER3 variant polypeptide comprising an amino acid sequence which differs from the native sequence HER3 polypeptide sequence of SEQ ID NO: 2 and has one or more of amino acid substitutions at the residue positions identified in Table 3. Another embodiment of the invention is a non-naturally occurring HER3 variant polypeptide consisting essentially of amino acid 20 to amino acid 329 of HER3 polypeptide sequence of SEQ ID NO: 2; wherein the HER3 variant polypeptide specifically binds to the heregulin polypeptide of SEQ ID NO: 4 and exhibits an impaired ability to interact with the HER2 polypeptide of SEQ ID NO: 6. Related embodiments of this invention include an isolated nucleic acid comprising a nucleotide sequence encoding these HER3 variants, vectors comprising nucleic acids encoding these variants and host cells (e.g. *E. coli*) containing these vectors. Another related embodiment of the invention is a method of making HER3 variant polypeptide by providing a host cell comprising a vector encoding a HER3 variant, providing culture media, culturing the host cell in the culture media under conditions sufficient to express the HER3 variant polypeptide, recovering the HER3 variant polypeptide from the host cell or culture media, and then purifying the HER3 variant polypeptide. Optionally the HER3 variant polypeptide is conjugated or linked to one or more polyol groups.

The HER3 variants disclosed herein have a number of uses, and can, for example, be used to elucidate the signalling mechanisms of the heregulin/HER2/HER3 complex, a complex which, as noted above, is implicated in the malignant phenotype of certain cancers such as breast and ovarian cancers. Specifically, as noted herein, the molecules of the heregulin/HER2/HER3 complex contain different domains having different functional properties including an ability to associate in HER3 homo-oligomers as well as HER2/HER3 hetero-oligomers. The HER2/HER3 hetero-oligomers associated with heregulin produce a functional signalling complex that is associated with the biological activity of the molecules. Consequently, the variants disclosed herein which are designed to target a HER3 domain that binds to heregulin and to, for example, bind with a greater or lesser affinity to heregulin, can be used to assess interaction between HER2 and HER3 as well as the interaction between heregulin and HER2 and HER3. As is known in the art, the elucidation of structural domains associated with biological activities and the signalling mechanisms of molecules that are associated with pathologies such as cancer is a crucial step in the identification of novel diagnostic and therapeutic methods and materials (e.g. heregulin agonists and antagonists) which can be used to treat such pathologies.

Figure 9:
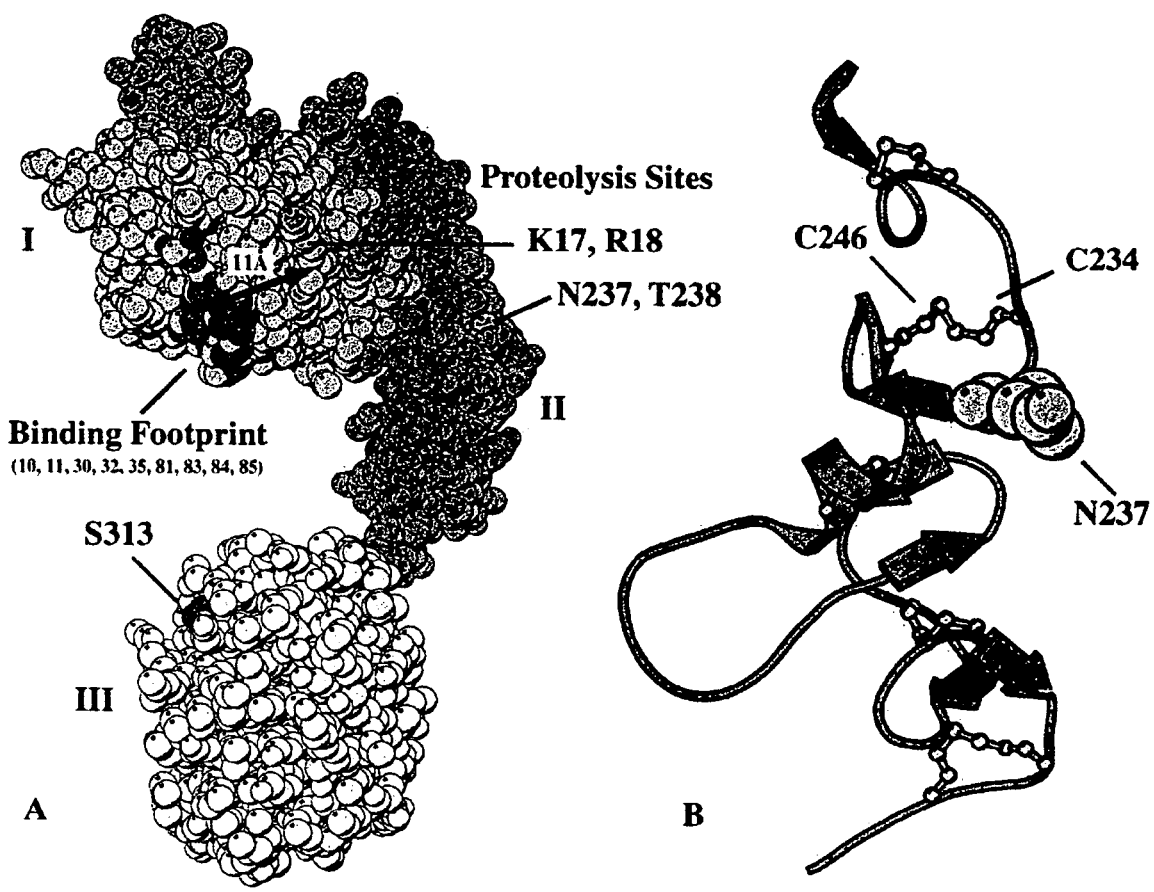
FIG. 9. Structural similarity of IGF-1R to HER3-ECD$^{I-IV}$. A, space-filling model of domains I and II of the structure of IGF-1R (43) showing the positions of the proteolysis sites (red) observed for the HER3-ECD$^{I-IV}$ mapped to the IGF-1R structure. The position of mutations (dark blue) that decrease ligand binding in IR are also mapped to a binding footprint in the IGF-1R structure. Domain L1 is light blue, and L2 is lavender in IGF-1R (domains I and III in HER3-ECD$^{I-IV}$), and domain S1 (domain II in HER3-ECD$^{I-II}$) is green. 1740 Å$^2$ of accessible surface area in domain L1 are buried by domain S1 in IGF-1R. The cleavage site at position 50 in HER3-ECD$^{I-IV}$ that is protected by hrg (position 18 in IGF-1R) lies on the same face of domain L1 in IGF-1R and is 11 Å away from residue 10 in the binding footprint of IR/IGF-1R. The unprotected cleavage site at position 270 in HER3-ECD$^{I-IV}$ (position 237 in IGF-1R) lies in domain II, is on the opposite side as the binding footprint, and is 40 Å away from the binding footprint. Residue numbers are shown in the binding footprint. The cleavage site that is protected by hrg in HER3-ECD$^{I-IV}$ is near the binding footprint in domain L1 of IGF-1R. B, backbone representation of domain II of IGF-1R showing the position of the proteolysis site at position 270 in HER3-ECD$^{I-IV}$ (red cpk) (position 237 in IGF-1R) superimposed on the IGF-1R structure. The chain remains connected by a disulfide (red ball and stick) when cleavage occurs at position 270. The disulfide bridge connecting fragments I and II of HER3-ECD$^{I-IV}$ is consistent with a structural model based on IR/IGF-1R.

In this regard, the disclosure provides evidence that a specific subset of amino acid residues in the HER3 polypeptide are likely to be involved in the interaction with heregulin (and consequently can be mutated in studies designed to characterize the Her2, HER3 and heregulin interactions). The data providing this evidence includes a number of independent and complementary observations including: (1) sequence comparison with residues in the structurally homologous IGF-1R molecule that are known to be associated with ligand binding (see, e.g. FIG. 8); (2) crystallographic studies to map a heregulin binding footprint in HER3 (see, e.g. FIG. 9); and (3) the further limitation of this subset to those residues that are most likely exposed to the solvent environment and therefore likely to interact with heregulin.

For example, certain residues were chosen for mutation based on their proximity to the proteolysis site in domain I of HER3 (see, e.g. Singer et al. (2001) *J Biol Chem* 276(47), 44266-74), conservation to equivalent residues which are critical for ligand binding in the IR (see, e.g. Williams et al. (1995) *J Biol Chem* 270(7), 3012-6) and in the hormone binding footprint in the IGF-1R (see, e.g. Garrett et al. (1998) *Nature* 394(6691), 395-9) based on a multiple sequence alignment performed between HER3, IR and IGF-1R. As noted above, this subset of HER3 residues includes those shown in Tables 2 and 3. The specific results obtained with the examination of members of this subset of HER3 residues (e.g. V110 and E64) provides further evidence that the members of this specific subset of amino acid residues in the HER3 polypeptide are involved in the interaction with heregulin.

The HER3 variants disclosed herein include those where the wild type amino acid residue at one of the enumerated positions is substituted with any one of the other 19 naturally occurring amino acids. As is known in the art, there is a reasonable expectation that a substitution at a wild type residue identified as likely to control affinity (for example residue 110) will effect the affinity of the HER3 variant for heregulin. Specifically, the pertinent art teaches that in situations where an experimental analysis has established that the properties of a specific residue at a particular position within the polypeptide chain are likely involved in maintaining some aspect of a protein's functional integrity, an alteration in the size, shape, charge, hydrogen-bonding capacity or chemical reactivity of the amino acid side chain at one of these "active" amino acid positions is likely to affect the function of the protein in some way For this reason, the skilled artisan would reasonably expect a perturbation in a HER3 residue likely to control the affinity of HER3 for heregulin to effect the affinity of HER3 for heregulin.

The invention further provides recombinant DNA or RNA molecules containing a HER3 polynucleotide, fragment, variant thereof, including but not limited to phages, plasmids, phagemids, cosmids, YACs, BACs, as well as various viral and non-viral vectors well known in the art, and cells transformed or transfected with such recombinant DNA or RNA molecules. Methods for generating such molecules are well known (see, for example, Sambrook et al, 1989, supra). The invention further provides a host-vector system comprising a recombinant DNA molecule containing a HER3 polynucleotide, fragment, variant thereof within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include a number of mammalian cells routinely used for the expression of recombinant proteins (e.g., COS, CHO, 293, 293T cells). More particularly, a polynucleotide comprising the coding sequence of HER3 or a fragment, variant thereof can be used to generate HER3 proteins or fragments thereof using any number of host-vector systems routinely used and widely known in the art.

A wide range of host-vector systems suitable for the expression of HER3 proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). The host-vector systems of the invention are useful for the production of a HER3 protein or fragment thereof. Such host-vector systems can be employed to study the functional properties of HER3 and HER3 mutations or analogs.

Recombinant human HER3 protein can be produced by mammalian cells transfected with a construct encoding a HER3 nucleotide. For example, 293T cells can be transfected with an expression plasmid encoding HER3 or fragment, variant thereof, the HER3 or related protein is expressed in the 293T cells, and the recombinant HER3 protein is isolated using standard purification methods (e.g., affinity purification using anti-HER3 antibodies). In another embodiment, a HER3 coding sequence is subcloned into the retroviral vector pSRαMSVtkneo and used to infect various mammalian cell lines, such as NIH 3T3, COS, CHO and MCF-7 in order to establish HER3 expressing cell lines. Various other expression systems well known in the art can also be employed. Expression constructs encoding a leader peptide joined in frame to the HER3 coding sequence can be used for the generation of a secreted form of recombinant HER3 protein.

As discussed herein, redundancy in the genetic code permits variation in HER3 gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, *Mol. Cell Biol.*, 9:5073-5080 (1989).

Embodiments of the invention disclosed herein include a wide variety of art-accepted variants of HER3 proteins such as polypeptides having amino acid insertions, deletions and substitutions. HER3 variants can be made using methods known in the art such as site-directed mutagenesis, alanine scanning, and PCR mutagenesis. Site-directed mutagenesis (Carter et al., *Nucl. Acids Res.*, 13:4331 (1986); Zoller et al., *Nucl. Acids Res.*, 10:6487 (1987)), cassette mutagenesis (Wells et al., Gene, 34:315 (1985)), restriction selection mutagenesis (Wells et al., *Philos. Trans. R. Soc. London SerA*, 317:415 (1986)) or other known techniques can be performed on the cloned DNA to produce the HER3 variant DNA.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins*, (W.H. Freeman & Co., N.Y.); Chothia, J. Mol. Biol., 150:1 (1976)). If alanine substitution does not yield adequate amounts of variant, an isosteric amino acid can be used.

HER3 proteins can be generated using standard peptide synthesis technology or using chemical cleavage methods well known in the art. Alternatively, recombinant methods can be used to generate nucleic acid molecules that encode a HER3 protein. In one embodiment, nucleic acid molecules provide a means to generate defined fragments of the HER3 protein (or variants thereof).

Modifications of HER3 proteins such as covalent modifications are included within the scope of this invention. One type of covalent modification includes reacting targeted amino acid residues of a HER3 polypeptide with an organic derivatizing agent that is capable of reacting with selected side chains or the N- or C-terminal residues of the HER3. Another type of covalent modification of the HER3 polypeptide included within the scope of this invention comprises altering the native glycosylation pattern of a protein of the invention. Another type of covalent modification of HER3 comprises linking the HER3 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

B. Antibodies

It is contemplated that anti-HER3 receptor antibodies that specifically target the heregulin binding domain in HER3 may also be employed in the presently disclosed methods. Examples of such molecules include neutralizing or blocking antibodies which can preferably inhibit binding of heregulin to HER3 receptors. The anti-HER3 antibodies may be monoclonal antibodies.

Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include a HER3 polypeptide or a fusion protein thereof, such as a HER3 ECD-IgG fusion protein. The immunizing agent may alternatively comprise a fragment or portion of HER3 having one or more amino acids that participate in the binding of HER3 to heregulin. In a preferred embodiment, the immunizing agent comprises an extracellular domain sequence of HER3 fused to an IgG sequence.

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

C. Methods of Screening Molecules that Bind to the Heregulin Binding Site in HER3

The invention also encompasses methods of screening molecules to identify those which can act as agonists or antagonists of the heregulin/HER3 interaction. Such molecules may comprise small molecules or polypeptides, including antibodies. Examples of small molecules include, but are not limited to, small peptides or peptide-like molecules, preferably soluble peptides, and synthetic non-peptidyl organic or inorganic compounds. The screening assays for drug candidates are designed to identify compounds or molecules that bind or complex with the ligand or receptor polypeptides identified herein, or otherwise interfere with the interaction of these polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art. Assays for, for instance, antagonists are common in that they call for contacting the drug candidate with a ligand or receptor polypeptide identified herein under conditions and for a time sufficient to allow these two components to interact.

In binding assays, the interaction is binding and the complex formed can be isolated or detected in the reaction mixture. In a particular embodiment, a preferred receptor polypeptide identified herein (e.g. HER3 polypeptide having only domains I and II) or the drug candidate is immobilized on a solid phase, e.g., on a microtiter plate, by covalent or non-covalent attachments. Non-covalent attachment generally is accomplished by coating the solid surface with a solution of the ligand or receptor polypeptide and drying. Alternatively, an immobilized antibody, e.g., a monoclonal antibody, specific for the ligand or receptor polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular ligand or receptor polypeptide identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989); Chien et al., *Proc. Natl. Acad. Sci. USA,* 88:9578-9582 (1991)) as disclosed by Chevray and Nathans, *Proc. Natl. Acad. Sci. USA,* 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds or molecules that interfere with the interaction of a ligand or receptor polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the ligand or receptor polypeptide may be added to a cell along with the compound to be screened for a particular activity and the ability of the compound to inhibit the activity of interest in the presence of the ligand or receptor polypeptide indicates that the compound is an antagonist to the ligand or receptor polypeptide. Alternatively, antagonists may be detected by combining the ligand or receptor polypeptide and a potential antagonist with membrane-bound polypeptide receptors or recombinant receptors under appropriate conditions for a competitive inhibition assay. The ligand or receptor polypeptide can be labeled, such as by radioactivity, such that the number of polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.*, 1(2): Chapter 5 (1991). Preferably, expression cloning is employed wherein polyadenylated RNA is prepared from a cell responsive to the ligand or receptor polypeptide and a cDNA library created from this RNA is divided into pools and used to transfect COS cells or other cells that are not responsive to the ligand or receptor polypeptide. Transfected cells that are grown on glass slides are exposed to labeled ligand or receptor polypeptide. The ligand or receptor polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach, labeled ligand polypeptide can be photoaffinity-linked with cell membrane or extract preparations that express receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

A representative embodiment of this invention comprises a method of screening for a molecule that interacts with the heregulin binding domain in HER3 ("HER3 heregulin binding domain") comprising the steps of contacting a population of molecules with a polypeptide comprising the HER3 heregulin binding domain, allowing the population of molecules and the HER3 heregulin binding domain to interact under conditions that facilitate an interaction, determining the presence of a molecule that interacts with the HER3 heregulin binding domain, and then separating molecules that do not interact with the HER3 heregulin binding domain from molecules that do. In a specific embodiment, the method further comprises purifying a molecule that interacts with the HER3 heregulin binding domain. The identified molecule can be used to modulate a function performed by HER3. This embodiment of the invention is well suited to screen chemical libraries for molecules which modulate, e.g., inhibit, antagonize, or agonize or mimic, the activity of HER3 as measured by one of the assays disclosed herein or known in the art (see, e.g. Aigular et al., (1999) Oncogene 18, 6050-6062). The chemical libraries can be peptide libraries, peptidomimetic libraries, chemically synthesized libraries, recombinant, e.g., phage display libraries, and in vitro translation-based libraries, other non-peptide synthetic organic libraries.

Exemplary libraries are commercially available from several sources (ArQule, Tripos/PanLabs, ChemDesign, Pharmacopoeia). In some cases, these chemical libraries are generated using combinatorial strategies that encode the identity of each member of the library on a substrate to which the member compound is attached, thus allowing direct and immediate identification of a molecule that is an effective modulator. Thus, in many combinatorial approaches, the position on a plate of a compound specifies that compound's composition. Also, in one example, a single plate position may have from 1-20 chemicals that can be screened by administration to a well containing the interactions of interest. Thus, if modulation is detected, smaller and smaller pools of interacting pairs can be assayed for the modulation activity. By such methods, many candidate molecules can be screened.

Many diversity libraries suitable for use are known in the art and can be used to provide compounds to be tested according to the present invention. Alternatively, libraries can be constructed using standard methods. Chemical (synthetic) libraries, recombinant expression libraries, or polysome-based libraries are exemplary types of libraries that can be used.

In one embodiment, one can screen peptide libraries to identify molecules that interact with HER3 heregulin binding domain protein sequences. In such methods, peptides that bind to the HER3 heregulin binding domain are identified by screening libraries that encode a random or controlled collection of amino acids. Peptides encoded by the libraries are expressed as fusion proteins of bacteriophage coat proteins, the bacteriophage particles are then screened against the protein of interest.

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with HER3 heregulin binding domain sequences are disclosed for example in U.S. Pat. No. 5,723,286 issued 3 Mar. 1998 and 5,733,731 issued 31 Mar. 1998.

Small molecules and ligands that interact with HER3 heregulin binding domain can be identified through related embodiments of such screening assays. For example, small molecules can be identified that interfere with protein function, including molecules that interfere with the tyrosine kinase activity associated with HER3.

A typical embodiment is a method of identifying a compound which specifically binds the HER3 heregulin binding domain, comprising the steps of contacting the HER3 heregulin binding domain with a test compound under conditions favorable to binding; and then determining whether said test compound binds to said HER3 heregulin binding domain so that a compound which binds to said domain can be identified. As the interaction between various receptor tyrosine kinases and a variety of test compounds have been previously described, skilled artisans are familiar with the conditions conducive to binding. A specific embodiment of this aspect of the invention includes the steps of transfecting cells with a construct encoding HER3, contacting said cells with said test compound that is tagged or labelled with a detectable marker and then analyzing said cells for the presence bound test compound. In contexts where the transfected cells are observed to preferentially bind the test compound as compared to cells that have not been transfected with a HER3 construct, this indicates that the test compounds is binding to the HER3 protein expressed by those cells.

A test compound which binds said HER3 heregulin binding domain may then be further screened for the inhibition of a biological activity (e.g. tyrosine kinase activity) associated with HER3. Such an embodiment includes, for example determining whether said test compound inhibits the tyrosine kinase activity associated with HER3 by utilizing molecular biological protocols to create recombinant contracts whose enzymological and biological properties can be examined directly. Enzymology is performed for example, by measuring tyrosine kinase activity in vitro or in HER3 expressing cells using standard assays.

D. Assay Methods

Diagnostic methods are also provided herein. For instance, the antagonists or agonists may be employed to detect HER3 and/or heregulin in mammals known to be or suspected of having a HER3 and/or heregulin related pathological condition. The antagonist or agonist molecule may be used, e.g., in immunoassays to detect or quantitate heregulin and/or HER3 in a sample. A sample, such as cells obtained from a mammal, can be incubated in the presence of a labeled antagonist or agonist molecule, and detection of the labeled antagonist or agonist bound in the sample can be performed. Such assays, including various clinical assay procedures, are known in the art, for instance as described in Voller et al., *Immunoassays*, University Park, 1981.

Ligand/receptor binding studies may be carried out in any known assay method, such as competitive binding assays, direct and indirect sandwich assays, and immunoprecipitation assays. Cell-based assays and animal models can be used as diagnostic methods and to further understand the interaction between the ligands and receptors identified herein and the development and pathogenesis of the conditions and diseases referred to herein.

In one approach, mammalian cells may be transfected with the ligands or receptors described herein, and the ability of the agonists or antagonists to stimulate or inhibit binding or activity is analyzed. Suitable cells can be transfected with the desired gene, and monitored for activity. Such transfected cell lines can then be used to test the ability of antagonist(s) or agonist(s) to inhibit or stimulate, for example, to modulate B-cell proliferation or Ig secretion. Cells transfected with the coding sequence of the genes identified herein can further be used to identify drug candidates for the treatment of immune related diseases or cancer.

In addition, primary cultures derived from transgenic animals can be used in the cell-based assays. Techniques to derive continuous cell lines from transgenic animals are well known in the art. (see, e.g., Small et al., *Mol. Cell. Biol.* 5:642-648 (1985)).

E. Formulations

The HER3 antagonists or agonists described herein, are optionally employed in a carrier. Suitable carriers and their formulations are described in *Remington's Pharmaceutical Sciences*, 16th ed., 1980, Mack Publishing Co., edited by Osol et al. Typically, an appropriate amount of a pharmaceutically-acceptable salt is used in the carrier to render the formulation isotonic. Examples of the carrier include saline, Ringer's solution and dextrose solution. The pH of the carrier is preferably from about 5 to about 8, and more preferably from about 7.4 to about 7.8. It will be apparent to those persons skilled in the art that certain carriers may be more preferable depending upon, for instance, the route of administration and concentration of active agent being administered. The carrier may be in the form of a lyophilized formulation or aqueous solution.

Acceptable carriers, excipients, or stabilizers are preferably nontoxic to cells and/or recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; and/or non-ionic surfactants such as TWEEN™, PLURONICS™ or polyethylene glycol (PEG).

The formulation may also contain more than one active compound as necessary for the particular indication being treated, preferably those with complementary activities that do not adversely affect each other.

The HER3 antagonist or agonist described herein, may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in *Remington's Pharmaceutical Sciences* 16th edition, Osol, A. Ed. (1980).

The formulations to be used for in vivo admininstration should be sterile. This is readily accomplished by filtration through sterile filtration membranes. Sustained-release preparations may be prepared. Suitable examples of sustained-release preparations include semipermeable matrices of solid hydrophobic polymers containing the active agent, which matrices are in the form of shaped articles, e.g. films, or microcapsules. Examples of sustained-release matrices include polyesters, hydrogels (for example, poly(2-hydroxy-ethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

Related embodiments of the invention include methods for the preparation of a medication for the treatment of pathological conditions including cancer by preparing a HER3 variant polypeptide (e.g. a variant having a substitution at V110) composition for administration to a mammal having the pathological condition. A related method is the use of an effective amount of a HER3 variant polypeptide in the preparation of a medicament for the treatment of cancer. Such methods typically involve the steps of including an amount of HER3 variant polypeptide sufficient to inhibit the interaction of heregulin and HER3 in vivo and an appropriate amount of a physiologically acceptable carrier. As is known in the art, optionally other agents can be included in these preparations.

F. Modes of Therapy

The invention further provides methods for modulating HER3, and/or heregulin activity in mammalian cells which comprise exposing the cells to a desired amount of antagonist or agonist that affects heregulin interaction with HER3. Preferably, the amount of antagonist or agonist employed will be an amount effective to affect the binding and/or activity of the respective ligand or respective receptor to achieve a therapeutic effect. This can be accomplished in vivo or ex vivo in accordance, for instance, with the methods described below. Exemplary conditions or disorders to be treated with HER3 agonists or heregulin agonists include cancer such as those associated with an aberrant expression of HER3 and/or heregulin.

The molecules described herein are useful in treating various pathological conditions, such as cancer. These conditions can be treated by stimulating or inhibiting a selected activity associated with heregulin or HER3 in a mammal through, for example, administration of one or more antagonists or agonists described herein.

Diagnosis in mammals of the various pathological conditions described herein can be made by the skilled practitioner. Diagnostic techniques are available in the art which allow, e.g., for the diagnosis or detection of cancer or immune related disease in a mammal. For instance, cancers may be identified through techniques, including but not limited to, palpation, blood analysis, x-ray, NMR and the like.

The antagonist(s) or agonist(s) can be administered in accord with known methods, such as intravenous administration as a bolus or by continuous infusion over a period of time, by intramuscular, intraperitoneal, intracerebrospinal, subcutaneous, intra-articular, intrasynovial, intrathecal, oral, topical, or inhalation routes. Optionally, administration may be performed through mini-pump infusion using various commercially available devices. The antagonists or agonists may also be employed using gene therapy techniques which have been described in the art. Effective dosages and schedules for administering antagonists or agonists may be determined empirically, and making such determinations is within the skill in the art. Single or multiple dosages may be employed. It is presently believed that an effective dosage or amount of antagonist or agonist used alone may range from about 1 ng/kg to about 100 mg/kg of body weight or more per day. Interspecies scaling of dosages can be performed in a manner known in the art, e.g., as disclosed in Mordenti et al., *Pharmaceut. Res.*, 8:1351 (1991).

As noted above, the HER3 polypeptides, HER3 polypeptide variants, HER3 polypeptide fragments, HER3 polynucleotides encoding said polypeptides, variants and fragments, and the HER3 agents useful in the methods of the invention can be incorporated into pharmaceutical compositions suitable for administration into a mammal. Such compositions typically comprise at least one HER3 polypeptide, HER3 polypeptide variant, HER3 polypeptide fragment, HER3 polynucleotide encoding said polypeptide, variant or fragment, an HER3 agent, or a combination thereof, and a pharmaceutically acceptable carrier. Methods for formulating the HER3 compounds of the invention for pharmaceutical administration are known to those of skill in the art. See, for example, Remington: The Science and Practice of Pharmacy, 19$^{th}$ Edition, Gennaro (ed.) 1995, Mack Publishing Company, Easton, Pa.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the, invention is formulated to be compatible with its intended route of administration.

The pharmaceutical compositions of the invention, comprising HER3 polypeptides, HER3 polypeptide variants, HER3 polypeptide fragments, polynucleotides encoding said HER3 polypeptides, variants and fragments, as well as HER3 agents, as defined above, are administered in therapeutically effective amounts. The "therapeutically effective amount" refers to a nontoxic dosage level sufficient to induce a desired biological result (e.g. a diminution of the severity of the symptoms associated with a pathological condition such as breast or ovarian cancer). Amounts for administration may vary based upon the desired activity, the diseased state of the mammal being treated, the dosage form, method of administration, patient factors such as age, sex, and severity of disease. It is recognized that a therapeutically effective amount is provided in a broad range of concentrations. Such range can be determined based on in vitro and/or in vivo assays.

Therapeutic compositions of the HER3 can be prepared by mixing the desired HER3 molecule having the appropriate degree of purity with optional pharmaceutically acceptable carriers, excipients, or stabilizers (*Remington's Pharmaceutical Sciences,* 16th edition, Osol, A. ed. (1980)), in the form of lyophilized formulations, aqueous solutions or aqueous suspensions. Acceptable carriers, excipients, or stabilizers are preferably nontoxic to recipients at the dosages and concentrations employed, and include buffers such as Tris, HEPES, PIPES, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; sugars such as sucrose, mannitol, trehalose or sorbitol; salt-forming counter-ions such as sodium; and/or non-ionic surfactants such as TWEEN™, PLURONICS™ or polyethylene glycol (PEG).

Additional examples of such carriers include ion exchangers, alumina, aluminum stearate, lecithin, serum proteins, such as human serum albumin, buffer substances such as glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, colloidal silica, magnesium trisilicate, polyvinyl pyrrolidone, and cellulose-based substances. Carriers for topical or gel-based forms include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations.

Solutions or suspensions used for administering HER3 can include the following components: a sterile diluent such as water for injection, saline solution; fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates and agents for the adjustment of tonicity such as sodium chloride or dextrose. In one embodiment, a pharmaceutical composition can be delivered via slow release formulation or matrix comprising HER3 protein or DNA constructs suitable for expression of HER3 protein into or around a site within the body.

HER3 can also be administered in the form of a variety of sustained-release preparations. For example, HER3 may be delivered to the lung for slow release via encapsulation or carrier materials such as liposomes, or other drug "shells" such as albumin (Albunex by Molecular Biosystems), sugars (Levovist by Schering), gelatins, or lipids. Other suitable examples of sustained-release preparations for use with polypeptides including semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.,* 15: 167-277 (1981) and Langer, *Chem. Tech.,* 12: 98-105 (1982) or poly(vinylalcohol)), polylactides (U.S. Pat. No. 3,773,919, EP 58,481), copolymers of L-glutamic acid and gamma ethyl-L-glutamate (Sidman et al., *Biopolymers,* 22: 547-556 (1983)), non-degradable ethylene-vinyl acetate (Langer et al., supra), degradable lactic acid-glycolic acid copolymers such as the Lupron Depot (injectable microspheres composed of lactic acid-glycolic acid copolymer and leuprolide acetate), and poly-D-(−)-3-hydroxybutyric acid (EP 133,988).

The route of administration may vary depending on the desired effect and/or outcome. Generally for initiation of an HER3 mediated response, introduction of the HER3 at or near the desired site of response is utilized. Alternatively additional routes of administration, such as a systemic administration of HER3, may be employed. Examples of routes of administration include parenteral, e.g., intravenous, intradermal, intramuscular, subcutaneous, oral (e.g., inhalation) transdermal (topical), transmucosal (e.g. a nasal spray), and rectal administration. The HER3 polypeptide may also be administered by perfusion techniques, such as isolated tissue perfusion, to exert local therapeutic effects. Solutions or suspensions used for parenteral, intradermal, or subcutaneous application can include the following components: a sterile diluent such as water for injection, saline solution; fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates and agents for the adjustment of tonicity such as sodium chloride or dextrose. Regimens of administration may vary. A single dose or multiple doses of the agent may be used. Such regimens can vary depending on the severity of the disease and the desired outcome. Following administration of a HER3 polypeptide to the mammal, the mammal's physiological condition can be monitored in various ways well known to the skilled practitioner familiar with the pathological condition to be treated (e.g. breast or ovarian cancer).

It is contemplated that yet additional therapies may be employed in the methods. The one or more other therapies may include but are not limited to, administration of radiation therapy, cytokine(s), growth inhibitory agent(s), chemotherapeutic agent(s), cytotoxic agent(s), tyrosine kinase inhibitors, ras farnesyl transferase inhibitors, angiogenesis inhibitors, and cyclin-dependent kinase inhibitors which are known in the art and defined further with particularity in Section I above. In addition, therapies based on therapeutic antibodies that target tumor antigens such as Rituxan™ or Herceptin™ as well as anti-angiogenic antibodies such as anti-VEGF.

Preparation and dosing schedules for chemotherapeutic agents may be used according to manufacturers' instructions or as determined empirically by the skilled practitioner. Preparation and dosing schedules for such chemotherapy are also described in *Chemotherapy Service* Ed., M. C. Perry, Williams & Wilkins, Baltimore, Md. (1992). The chemotherapeutic agent may precede, or follow administration of, e.g. an antagonist, or may be given simultaneously therewith. The antagonist, for instance, may also be combined with an anti-oestrogen compound such as tamoxifen or an anti-progesterone such as onapristone (see, EP 616812) in dosages known for such molecules.

G. Articles of Manufacture

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agents in the composition may comprise antagonist(s) or agonist(s). The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

H. Brief Characterization of Aspects of the Invention

As disclosed herein, the predominant ligand binding site for heregulin is located in domain I of HER3. The disclosure identifies two proteolytic sites in HER3-ECD$^{I-IV}$ at positions 50 and 270. Cleavage at position 50 is fully protected by hrg binding, whereas position 270 is unprotected. Hrg protection at position 50 is a result of the specific interaction between hrg and HER3-ECD$^{I-IV}$. Only two fragments were detected by SDS-PAGE and mass spectrometry. The N-terminal fragment generated from cleavage at residue 50 could not be detected, but its absence could be due to additional cleavage sites between residues 20 and 50. The cleavage site at position 270 is not protected by hrg, but the fragments generated by this cleavage are held together by disulfide bonds. Hrg protects only one of the cleavage sites in a ligand-specific manner. The extreme C terminus is also sensitive to proteolysis, which could be blocked by an antibody against the V-5 epitope tag but not by hrg.

This protection at position 50 can be explained in two different ways, which include binding of hrg at or near position 50 or indirect protection resulting from a conformational change in HER3-ECD$^{I-IV}$, induced by hrg binding. In order to distinguish between these two possibilities based on the results of the proteolysis experiments; we expressed domain I and II of HER3-ECD$^{I-IV}$ (HER3-ECD$^{I-II}$) and assayed it for binding.

As illustrated in the Examples below, HER3-ECD$^{I-II}$ polypeptide is able to bind heregulin and the association state and binding properties of HER3-ECD$^{I-II}$ were characterized. For example, HER3-ECD$^{I-II}$ is shown to be a monomer and remains in a monomeric state when hrg is present. This is in contrast to the HER3-ECD$^{I-IV}$ expressed in S2 cells in which hrg reverses oligomerization to form a monomer (see, e.g. Landgraf, R., and Eisenberg, D. (2000) Biochemistry 39, 8503-8511). As discussed below we analyzed direct hrg binding to HER3-ECD$^{I-II}$ and qualitatively demonstrated specific binding to hrg binding by a pull-down assay. An equilibrium dissociation constant of 68 nM for hrg binding was calculated by surface plasmon resonance in which the trx-hrg was immobilized. HER3-ECD$^{I-II}$ has 30-fold lower binding affinity than HER3-ECD$^{I-IV}$ (2.3 nM) but a 7-fold greater affinity for its ligand than the extracellular domain of EGFR (500 nM) (see, e.g. Kohda et al., (1993) J. Biol. Chem. 268, 1976-1981). Consequently the results demonstrate that domains I and II of HER3-ECD are sufficient for hrg binding, and the results from proteolysis protection provide evidence that a ligand binding site is located in domain I.

Limited proteolysis of HER3-ECD$^{I-IV}$ and the expression of HER3-ECD$^{I-II}$ provides evidence that the extent to which different domains of the type I receptor tyrosine kinases (EGFR, HER2, HER3, and HER4) contribute to ligand binding may not be conserved among the members of this EGFR family. The data provides evidence that domain I of HER3-ECD$^{I-IV}$ contains a site involved in ligand binding, whereas in EGFR, multiple lines of evidence provide evidence that the ligand contacts both domain I and III (see, e.g. Lax et al., (1989) EMBO J. 8, 421-427; Lax et al., (1991) Cell Regul. 2, 337-345; Wu et al., (1989) J. Biol. Chem. 264, 17469-17475; Summerfield et al., (1996) J. Biol. Chem. 271, 19656-19659; Wu et al., (1990) Proc. Natl. Acad. Sci. U.S.A. 87, 3151-3155) but that domain III alone is sufficient for ligand binding (see, e.g. Kohda et al., (1993) J. Biol. Chem. 268, 1976-1981). It is noteworthy that the $K_d$ for transforming growth factor binding to the monomeric ECD of EGFR is 500 nM. Domain III of EGFR binds transforming growth factor with a $K_d$ of 1.3 µM. The $K_d$ of HER3-ECD$^{I-IV}$ is 1.9 nM, whereas the $K_d$ for HER3-ECD$^{I-II}$ is 68 nM. Therefore, despite a loss of binding compared with HER3-ECD$^{I-IV}$, HER3-ECD$^{I-II}$ still retains a higher affinity for its ligand than the EGFR ECD. EGFR forms dimers in response to ligand binding (see, e.g. Hurvitz et al., (1991) J. Biol. Chem. 266, 22035-22043), whereas HER3-ECD$^{I-IV}$ expressed in S2 cells exists as an oligomer but, following ligand binding, forms a monomer (see, e.g. Landgraf, R., and Eisenberg, D. (2000) Biochemistry 39, 8503-8511). This may be a reflection of the different modes of ligand binding behavior in both receptors. The data provides evidence that for HER3-ECD$^{I-IV}$ ligand binding occurs partly in domain I, whereas domain III may also contribute to binding; the relative contribution of domains I and II to binding appears to be shifted in favor of domain I, for HER3.

An understanding of the activity of type I RTKs has been hindered by the lack of a molecular structure for any member of the family. It has been proposed that the structure of type I RTK ECDs may be similar to the insulin growth factor-1 receptor (IGF-1R) (see, e.g. Jorissen et al., (2000) Protein Sci. 9, 310-324; Garrett et al., (1998) Nature 394, 395-399). The structure of the first three domains of IGF-1R was solved by x-ray crystallography at 2.6-Å resolution (see, e.g. Garrett et al., (1998) Nature 394, 395-399). IGF-1R is a type II receptor tyrosine kinase and is a member of the tyrosine kinase superfamily, which includes the type I (EGFR/HER3) subfamily (see, e.g. Ullrich, A., and Schlessinger, J. (1990) Cell 61, 203-212). HER3 and IGF-1R have significant sequence identity in portions of the extracellular domain and have a similar domain organization (see, e.g. Yarden, Y., and Ullrich, A. (1988) Annu. Rev. Biochem. 57, 443-478; Lax et al., (1988) Mol. Cell. Biol. 8, 1970-1978). In addition, this equivalence has been proposed based on homology modeling between HER3-ECD$^{I-IV}$ and the IGF-1R structure (see, e.g. Jorissen et al., (2000) Protein Sci. 9, 310-324). The IGF-1R structure contains three domains (L1, S1, and L2), which are equivalent to domains I, II, and III in HER3-ECD$^{I-IV}$ (Table I). Domains L1 and L2 are similar in sequence in IGF-1R (25% identity and 41% similarity), as are domains I and III in HER3-ECD$^{I-IV}$ (30% identity and 41% similarity). Domains L1 and L2 also have highly similar structures (see, e.g. Garrett et al., (1998) Nature 394, 395-399). Alanine-scanning mutagenesis of the insulin receptor, a receptor closely related to IGF-1R, identified four regions in the primary sequence of L1 that were important for ligand binding (see, e.g. Williams et al., (1995) J. Biol. Chem. 270, 3012-3016). These regions map to the IGF-1R structure, which reveals a "hormone binding footprint" lying on the face of domain L1 (see, e.g. Garrett et al., (1998) Nature 394, 395-399). A naturally occurring mutation in the insulin receptor at residue 58 lies within the footprint (see, e.g. van der Vorm et al., (1992) J. Biol. Chem. 267, 66-71). Other mutations in the insulin receptor also provide evidence minor contributions in domain L2 (see, e.g. Nakae et al., (1995) J. Biol. Chem. 270, 22017-22022). A model has been suggested in which ligand binding in the IGF-1R involves domains L1 and L2 (see, e.g. Jorissen et al., (2000) Protein Sci. 9, 310-324), which correspond to domains I and III in HER3-ECD$^{I-IV}$.

Figure 8:
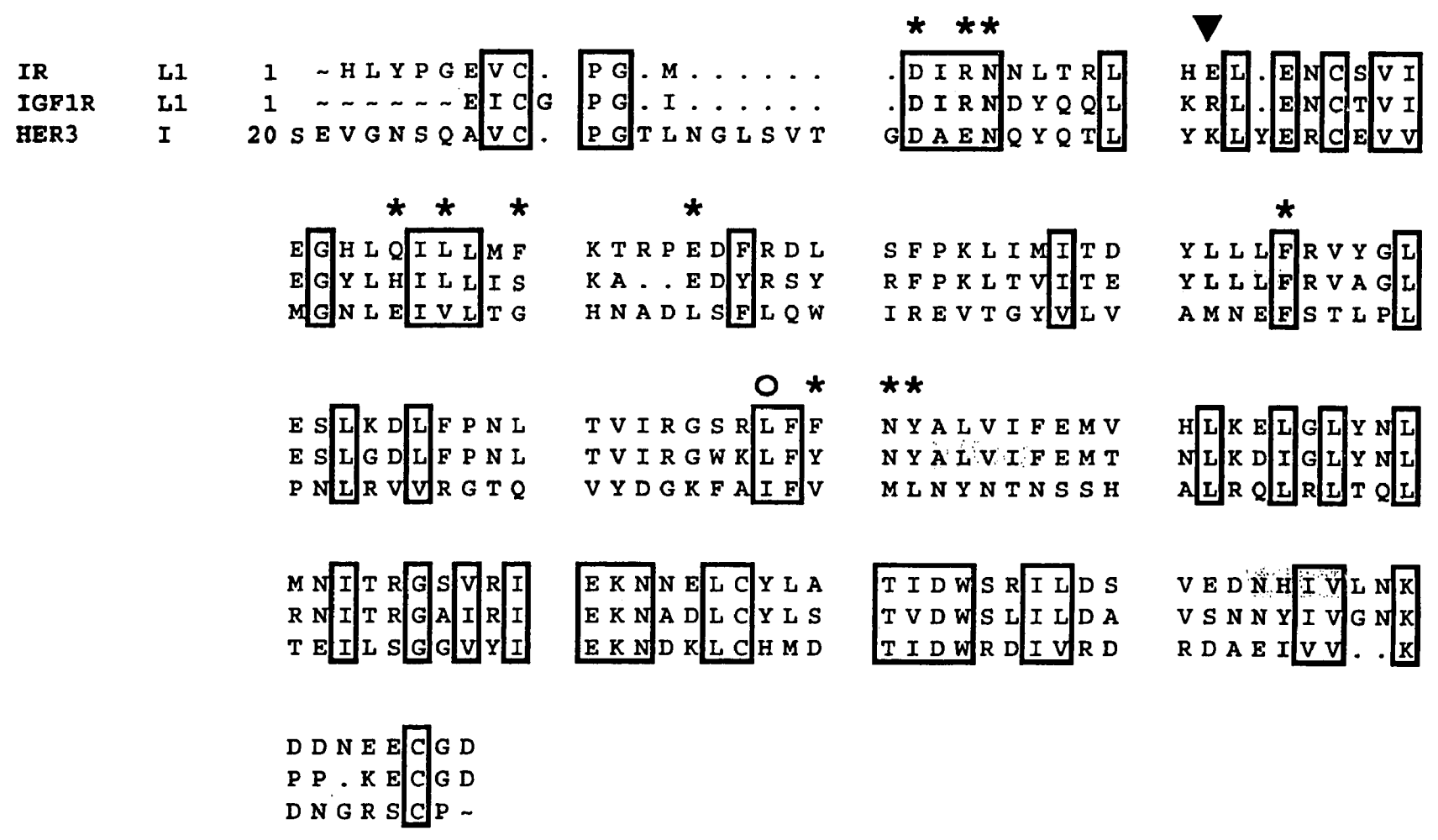

Our current analysis provides biochemical evidence for the proposed structural similarity of type I (HER3) and II (IGF-1R and IR) RTKs. First, a sequence alignment of domain L1 in the IR and the IGF-1R and domain I in HER3-ECD$^{I-IV}$ was performed (FIG. 8). The cleavage site at position 50, which is protected by hrg corresponds to the putative ligand-binding region in domain L1 in IGF-1R (FIG. 9A). Residue 17 in IGF-1R (position 50 in HER3-ECD$^{I-IV}$) lies on the same face as the binding footprint and is 11 Å away from residue 10, which lies within the binding footprint. Second, we expressed HER3-ECD$^{I-II}$, which binds hrg with a 68 nM dissociation constant, supporting the involvement of domain I in ligand binding. Third, the second proteolysis site in which the fragments are held together by a disulfide bridge at position 270 is located in the cysteine-rich domain II of HER3-ECD$^{I-IV}$ (position 237 in the IGF-1R). Based on the IGF-1R structure, cleavage at this position is expected to result in a disulfide-linked fragment (FIG. 9B). Fourth, the large accessible surface area (1782 Å$^2$) of domain L1 that is buried by domain S1 of IGF-1R and the conserved contacts in this interface in the type 1 RTKs (see, e.g. Jorissen et al., (2000) Protein Sci. 9, 310-324) provide evidence that these domains function as unit. This is consistent with our finding that the expression of domain I of HER3 requires the presence of domain II. Therefore, our results are consistent with the proposal that HER3 has a structure similar to IGF-1R. These data provide further insight into areas in the HER3 receptor critical for heregulin binding.

The following examples are offered by way of illustration and not by way of limitation. Various citations are referenced throughout the specification (e.g. PCT application No. WO0160397A1). The disclosures of all citations in the specification are expressly incorporated herein by reference.

EXAMPLES

Example 1

Common Materials

Soluble extracellular domains of recombinant HER3 (HER3-ECD$^{I-IV}$) were purified from Chinese hamster ovary cells by the procedure of Kita et al. (see, e.g. Iita et al., (1996) Biochem. Biophys. Res. Commun. 226, 59-69). The 60-residue EGF-like domain of human heregulin β1 (residues 177-237) (hrg), the binding-deficient heregulin mutant (NA$_5$-hrg), and the thioredoxin-heregulin fusion with a C-terminal His and S-tag (trx-hrg) were generated and purified as described elsewhere (see, e.g. Landgraf et al., (1998) Biochemistry 37, 3220-3228). EGF was purchased from Sigma. Trypsin was purchased from Life Technologies, Inc. (catalog number 15400-013 and lot numbers 12P6334 and 1023241) and Sigma (catalog number T-1426 and lot number 701(7661), which had been treated with tosylamide-2-phenylethylchloromethyl ketone to remove chymotrypsin.

Example 2

Proteolytic Examination of Heregulin and HER3 Interaction

A. Proteolytic Digestion.

5.0 µl of (HER3-ECD$^{I-IV}$) at 2.3 mg/ml in storage buffer (20 mM sodium acetate pH 5.5 and 40 mM sodium chloride), 10 µl of phosphate-buffered saline (PBS): 136 mM NaCl, 2.68 mM KCl, 9.289 mM Na$_2$HPO$_4$, 1.969 mM KH$_2$PO$_4$), and 3.0 µl of trypsin (Life Technologies, Inc.; catalog number 15400-013 and lot number 12P6334) at 5.0 mg/ml in 5.0 mM EDTA and 150 mM sodium chloride were incubated at 37° C. for 1 h. Digestion was stopped by adding phenylmethylsulfonyl fluoride at a final concentration of 1.0 mM. 5.0 µl of the digested sample were added to 5.0 µl of 2×SDS-PAGE sample buffer with and without 1.0 mM β-mercaptoethanol (β-ME). These samples were then analyzed by SDS-PAGE on a 10-15% Phast gel (Amersham Pharmacia Biotech) and visualized by Coomassie staining. Different sources of trypsin were compared, but the best results were obtained with tissue culture grade trypsin from Life Technologies, Inc., which may contain other proteases.

HER3-ECD$^{I-IV}$ was titrated with hrg to determine the minimum amount required for complete protection of HER3-ECD$^{I-IV}$ from proteolysis. Hrg in PBS was incubated with HER3-ECD$^{I-IV}$ for 30 min at room temperature, followed by trypsin as described above. The final concentration of hrg in the digest ranged from 1.7 to 17 µM with a constant HER3-ECD$^{I-IV}$ concentration of 7.7 µM. These reaction mixtures were analyzed by reducing SDS-PAGE as described above. The proteolytic digest was repeated with NA$_5$-hrg and EGF using a molar ratio of 1:1.

B. Proteolysis of HER3-ECD$^{I-IV}$ Results in Two Primary Fragments that Remain Associated Under Oxidizing Conditions.

First, we digested HER3-ECD$^{I-IV}$ to learn if limited proteolysis leads to a fragment still capable of binding hrg. This results in two principal fragments (FIG. 1A, lane 3) with apparent molecular masses of 24 kDa (fragment 1) and 54 kDa (fragment 2), compared with an apparent molecular mass for the nonproteolyzed HER3-ECD$^{I-IV}$ of 80 kDa. Gel electrophoresis of the proteolyzed HER3-ECD$^{I-IV}$ in the absence of a reducing agent shows that the two fragments remain linked by disulfide bonds (FIG. 1A, lane 4). Fragment 2 was identified as the C-terminal fragment by Western blot using the V5 C-terminal epitope-tagged HER3-ECD$^{I-IV}$ (FIG. 1B).

C. Proteolytic Cleavage of HER3-ECD$^{I-IV}$ Abolishes Heregulin Binding

Figure 2:
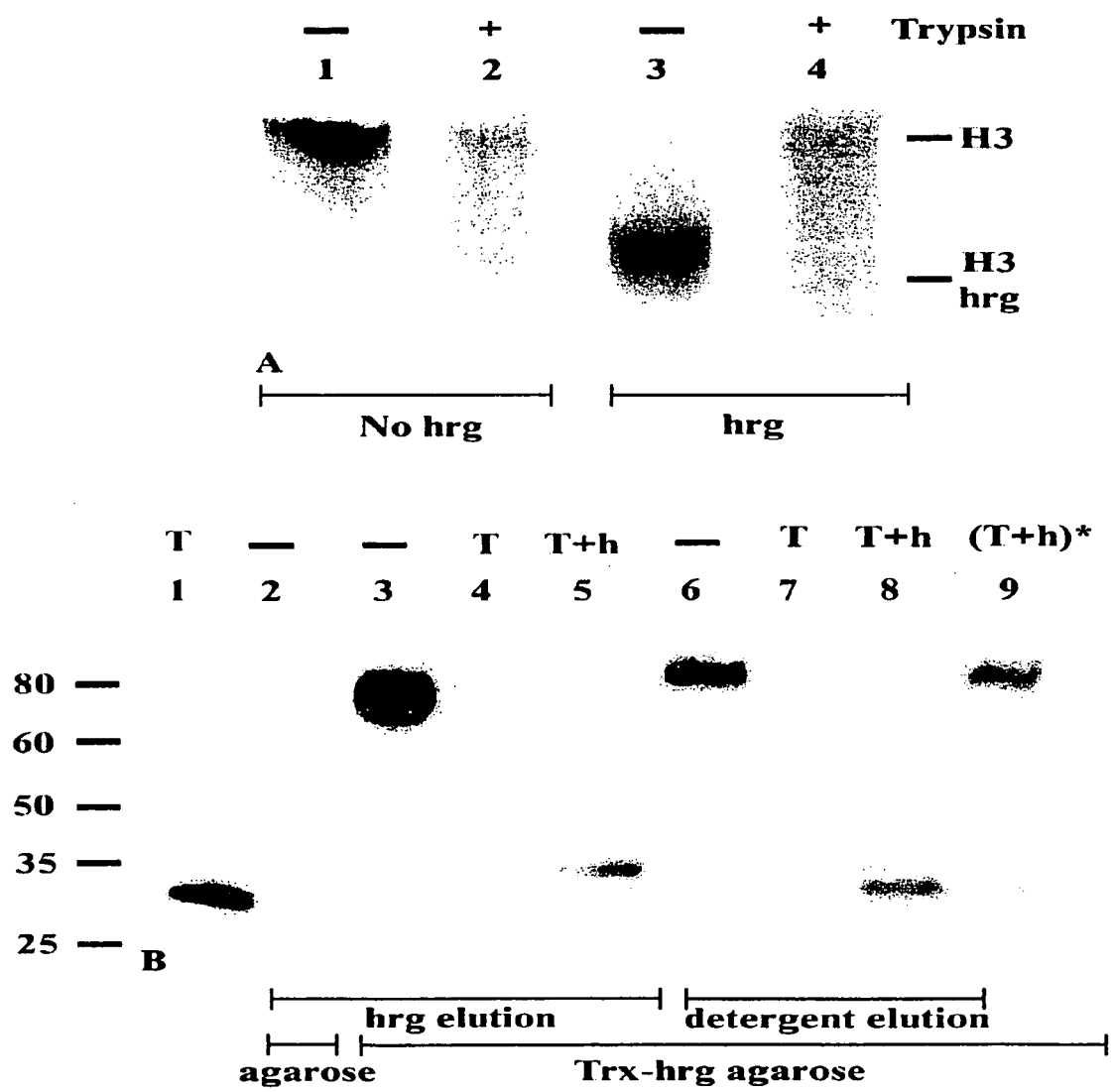
FIG. 2. A, nonproteolyzed HER3-ECD$^{I-IV}$ binds hrg, but proteolyzed HER3-ECD$^{I-IV}$ does not. The presence (+) or absence (−) of tryspin in the proteolytic digest is indicated above the lanes. HER3-ECD$^{I-IV}$ was analyzed on a native Phast gel (10-15%) in the absence (lane 1) and presence (lane 3) of equimolar hrg. Proteolyzed HER3-ECD$^{I-IV}$ was also analyzed in the absence (lane 2) and presence (lane 4) of hrg. Formation of a hrg-HER3-ECD$^{I-IV}$ complex is observed with the nonproteolyzed HER3-ECD$^{I-IV}$ but not with the proteolyzed HER3-ECD$^{I-IV}$. B, nonproteolyzed HER3-ECD$^{I-IV}$ is eluted by hrg in a pull-down assay, but proteolyzed HER3-ECD is not. HER3-ECD$^{I-IV}$ was applied untreated (−) or digested in the absence (T) or presence of hrg (T+h) to agarose-bound hrg. HER3-ECD$^{I-IV}$ was detected with an antibody with an epitope in fragment 1. HER3-ECD$^{I-IV}$ was bound to immobilized hrg and could be eluted with free hrg (lane 3) and detergent (lane 6), but proteolyzed HER3-ECD$^{I-IV}$ could not be eluted with hrg (lane 4) or detergent (lanes 7). HER3-ECD$^{I-IV}$ that was protected by hrg during proteolytic digestion could be recovered by both hrg (lane 5) and detergent (lane 8). Trypsin that was treated with phenylmethylsulfonyl fluoride prior to addition to the digestion reaction (*) did abolish hrg binding by HER3-ECD$^{I-IV}$, which could then be recovered by hrg (lane 9). This demonstrates that proteolyzed HER3-ECD$^{I-IV}$ does not bind hrg.

To determine the effects of cleavage of HER3-ECD$^{I-IV}$ on its ability to bind hrg, a gel mobility shift assay was performed. In a native gel analysis, proteolyzed HER3-ECD$^{I-IV}$ (FIG. 2A, lane 2) shows an electrophoretic mobility similar to the nonproteolyzed HER3-ECD$^{I-IV}$ (FIG. 2A, lane 1). The nonproteolyzed HER3-ECD$^{I-IV}$ shows a discrete shift in the presence of a 1:1 molar ratio of hrg to HER3-ECD$^{I-IV}$ (FIG. 2A, lane 3). The proteolyzed HER3-ECD$^{I-IV}$ does not shift its gel position in the presence of hrg (FIG. 2A, lane 4). This finding provide evidences that the two disulfide-linked fragments, generated by proteolytic digestion (FIG. 1A, lane 4) do not bind hrg.

To check whether the proteolyzed HER3-ECD$^{I-IV}$ binds hrg, we used a pull-down assay under physiological salt conditions. In this analysis, we measured the HER3-ECD$^{I-IV}$ and proteolyzed HER3-ECD$^{I-IV}$ that could be dissociated from immobilized thioredoxin-heregulin (trx-hrg) by the addition of hrg. Using trx-hrg-coupled S-protein agarose, HER3-ECD$^{I-IV}$ was eluted with hrg (FIG. 2B, lane 3). No proteolyzed HER3-ECD$^{I-IV}$ could be recovered by either elution with hrg (FIG. 2B, lane 4) or detergent (FIG. 2B, lane 7). However, HER3-ECD$^{I-IV}$ that was protected by hrg during proteolytic digestion could be recovered by detergent and competition with hrg (FIG. 2B, lanes 5 and 8). In addition, a trypsin preparation that was treated with phenylmethylsulfonyl fluoride prior to the addition to the digestion reaction did not abolish hrg binding by HER3-ECD$^{I-IV}$ (FIG. 2B, lane 9). Based on these results, we conclude that the proteolyzed HER3-ECD$^{I-IV}$ does not bind hrg.

D. Heregulin Protects HER3-ECD$^{I-IV}$ from Proteolytic Cleavage

Figure 3:
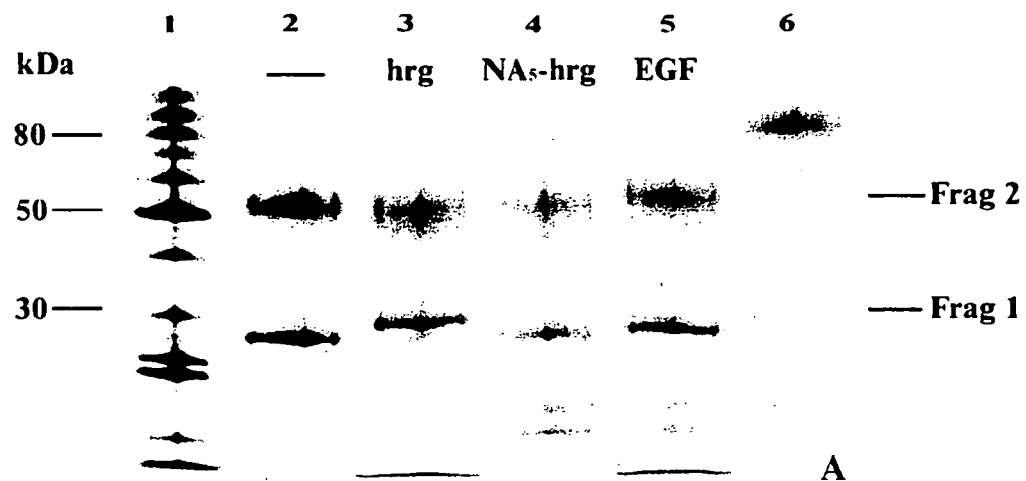
FIG. 3. A, limited proteolysis of HER3-ECD$^{I-IV}$ in the presence of hrg generates a different cleavage pattern than in the absence of hrg when analyzed on an SDS-PAGE Phast gel (10-15%) under reducing conditions. HER3-ECD$^{I-IV}$ was proteolyzed in the absence of ligand (−) and in the presence of hrg, NA$_5$-hrg, and EGF, as indicated above the lanes. Limited proteolysis of HER3-ECD$^{I-IV}$ generates two fragments: one at an apparent molecular mass of 24.2 kDa (fragment 1) and another at 54.1 kDa (fragment 2). In the presence of NA$_5$-hrg (lane 4) and EGF (lane 5), fragment 1 appears to be identical to fragment 1 in the absence of hrg (lane 2), whereas in the presence of wild type hrg (lane 3), fragment 1 appears to have a slightly higher molecular mass. The digest of HER3-ECD$^{I-IV}$ in the presence of a binding-competent hrg generates a different cleavage pattern than in its absence. Apparently, the cleavage that generates fragment 1 can be protected by hrg and is due to a specific interaction between hrg and HER3-ECD$^{I-IV}$. B, the minimum amount of hrg required to produce a change in the molecular weight of fragment 1 in the SDS gel was determined by varying the molar ratio of hrg to HER3-ECD$^{I-IV}$. The ratio of hrg to HER3-ECD$^{I-IV}$ was varied from 2.0 to 0 (lanes 2-8), as indicated above the lanes. A change in the molecular weight of fragment 1 was observed when the molar ratio of hrg to HER3-ECD$^{I-IV}$ was between 0.9:1 and 1:1. Complete protection of HER3-ECD$^{I-IV}$ by hrg was observed at an approximately 1:1 ratio of hrg to HER3-ECD$^{I-IV}$.
Figure 3:
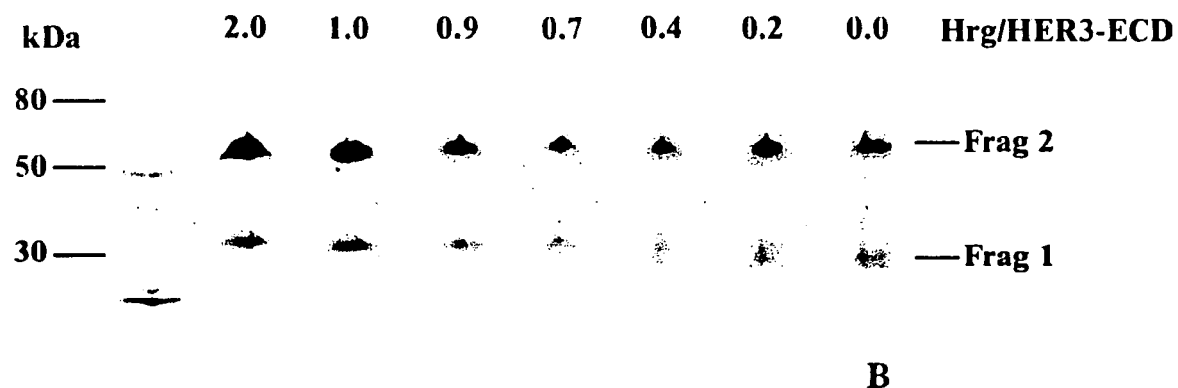

The observation that proteolytic cleavage destroys the binding of HER3-ECD$^{I-IV}$ to hrg provide evidences that cleavage occurs at or near the binding site. This led us to investigate the proteolysis of HER3-ECD$^{I-IV}$ in the presence of hrg. The digestion of HER3-ECD$^{I-IV}$ in the presence of a molar excess of hrg (FIG. 3A, lane 3) produces a different cleavage pattern than in the absence of hrg (FIG. 3A, lane 2). Complete protection of HER3-ECD$^{I-IV}$ was observed (FIG. 3B, lane 3) at an approximate 1:1 molar ratio of hrg over HER3-ECD$^{I-IV}$. Fragment 1 has a higher molecular weight in the presence of hrg (FIG. 3A, lane 3) than in its absence (FIG. 3A, lane 2), whereas the size of fragment 2 is apparently not affected by the presence of hrg (FIG. 3A, lanes 2-5). The cleavage that produces fragment 1 is apparently blocked by hrg but produces an additional, smaller fragment, which was not detected in the SDS gel of the digest of HER3-ECD$^{I-IV}$. These data provide evidence that hrg protects HER3-ECD$^{I-IV}$ from the proteolytic cleavage that generates fragment 1.

E. Localization of the Cleavage Sites

Figure 4:
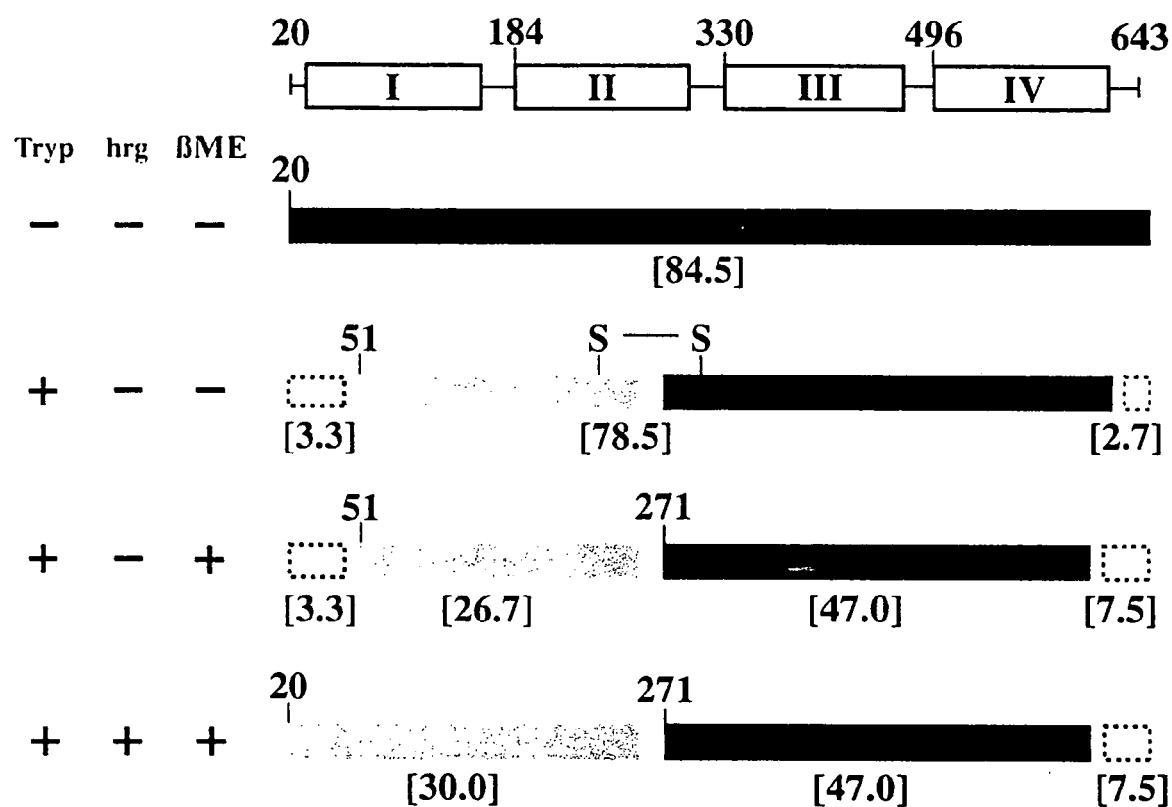
FIG. 4. Domain organization and proteolytic cleavage sites of HER3-ECD$^{I-IV}$. The extracellular region of HER3 contains domains I, II, III, and IV. Sequence positions are indicated at the start of each domain. The beginning of HER3-ECD$^{I-IV}$ at position 20 refers to the start of mature HER3-ECD$^{I-IV}$ after cleavage of the leader sequence. The various digests that were analyzed are shown to the left: the digest of HER3-ECD$^{I-IV}$ in the presence (+) and absence (−) of hrg and mass spectrometry of the oxidized (−βME) and reduced (+βME) forms of the digest. The position of the cleavage site as determined by N-terminal sequencing is indicated at the start of each fragment. Fragment 1 is indicated by a gray bar, and fragment 2 is represented by a black bar. Numbers in brackets are mass estimates in kDa as determined by mass spectrometry. S—S indicates that the two fragments are held together by a disulfide bond. The exact position of the cleavage at the C terminus is unknown, and this is indicated by a dashed bar. The postulated mass of the missing fragments is indicated in brackets below the fragments with dashed lines. In summary, hrg protects HER3-ECD from cleavage at position 50 but not at any other site.

Taken together, these results provide evidence that there are at least two cleavage sites, one that is protected by hrg and another that is not. To localize the positions of the cleavage sites, we used N-terminal sequencing and mass spectrometry. Fragment 1 begins at position 51 in the absence of hrg and at position 20 (the first residue in native HER3-ECD$^{I-IV}$) in the presence of hrg (FIG. 4). The N-terminal 31-residue fragment generated from the cleavage following residue 50 was not detected by SDS-PAGE or by mass spectrometry. The corresponding size by mass spectrometry of fragment 1 is 26.7 kDa in the absence of hrg and 30 kDa in the presence (FIG. 4). The difference in mass of fragment 1 in the presence and absence of hrg is 3270 daltons, which corresponds to the predicted size of 3216 daltons, based on the amino acid sequence of the missing fragment (FIG. 4). This provide evidences that the amino acid residues between positions 20 and 50 of HER3-ECD$^{I-IV}$ are not glycosylated. Based on these results, we conclude that hrg protects HER3-ECD$^{I-IV}$ from proteolysis at position 50.

The cleavage that generates fragment 2 was not blocked by hrg in our assays and is located at position 270. The mass of fragment 2 is 47.0 kDa both in the presence and absence of hrg. The C terminus may contain additional cleavage sites that are not protected by hrg, because there is a missing C-terminal fragment (7.5 kDa) both in the presence and absence of hrg (FIG. 4). However, cleavage of the C terminus could be blocked by an antibody against the V5 epitope tag (FIG. 1b).

The cleavage sites on the carboxyl side of Tyr$^{50}$ and Phe$^{270}$ are more typical of chymotryptic rather than tryptic cleavage. This cleavage could be due to chymotrypsin present in the solution purchased from Life Technologies, Inc. However, the identity of the specific protease involved does not affect the finding that hrg protects HER3-ECD$^{I-IV}$ from cleavage at Tyr$^{50}$ but not at Phe$^{270}$.

F. Protection is Due to a Specific Interaction of hrg with HER3-ECD$^{I-IV}$

Figure 5:
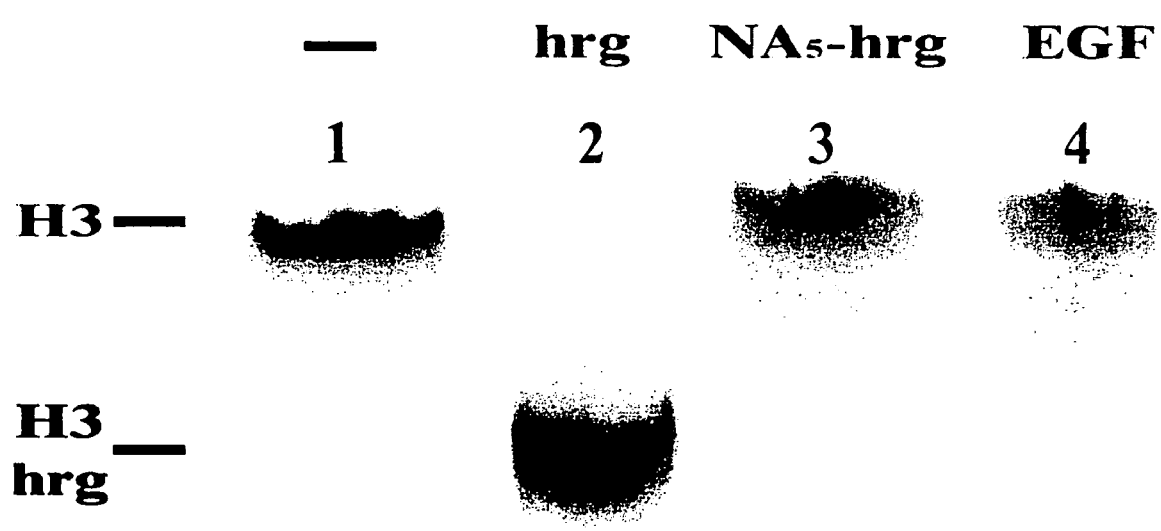
FIG. 5. HER3-ECD$^{I-IV}$ binds hrg but not EGF or the binding-deficient NA$_5$-hrg. HER3-ECD$^{I-IV}$ was analyzed on a native Phast gel (10-15%) in the absence of hrg (lane 1) and in the presence of hrg (lane 2), NA$_5$-hrg (lane 3), and EGF plane 4). The ligands were used at a 1:1 ratio of hrg to HER3-ECD$^{I-IV}$. A complete shift is observed in the presence of hrg, and no shift is apparent in NA$_5$-hrg or EGF.

To show that hrg protection is a result of the specific interaction between hrg and HER3-ECD$^{I-IV}$, we repeated the digestion in the presence of a binding-deficient mutant of hrg (NA$_5$-hrg) and EGF. NA$_5$-hrg is deficient in binding due to the fact that the N-terminal residues that confer specific HER3-ECD$^{I-IV}$ binding were mutated to alanine. NA$_5$-hrg and EGF do not shift the position of HER3-ECD$^{I-IV}$ in a gel mobility shift assay (FIG. 5, lanes 3 and 4). The cleavage pattern obtained in the presence of NA$_5$-hrg and EGF matches that of unprotected HER3-ECD$^{I-IV}$ (FIG. 3A, lanes 4 and 5 versus lane 2), further confirming that they do not bind hrg. Therefore, the difference in the cleavage pattern in the presence of hrg is due to a specific interaction between hrg and HER3-ECD$^{I-IV}$.

Example 3

Heregulin Binding Assays

A. Gel Mobility Shift Assays

HER3-ECD$^{I-IV}$ (1.4 µl) in storage buffer was incubated with 9.6 µl of hrg (6.6 µM in PBS) for 30 min at room temperature. 4.0-μl aliquots of this mixture were run on a 10-15% Phast gel under native conditions. This assay was repeated for $NA_5$-hrg, EGF, and proteolyzed HER3-ECD$^{I-IV}$ under the same conditions.

B. "Pull-Down" Assay Using Immobilized Trx-hrg

The ability of proteolyzed HER3-ECD$^{I-IV}$ to bind hrg was analyzed by a pull-down assay. S-protein agarose (0.5 ml) (Novagen) was spun down and resuspended three times in PBS. Aliquots of 100 μl were spun again, and trx-hrg (600 nM) and bovine serum albumin (BSA) (1 mg/ml) were added to the resin. After incubating 15 min at 4° C., the resin was washed five times with PBS, and blocked again with BSA. The following samples were added to each aliquot of resin: HER3-ECD$^{I-IV}$, proteolyzed HER3-ECD$^{I-IV}$, HER3-ECD$^{I-II}$ protected by hrg during proteolysis, and HER3-ECD$^{I-IV}$ incubated with trypsin deactivated with 1 mM phenylmethylsulfonyl fluoride prior to the proteolysis reaction. HER3-ECD$^{I-IV}$ was at 600 nM. BSA (1 mg/ml) was also added to each aliquot. Following a 15-min incubation at 4° C., the resin was spun down and resuspended three times in PBS. Each aliquot of resin was then resuspended in PBS containing 1 μM hrg or PBS. After a 1-min incubation at 4° C., the samples were spun down, and the supernatant was diluted with 2×SDS-PAGE sample buffer containing 1.0 mM β-ME. Each aliquot of resin was then resuspended in SDS-PAGE sample buffer. The samples were analyzed by SDS-PAGE on a 4-15% polyacrylamide gradient gel (Bio-Rad) and visualized by Western blotting and chemiluminescence using a polyclonal antibody directed against the HER3-ECD (E38530; Transduction Laboratories, Lexington, ICY) followed by incubation with a secondary antibody conjugated to horseradish peroxidase (Invitrogen).

The ability of HER3-ECD$^{I-II}$ to bind hrg was also evaluated in the pull-down assay in the same way, with the following exceptions. HER3-ECD$^{I-II}$ (600 nM) was added to the trx-hrx and control resins, and the individual samples were resuspended in the various competing ligands indicated in FIG. 5. HER3-ECD$^{I-II}$ was visualized by Western blotting and chemiluminescence using a monoclonal antibody directed against the V-5 epitope conjugated to horseradish peroxidase (Invitrogen).

Example 4

Identification of the Digested Fragments and Amino Acid Analysis

Proteolytically digested HER3-ECD$^{I-IV}$ was diluted with sample buffer containing β-ME and run on a 4-15% polyacrylamide gradient gel (Bio-Rad) as described above. The samples were then transferred to a polyvinylidene difluoride membrane, and the fragments were visualized by Ponceau stain. Edman sequencing of excised bands was performed in the UCLA Protein Microsequencing Facility using a Porton-Beckman Gas Phase Sequencer, and the first 10 residues of each fragment were identified. HER3-ECD$^{I-IV}$ was proteolyzed in the presence of an equimolar amount of an antibody against the C-terminal V5 epitope for 30, 60, and 120 min. The C-terminal fragment was identified by Western blotting using an antibody against the C-terminal V5 epitope (Invitrogen).

For the amino acid analysis the molar concentrations of HER3-ECD$^{I-IV}$, hrg, and $NA_5$-hrg were determined by amino acid analysis at the UCLA Protein Microsequencing Facility. The samples were hydrolyzed in 6 N HCl at 110° C. for 18 h under a vacuum in a nitrogen atmosphere. The hydrolysate was visualized with phenylisothiocyanate. The phenylisothiocyanate amino acids were analyzed on a reverse phase column (Novapak) using a sodium acetate-acetonitrile gradient (see, e.g. Bidlingmeyer et al., (1984) J. Chromatogr. 336, 93-104; Cohen, S. A., and Strydom, D. J. (1988) Anal. Biochem. 174, 1-16).

Example 5

Matrix-assisted Laser Desorption Ionization (MALDI) Mass Spectrometry

We used MALDI time-of-flight mass spectrometry to measure the molecular mass of proteolyzed HER3-ECD$^{I-IV}$ and HER3-ECD$^{I-II}$. The mass spectrometry was performed on a Voyager RP machine (PerCeptive Biosystems, Framingham, Mass.) with BSA as an internal standard. 0.3 μl of HER3-ECD$^{I-IV}$ (2.3 mg/ml) in 20 mM sodium acetate pH 5.5, 40 mM sodium chloride was mixed with 0.5 μl of 10 mg/ml sinapinic acid in 70% acetonitrile, 0.1% trifluoracetate and dried on the MALDI plate. The digests (plus and minus hrg) of HER3-ECD$^{I-IV}$ were prepared in the same way, except that the sample was taken directly from the digest reaction after 1 h of incubation time. The digests were run under oxidizing and reducing conditions. The digests were reduced by the addition of 1 mM dithiothreitol prior to mixing the sample with the matrix. The molecular mass of HER3-ECD$^{I-II}$ (12 μM) in PBS was measured under the same conditions.

Example 6

Sequence Alignments and Surface Area Calculations

An initial multiple sequence alignment was performed with the GCG program Pileup (Wisconsin Package, SeqLab, SeqWeb) using the Blossum 62 matrix (see, e.g. Henikoff, S., and Henikoff, J. G. (1992) Proc. Natl. Acad. Sci. U.S.A. 89, 10915-10919). Empirical observations of the N terminus were used in conjunction with the initial alignment to produce a final alignment. We used the GCG program Bestfit (Wisconsin Package, SeqLab, SeqWeb) (see, e.g. Smith, T., and Waterman, M. (1981) Adv. Appl. Math. 2, 482-489) to find the segment of greatest similarity between two sequences. The amount of solvent-exposed surface area of domain L1 that is buried by domain S1 of IGF-1R was calculated using the GCG program Areaimol (see, e.g. Lee, B., and Richards, F. M. (1971) J. Mol. Biol. 55, 379-400; Collaborative Computational Project. (1994) Acta Crystallogr. Sect. D 50, 760-763).

Example 7

Cloning and Expression of HER3-ECD$^{I-II}$

The HER3 cDNA was amplified from the pJTH3 plasmid provided by Amgen, using the N-terminal primer (CTA GTC TCT AGA TCC GAG GTG GGC AAC TCT) (SEQ ID NO: 7) and C-terminal primer (TAC CGA TCT AGA TTT CGG ACA GAG ACC CCC) (SEQ ID NO: 8). Following amplification, HER3-ECD$^{I-II}$ (residues 20-329) was cloned into the BglII and XbaI site of the pMT/BiP/V5-His-A expression vector (Invitrogen, Carlsbad, Calif.). This vector contains an N-terminal *Drosophila* leader sequence and C-terminal His tag and V5 epitope tags. S2 cells were co-transfected with the vector containing HER3-ECD$^{I-II}$ and the pCoHYGRO vector (Invitrogen), which provides hygromycin resistance. We obtained a stable cell line after 3 weeks of selection with 300 µg/ml hygromycin (Invitrogen). Five liters of S2 medium (Sigma) with 1% fetal bovine serum were inoculated with S2 cells and grown to a cell density of 5×106 in a spinner flask (Bellco) and then induced for 3 days at room temperature with 500 µM $CuSO_4$. HER3-$ECD^{I-II}$ was secreted to the medium. We used an ammonium sulfate cut (80%, w/v) to precipitate the protein from the medium. The pellet was resolubilized in 20 mM Tris, pH 7.9, 1.5 M NaCl, and 0.1% Tween 20. The solution was dialyzed into 20 mM Tris, pH 7.9, 0.5 M NaCl, and 5 mM imidazole and then purified on a 5-ml Amersham Pharmacia Biotech "HITRAP Chelating" column (Amersham Pharmacia Biotech), loaded with $NiSO_4$. Following elution from the column, the protein was dialyzed into 20 mM sodium potassium phosphate, pH 10. The protein was loaded onto an anion exchange column (Bio-Rad), and pure HER3-$ECD^{I-II}$ was collected from the flow-through.

Example 8

Multiangle Light Scattering of HER3-$ECD^{I-II}$

Size exclusion chromatography was performed using a TosoHaas G3000SWXL column, followed by light scattering on a miniDAWN three-angle light-scattering instrument (Wyatt Technologies, Santa Barbara, Calif.). Data analysis was carried out using ASTRA software. HER3-$ECD^{I-II}$ 112 µM) in 20 mM Hepes, pH 7.5, was injected onto the column at a flow rate of 0.4 ml/min. The refractive index increment (dn/dc) for the protein portion of the HER3-$ECD^{I-II}$ in this buffer was assumed to be equal to that of monomeric BSA (Sigma) (dn/dc=0.181 $cm^3$/g). The carbohydrate dn/dc contribution was estimated to be 0.157 $cm^3$/g and was integrated into the final dn/dc (0.180 $cm^3$/g) proportionally. Calculated extinction coefficients uncorrected for folding effect were used. The error to noise in the light scatter data is about ±3%. An error in the assumed extinction coefficient would result in a proportional error in the calculated molecular mass.

Example 9

Ultracentrifugation of HER3-$ECD^{I-II}$

Sedimentation equilibrium was performed at 4° C. in a Beckman Optima XL-A analytical ultracentrifuge using absorption optics at 280 nm. A 12-mm path length six-sector cell was used to measure protein samples at initial $A_{280}$ values of 0.15, 0.35, and 0.75. All samples were in PBS. Sedimentation equilibrium profiles were measured at 12,000 and 15,000 rpm. The data were initially fitted with a non-linear least-squares exponential fit for a single ideal species using Origin (version 3.01). Since no concentration or speed dependence of the molecular weight was apparent, the Beckman global analysis software (the "multifit" option of the above mentioned software) was used to analyze all six scans simultaneously. A partial specific volume of 0.712 calculated from the amino acid composition and corrected to 4° C. was used (see, e.g. Cohn, E. J., and Edsall, J. T. (1943) in Proteins, Amino Acids and Peptides as Ions and Dipolar Ions (Cohn, E. J., and Edsall, J. T., eds), pp. 370-381, Reinhold Publishing Corp., New York; Laue et al., (1992) in Analytical Ultracentrifugation in Biochemistry and Polymer Science (Harding, S. E., Rowe, A. J., and Horton, J. C., eds), pp. 90-125, The Royal Society of Chemistry, Cambridge, United Kingdom).

Example 10

Surface Plasmon Resonance Measurement of Binding Between HER3-$ECD^{I-II}$ and the EGF-like Domain of Heregulin Trx-hrg (13 µM) in MES buffer (100 mM pH 6.0) was immobilized on a BIAcore CM5 chip using standard N-hydroxysuccinimide/1-ethyl-3-(3-dimethylaminopropyl)carbodiimide amine-coupling chemistry. The surface of the chip was blocked with ethanolamine and could be regenerated with 5.0 M NaCl and washes with running buffer (PBS+surfactant). HER3-$ECD^{I-II}$ (filtered through a 0.1-µm filter unit (Millipore, Bedford, Mass.)) in running buffer was applied to the chip at various concentrations (in triplicate) to determine the dissociation constant. Data were analyzed with the BIAevaluation software. Competition experiments were carried out using hrg at an equimolar concentration to HER3-$ECD^{I-II}$.

Example 11

Recombinant HER3-$ECD^{I-II}$ Is Sufficient for Heregulin Binding

Figure 6:
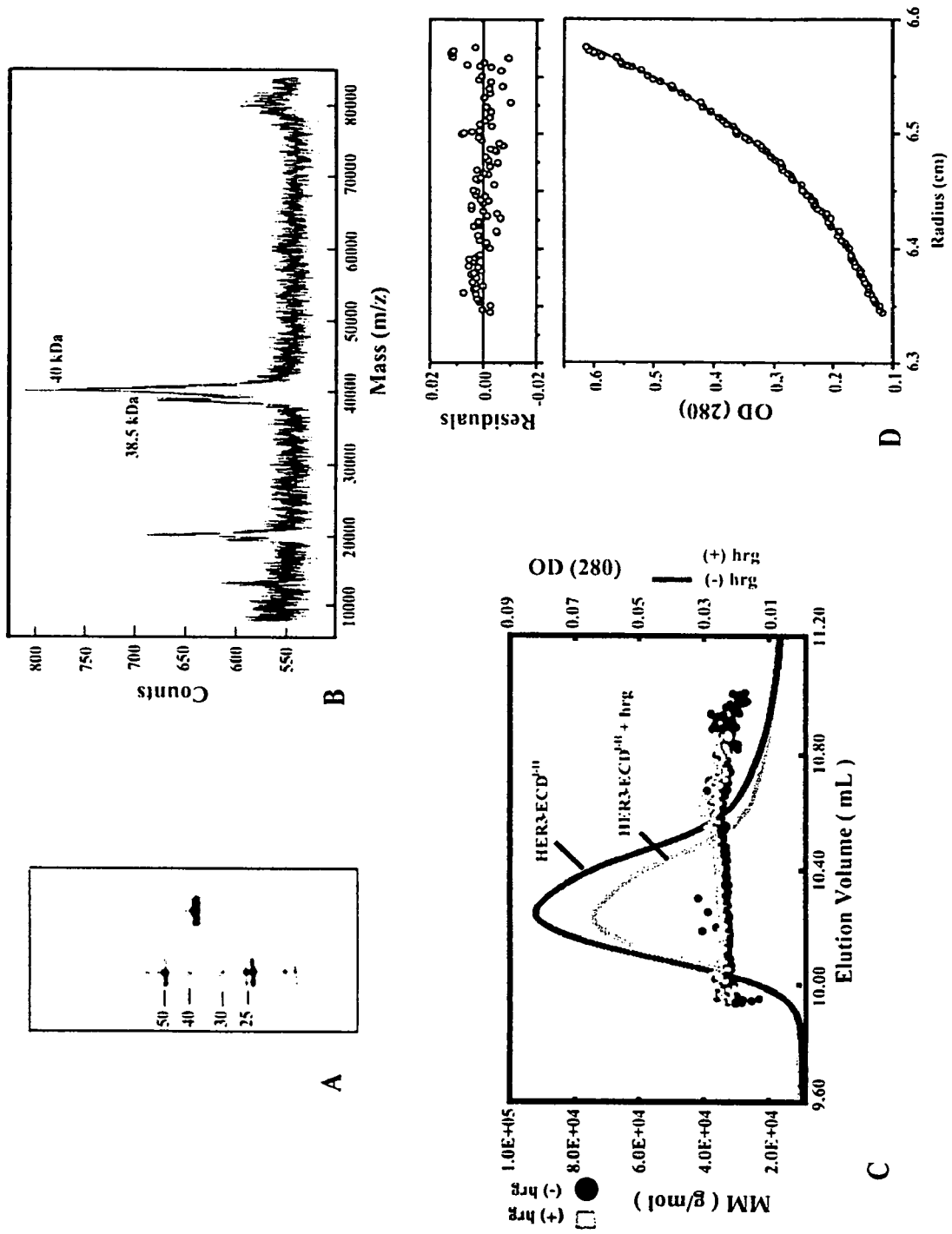
FIG. 6. Characterization of recombinant HER3-ECD$^{I-II}$ by SDS-PAGE analysis, mass spectrometry, light scattering, and equilibrium centrifugation. A, recombinant HER3-ECD$^{I-II}$ is pure as judged by SDS-PAGE analysis. HER3-ECD$^{I-II}$ was expressed in *Drosophila* S2 cells and purified from the medium. The molecular mass appears to be somewhat less than 40 kDa. B, the molecular mass of HER3-ECD$^{I-II}$ is between 38.5 and 40 kDa as determined by MALDI mass spectrometry, compared with a theoretical molecular mass of 37.7 kDa. This provide evidences that HER3-ECD$^{I-II}$ has a carbohydrate content between 3.3 and 5.7% by weight. C, recombinant HER3-ECD$^{I-II}$ is a monomer as determined by size exclusion chromatography followed by multiangle light scattering. Recombinant HER3-ECD$^{I-II}$ eluted in a single peak (black line) with a molecular mass of ~34 kDa (S.E.=±4%) (black circles). The addition of a 1.3-fold molar excess of hrg caused a slight shift in the peak (gray line). The shifted peak has a molecular mass of 35 kDa (S.E.=±3%) (gray squares). Recombinant HER3-ECD$^{I-II}$ is a monomer and remains a monomer in the presence of hrg. D, recombinant HER3-ECD$^{I-II}$ is a monomer, as determined by ultracentrifugation at three different concentrations and three different speeds. The average molecular mass of HER3-ECD$^{I-II}$ is 35.0 kDa (S.E.=±0.6%), which corresponds to monomeric HER3-ECD$^{I-II}$.

To show that a ligand binding site is located within domain I of HER3-$ECD^{I-IV}$, we recombinantly expressed domain I of HER3 alone (HER3-$ECD^{I}$) as well as domains I and II together (HER3-$ECD^{I-II}$). Expression of domain I alone resulted in an improperly folded protein because of incorrect disulfide formation, so only HER3-$ECD^{I-II}$ could be evaluated for ligand binding. The recombinant form of HER3-$ECD^{I-II}$ (residues 20-329) was expressed in Drosophila S2 cells and purified from the medium. The protein was found to be pure by SDS-PAGE analysis with an apparent molecular mass of 40 kDa (FIG. 6A). We used MALDI mass spectrometry to estimate the carbohydrate content. The molecular mass of HER3-$ECD^{I-II}$ was found to be between 38.5 and 40 kDa, compared with a theoretical molecular mass of 37.7 kDa (FIG. 6B). This provide evidences that HER3-$ECD^{I-II}$ has a carbohydrate content between 3.3 and 5.7% by weight.

Size exclusion chromatography followed by multiangle light scattering was used to show that recombinant HER3-$ECD^{I-II}$ is a monomer. The concentration of HER3-$ECD^{I-II}$ at the time of light scattering was 1.8 µM. At this concentration, a single peak was observed with a molecular mass of ~34 kDa (S.E.=±4%) corresponding to monomeric HER3-$ECD^{I-II}$ (FIG. 6C). There was a slight shift in the peak upon the addition of a 1.3-fold molar excess of hrg. The shifted peak has an estimated molecular mass of 35 kDa (S.E.=±3%) (FIG. 6C). To confirm that HER3-$ECD^{I-II}$ is a monomer, we used ultracentrifugation at three different concentrations and three different speeds. The estimated average molecular weight of HER3-$ECD^{I-II}$, using a group analysis of all of the scans, is 35,000±210 daltons (FIG. 6D). This is consistent with the expected molecular mass (37.5 kDa) of monomeric HER3-$ECD^{I-II}$.

Figure 7:
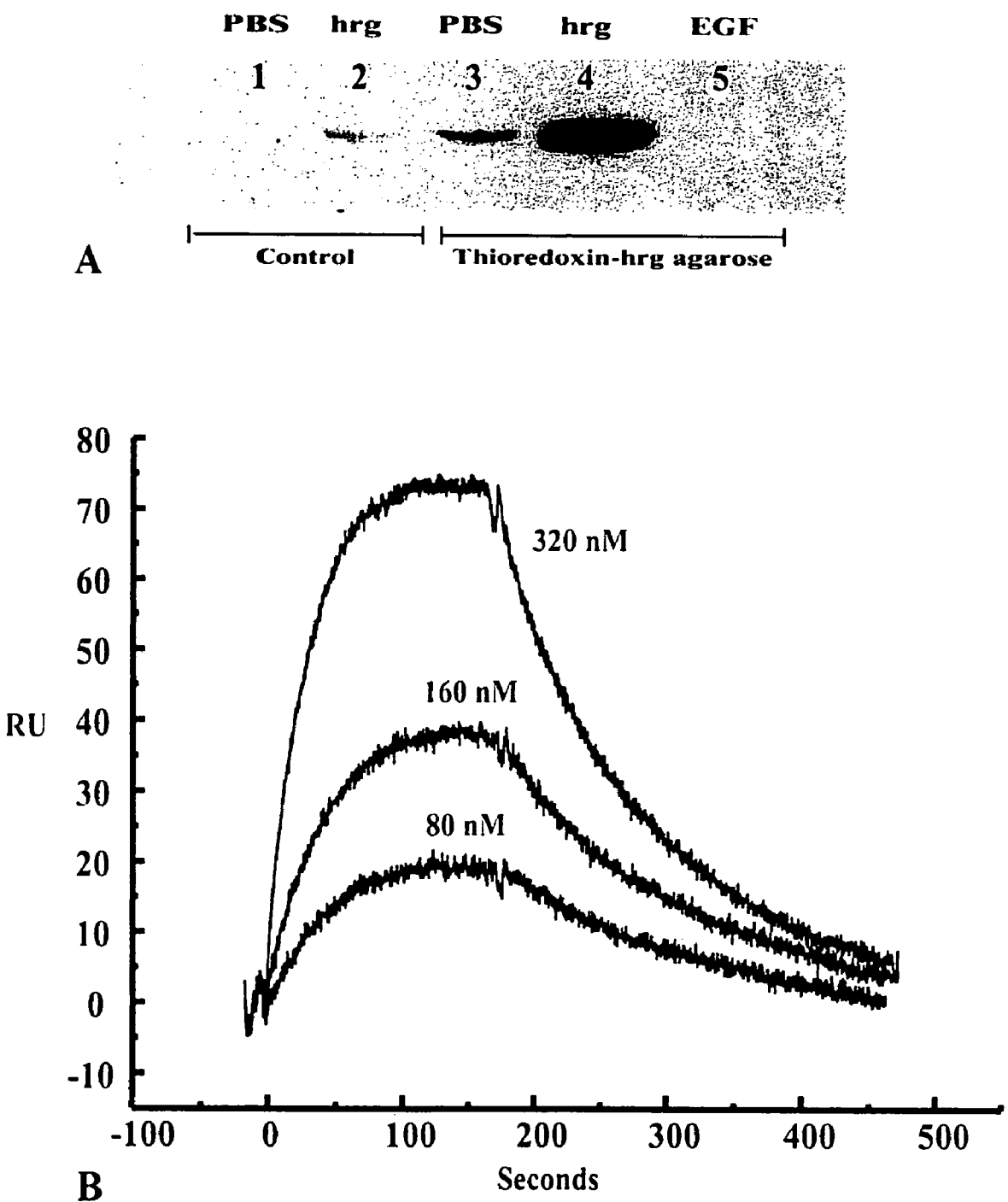
FIG. 7. Recombinant HER3-ECD$^{I-II}$ binds hrg. A, HER3-ECD$^{I-II}$ was analyzed in a pull-down assay in which S-tagged hrg was immobilized on S-protein resin (lanes 3-5) and could be specifically eluted with 1 µM hrg (lane 4) but not PBS (lane 3) or 1 µM EGF (lane 5). The fragment showed little nonspecific binding to S-protein resin without immobilized S-tagged hrg (lanes 1 and 2) when eluted with PBS plane 1) or 1 µM hrg plane 2). This shows that domains I and II of HER3-ECD$^{I-IV}$ are involved in hrg binding. B, recombinant HER3-ECD$^{I-II}$ has a K$_d$ of 68 nM as determined by SPR (BIAcore). HER3-ECD$^{I-II}$ showed binding to immobilized trx-hrg with a calculated equilibrium dissociation constant of 68 nM using the three different concentrations of HER3-ECD$^{I-II}$ indicated. This shows that HER3-ECD$^{I-II}$ binds hrg.

We used two independent methods to demonstrate direct binding of hrg to HER3-$ECD^{I-II}$: a pull-down assay and surface plasmon resonance (SPR; BIAcore) analysis. Binding of hrg to HER3-$ECD^{I-II}$ was shown using a pull-down assay under physiological salt conditions. In this analysis, we measured the amount of the V5-tagged HER3-$ECD^{I-II}$ that dissociated from immobilized trx-hrg by the addition of hrg. Using the trx-hrg-coupled S-protein-agarose, HER3-$ECD^{I-II}$ could be eluted with 1 µM hrg (FIG. 7A, lane 4). In contrast, neither PBS (FIG. 7A, lane 3) nor EGF (FIG. 7A, lane 5) was effective in eluting HER3-ECD$^{I-II}$.

To further confirm that HER3-ECD$^{I-II}$ binds hrg, we analyzed the interaction by SPR (BIAcore). Trx-hrg fusion protein was immobilized on a BIAcore chip for these measurements. SPR measurements using HER3-ECD$^{I-II}$ showed binding to the immobilized trx-hrg with a calculated equilibrium dissociation constant of 68 nM, calculated directly from $k_{on}$ and $k_{off}$ ($k_{on}=(1.07\pm0.1)\times10^5$ M$^{-1}$ s$^{-1}$; $k_{off}=(7.27\pm1)\times10^{-3}$ s$^{-1}$) (FIG. 7b). This interaction could be inhibited by stoichiometric concentrations of hrg. Based on these results, we conclude that HER3-ECD$^{I-II}$ containing domains I and II of HER3 binds hrg.

Example 12

Identification, Generation and Characterization of HER3 Residues Involved in Heregulin Binding A. Generation of trx-hrg and HER3 Point Mutants A thioredoxin-heregulin fusion (trx-hrg) was generated and purified as described elsewhere (see, e.g. Landgraf et al. (1998) *Biochemistry* 37(9), 3220-8). The HER3 point mutants were generated using the method of oligonucleotide directed mutagenesis described by Kunkel (see, e.g. Kunkel, T. A. (1988) *Nucleic Acids Symp Ser* (19), 43). Table 1 contains the oligonucleotides used for the mutagenesis. The PCR fragments were subcloned into the Bgl 2 and EcoR-1 site of HER3$^{I-IV}$ (residues 20-329) and HER3$^{I-IV}$ (residues 20-643) in the pMT/BiP/V5-His-A expression vector (Invitrogen, Carlsbad, Calif.) and confirmed by sequencing. The mutants were expressed and purified as described elsewhere (see, e.g. Singer et al. (2001) *J Biol Chem* 276(47), 44266-74).

B. Quantitation of the HER3 Point Mutants

The concentration of the mutants were determined by analyzing the samples by SDS-PAGE on a 4-15% gradient gel (Biorad) followed by Western Blotting and chemiluminescence using a monoclonal antibody directed against the V-5 epitope conjugated to horse radish peroxidase (Invitrogen). Each mutant was run in triplicate and compared to a known concentration of HER3$^{I-II}$ (see, e.g. Singer et al. (2001) *J Biol Chem* 276(47), 44266-74).

C. Binding Assays, Mass Spectrometry and CD Analysis:

The gel shift assay, "pull down" assay, and surface plasmon resonance measurements were performed as described elsewhere (see, e.g. Singer et al. (2001) *J Biol Chem* 276(47), 44266-74). Matrix-assisted Laser Desorption Ionization (MALDI) time-of-flight mass spectrometry was performed as described elsewhere (see, e.g. Singer et al. (2001) *J Biol Chem* 276(47), 44266-74). The CD analysis was performed using a circular dichroism instrument from AVIV (Lakewood, N.J.) with a 0.1 mM pathlength. The scan was performed from 260 nM to 195 nM every 1.0 nM with 1.50 nM between scans and 3.0 seconds to collect each point.

D. A Mutation of Residue 64 in HER3 to Alanine Abolishes Heregulin Binding

HER3$^{I-II\ E64A}$ has a decreased affinity for heregulin binding. To locate the region of domain I that is critical for hrg binding, we expressed a series of point mutants in domain I of HER3$^{I-II}$ and assayed for hrg binding by two independent methods: a pull down assay and BIAcore analysis. To determine whether the mutants of HER3$^{I-II}$ are capable of binding hrg, we used a "pull down" assay in which we measured the HER3$^{I-II}$ that could be dissociated from immobilized thioredoxin-heregulin (trx-hrg) by the addition of hrg. Using trx-hrg coupled S-protein agarose, HER3$^{I-II}$ was eluted with hrg and detergent (FIG. 10A, lanes 3 and 5). No HER3$^{I-II\ E64A}$ could be recovered by either elution with hrg or detergent. (FIG. 10A, lanes 4 and 6) This provides evidence that HER3$^{I-II\ E64A}$ does not bind hrg.

To further confirm that HER3$^{I-II\ E64A}$ does not bind hrg, we analyzed the interaction by surface plasmon resonance (SPR, BIAcore). Trx-hrg fusion protein was immobilized on a BIAcore chip for these measurements. We have previously shown that HER3$^{I-II}$ showed binding to immobilized trx-hrg with a calculated equilibrium dissociation constant of 68 nM using SPR measurements (see, e.g. Singer et al. (2001) *J Biol Chem* 276(47), 44266-74). HER3$^{I-II\ E64A}$ had a Kd of 95 nM, HER3$^{I-II\ V110A}$ had a Kd of 15 nM, (Table 2) HER3$^{I-II\ E64A}$ had no detectable binding above 500 nM to the immobilized hrg on the BIAcore chip. (FIG. 10B). All other mutants had a Kd similar to wild type. These results provide evidence that residues 44, 64, and 110 are in the heregulin binding region of HER3, and that residue 64 is critical for heregulin binding.

The residue at position 51 was also mutated to alanine because it could be protected by hrg from proteolytic cleavage, but was not directly in the binding footprint (Singer, 2001). HER3$^{I-II\ K51A}$ had the same Kd as HER3$^{I-II}$ (Table 2). This provides evidence that residue 51 contributes no binding energy directly to HER3-heregulin interactions.

Figure 11:
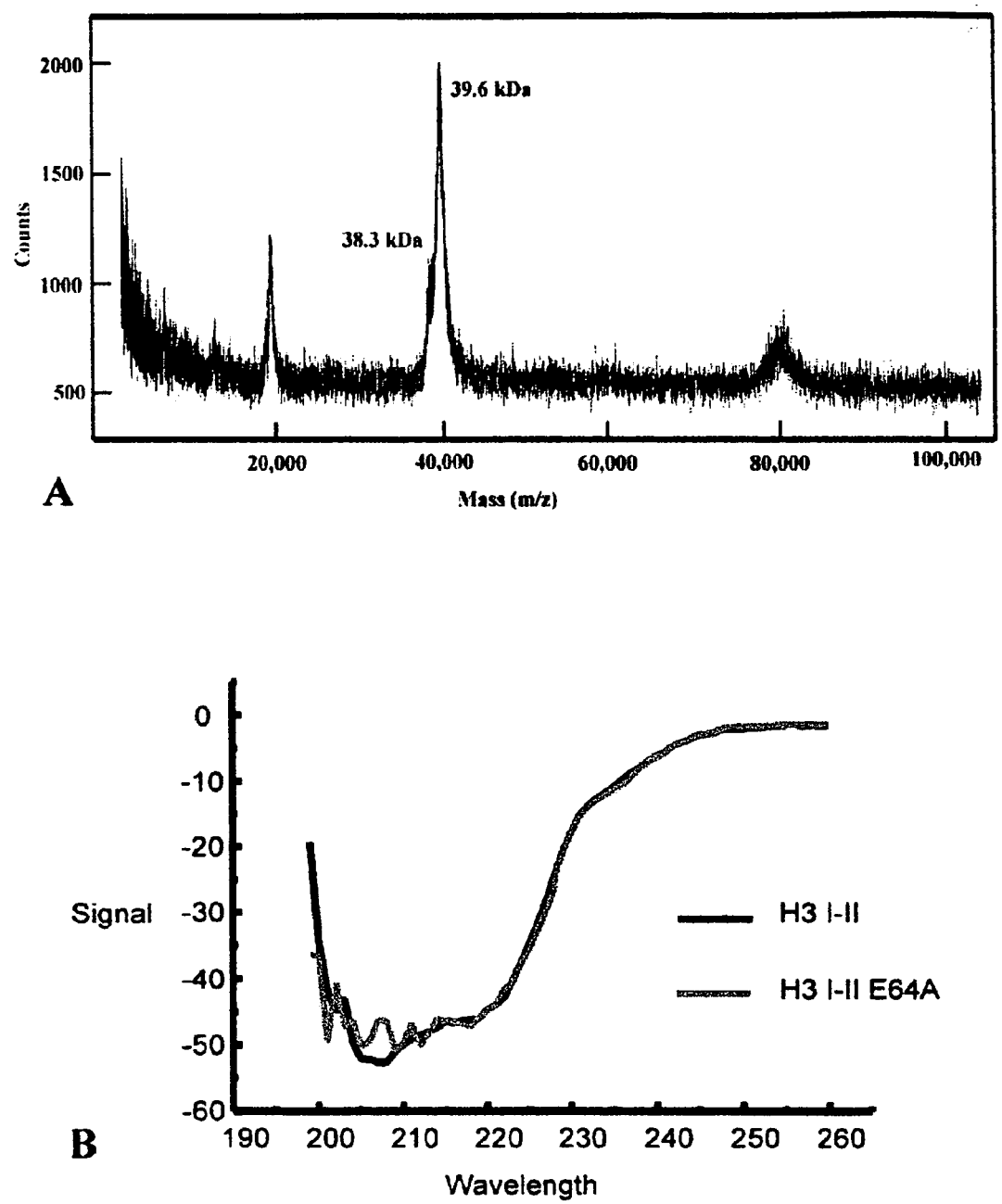
FIG. 11. Characterization of recombinant HER3$^{I-IIE64A}$ by mass spectrometry and circular dichroism. A, the molecular mass of HER3$^{I-II\ E64A}$ is between 38.4 and 40.6 kDa as determined by MALDI mass spectrometry, which is comparable to the molecular mass of HER3$^{I-II}$ (38.5 and 40 kDa). This provides evidence that the polypeptide chain of HER3$^{I-IIE64A}$ is intact. B, the CD spectra of HER3$^{I-II}$ and HER3$^{I-II}$ were essentially identical between 210 nM and 260 nM provide evidencing that they have the same secondary structure.

To show that the decreased binding affinity of HER3$^{I-II\ E64A}$ is not a result of proteolysis or misfolding, we performed mass spectrometry and CD analysis of HER3$^{I-II\ E64A}$. The molecular mass of HER3$^{I-II\ E64A}$ is between 38.4 kDa and 39.8 kDa which is comparable to the molecular mass of HER3$^{I-II}$ (38.5 and 40 kDa) (FIG. 11A). This provides evidence that the polypeptide chain of HER3$^{I-II\ E64A}$ is intact. The CD spectra of HER3$^{I-II\ E64A}$ and HER3$^{I-II}$ were essentially identical between 210 nM and 260 nM providing evidence that they have the same secondary structure. (FIG. 11B). The fluctuations in the signal between 190 nM and 210 nM in HER3$^{I-II\ E64A}$ are probably due to aggregation. These results show that a mutation at residue 64 in HER3$^{I-II}$ has little affect on the structure of the protein, but results in decreased affinity for hrg.

Figure 12:
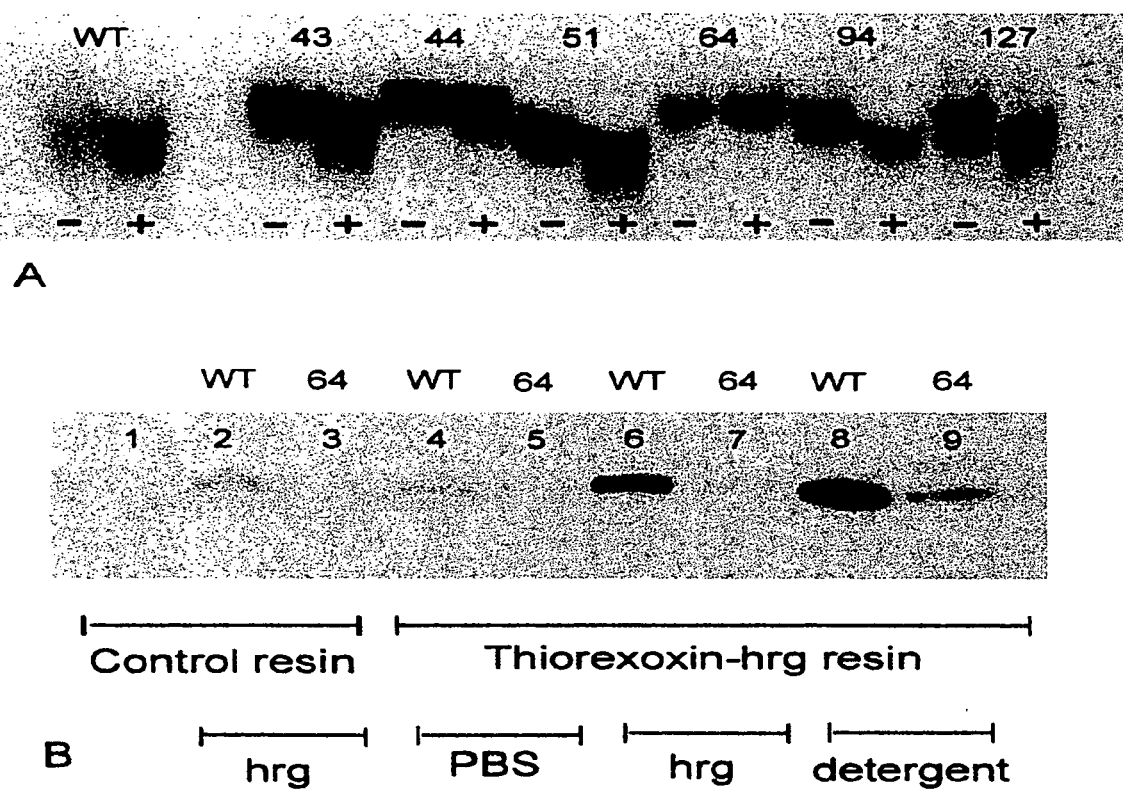
FIG. 12. A, HER3$^{I-IV}$ binds hrg, but HER3$^{I-IV\ E64A}$ does not. HER3$^{I-IV}$ and the HER3$^{I-IV}$ mutants were analyzed on a native Phast gel (10-15%) in the absence (−) and presence (+) of equimolar hrg. The HER3$^{I-IV\ E64A}$ was also analyzed in the absence (lane 2) and presence (lane 4) of hrg. Formation of a hrg-HER3$^{I-IV}$ complex is observed with HER3$^{I-IV}$, but not with HER3$^{I-II\ E64A}$, B, HER3$^{I-IV}$ and HER3$^{I-IV\ E64A}$ were analyzed in a "pull down assay" in which S-tagged hrg was immobilized on S-protein resin (lanes 4-9) and HER3$^{I-IV}$ could be specifically eluted with 1 μM hrg and detergent (lane 6 and 8), but HER3$^{I-IV\ E64A}$ could not be eluted with PBS or 1 μM hrg (lanes 5 and 7). A small amount of HER3$^{I-IV\ E64A}$ could be eluted with detergent (lane 9) which was probably due to some binding or non-specific interaction. Both HER3$^{I-IV}$ and HER3$^{I-IV\ E64A}$ showed little non-specific binding to S-protein resin without immobilized S-tagged hrg when eluted with 1 μM hrg (lane 2-3). This shows that HER3$^{I-IV\ E64A}$ does not bind hrg.

To show that mutation at residue 64 has an effect in the extracellular domain of HER3, we expressed a series of mutants including HER3$^{I-IV\ E64A}$ and HER3$^{I-IV}$ and assayed for hrg binding by two independent methods: a native gel analysis, and a "pull down" assay. To determine the effects of cleavage of HER3$^{I-IV}$ on its ability to bind hrg, a gel mobility shift assay was performed. In a native gel analysis, HER3$^{I-IV}$ shows an electrophoretic mobility similar to HER3$^{I-IVE64A}$. HER3$^{I-IV}$ shows a discrete shift in the presence of a 1:1 molar ratio of hrg to HER3$^{I-IV}$. HER3$^{I-IVE64A}$ does not shift its gel position in the presence of hrg. (FIG. 12A). This finding provides evidence that HER3$^{I-IVE64A}$ does not bind hrg.

To confirm that HER3$^{I-IVE64A}$ has decreased binding affinity for hrg, we used a "pull down" assay in which we measured the HER3$^{I-IV}$ and HER3$^{I-IVE64A}$ that could be dissociated from immobilized thioredoxin-heregulin (trx-hrg) by the addition of hrg. Using trx-hrg coupled S-protein agarose, HER3$^{I-IV}$ was eluted with hrg and detergent (FIG. 12B, lanes 6 and 8), but not with PBS (FIG. 12B, lane 4). No HER3$^{I-IV\ E64A}$ could be recovered by elution with PBS, hrg or detergent (FIG. 12B, lanes 5, 7 and 9). This provided evidence that HER3$^{I-IV\ E64A}$ does not bind hrg.

E. Amino Acids 64 and 110 are Critical for Heregulin Binding

In this study, we have identified two amino acids in discontinuous segments in domain I of HER3 which appear to be critical for heregulin binding. A mutation at residue 64 seemed to decrease all binding affinity in both recombinant H3$^{I\text{-}IV\ E64A}$ and H3$^{I\text{-}II\ E64A}$ No detectable binding could be measured by gel shift, Biacore, or pull down assay. H3$^{I\text{-}II\ E64A}$ seemed to be correctly folded as determined by CD analysis. These experimental results provide evidence that the decrease in binding affinity observed with this mutation is probably due to direct effects on interaction between H3$^{I\text{-}II\ E64A}$ and heregulin rather than the consequences of misfolding or proteolysis of the mutant protein. A mutation at residue 110 (H3$^{I\text{-}II\ V110A}$) caused a 4 fold increase in binding affinity. A mutation at residue 44 (H3$^{I\text{-}II\ E44A}$) had a 1.5 fold decrease in binding affinity A mutation at the protected proteolysis site (H3$^{I\text{-}II\ K51A}$) had no effect on binding affinity. These results provide evidence that amino acids 64 and 110 are critical for heregulin binding.

F. Residues 64 and 110 Map to the Hormone Binding Footprint in the IGF-1R Structure.

Figure 13:
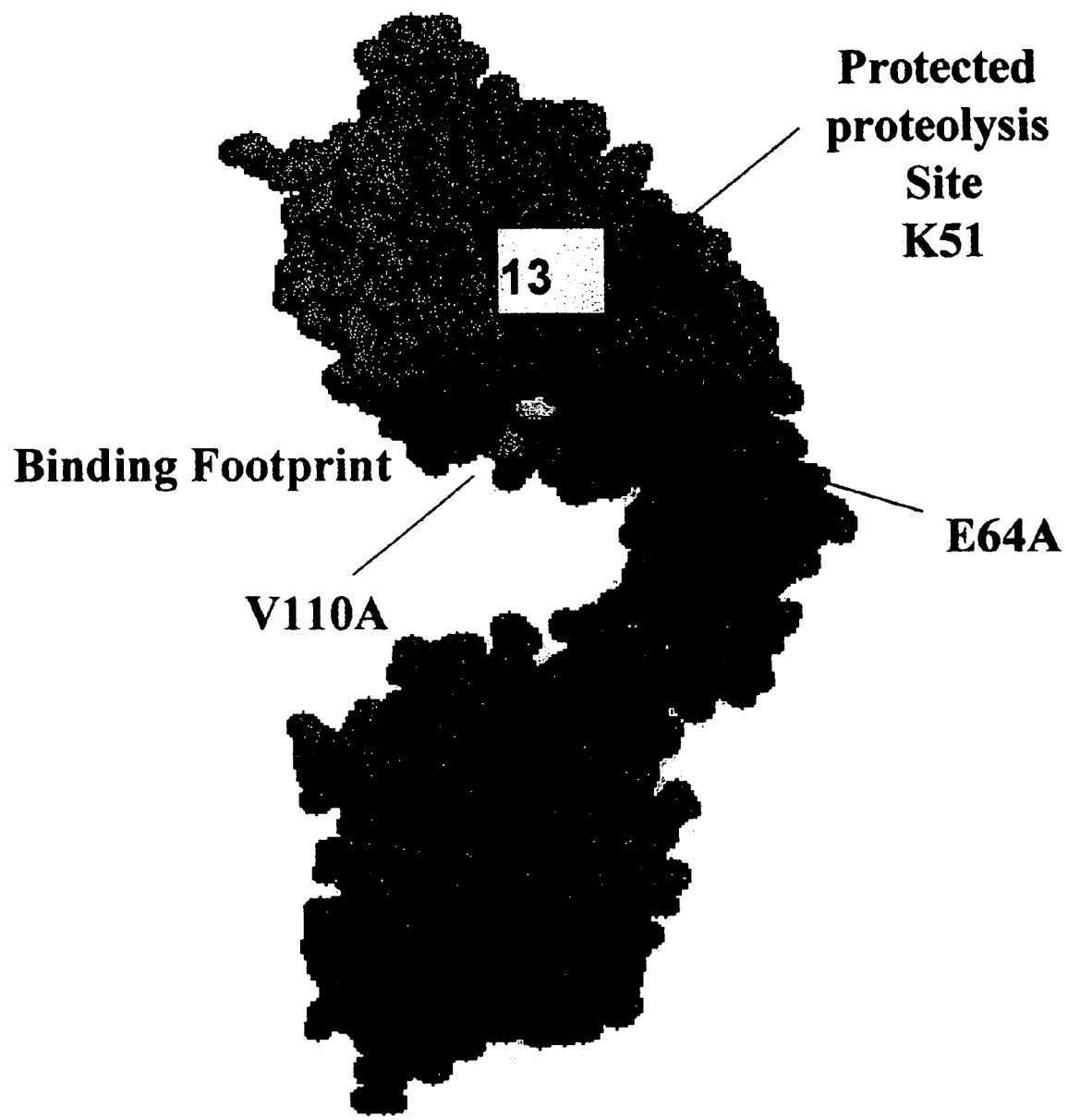
FIG. 13. Space filling model of domains I, II, and III of the structure of IGF-1R showing the positions of the protected proteolysis site (red) and residues E64 (yellow) and V110 (green) in the HER3$^{I-IV}$ mapped to the IGF-1R structure (see, e.g. Garrett et al. (1998) *Nature* 394(6691), 395-9). The hormone binding footprint is in purple. E64 and V110 of HER3$^{I-IV}$ are in or near the binding footprint in domain L1 of IGF-1R.

Residues 64 and 110 are in domain I of HER3 and map to residues H30 and L81 in the hormone binding footprint in the IGF-1R (see, e.g. Garrett et al. (1998) Nature 394(6691), 395-9). (FIG. 13). They are within 12A of each other although they lie on different strands. They are within 22A of the protected proteolysis site (see, e.g. Singer et al. (2001) J Biol Chem 276(47), 44266-74). Their close proximity to each other and the proteolysis site provide evidence that both residues may be involved in ligand binding.

G. Residues 64 and 110 Could Form Specific Interactions with Heregulin

Figure 14:
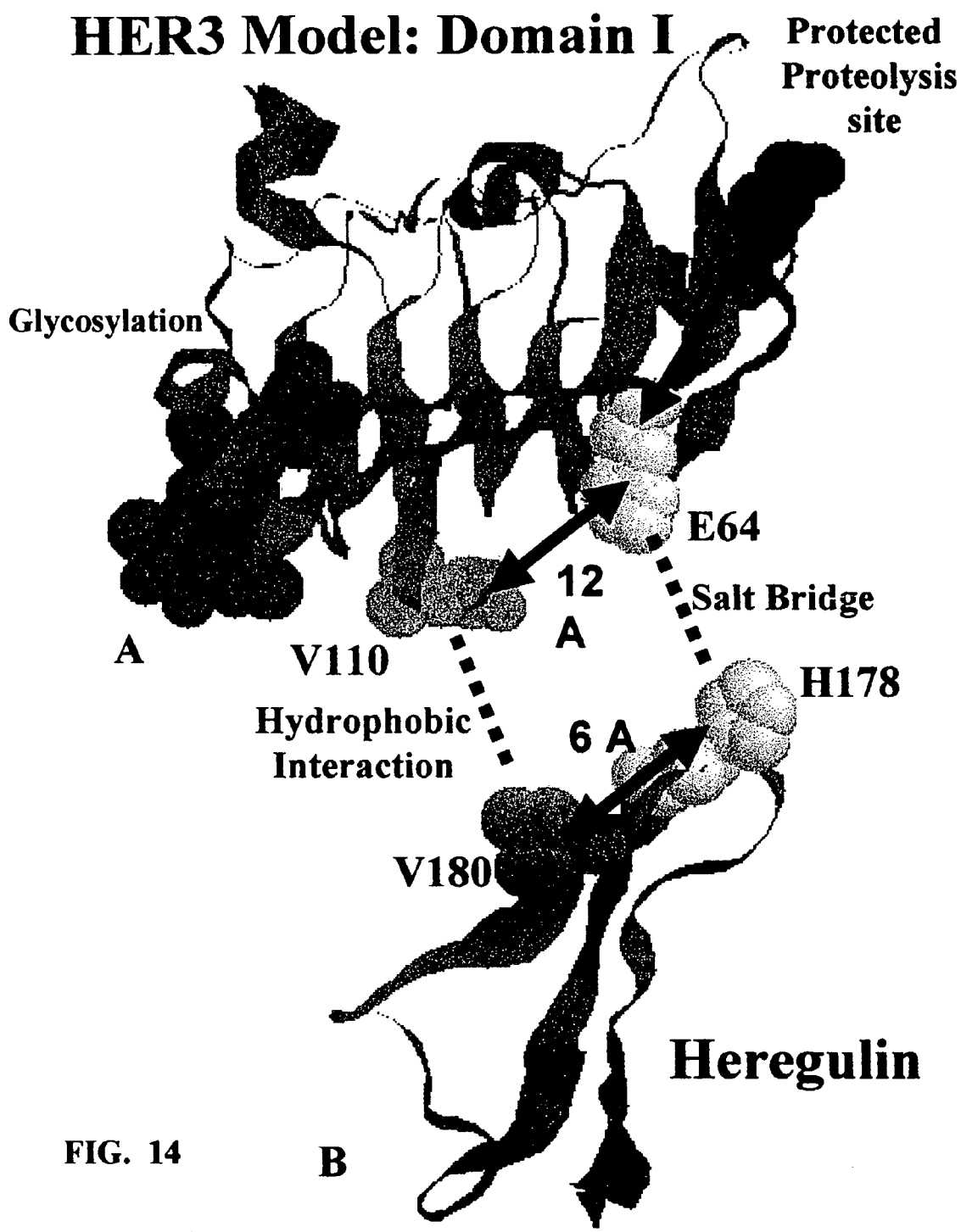
FIG. 14. Residues 64 and 110 could form specific interactions with heregulin. A, Backbone representation of domain I of IGF-1R showing the position of E64 (yellow cpk) and V110 (green cpk) (H30 and L81 in IGF-1R) the residues critical for heregulin binding and the protected proteolysis site at position 50 in HER3$^{I-IV}$ (red cpk) (18 in IGF-1R) superimposed on the IGF-1R structure. E64 (H30 in IGF-1R) and V110 (L81 in IGF-1R) which are critical for heregulin binding are 12 Å from each other and E64 (H30 in IGF-1R) is 13 Å from residue 50 (position 18 in IGF-1R) the protected cleavage site. B, Backbone representation of the EGF-like domain of heregulin showing the position of H178 (yellow cpk) and V180 (green cpk). HER3 V110 and hrg V180 could form hydrophobic interactions. HER3 E64 and hrg H178 could form a salt bridge. These specific interactions could be disrupted by the mutations of E64A and V110A in HER3 as we observed in our biochemical experiments.

The five N-terminal residues of heregulin are required for specific interaction with HER3 (see, e.g. Jones et al. (1998) J Biol Chem 273(19), 11667-74). A valine lies at position 180 and a histidine is at position 178. H3 V110 and hrg V180 could form hydrophobic interactions. H3 E64 and hrg H180 could form a salt bridge. (FIG. 14). Mutation of these residues to alanine could disrupt these specific interactions.

Figure 15:
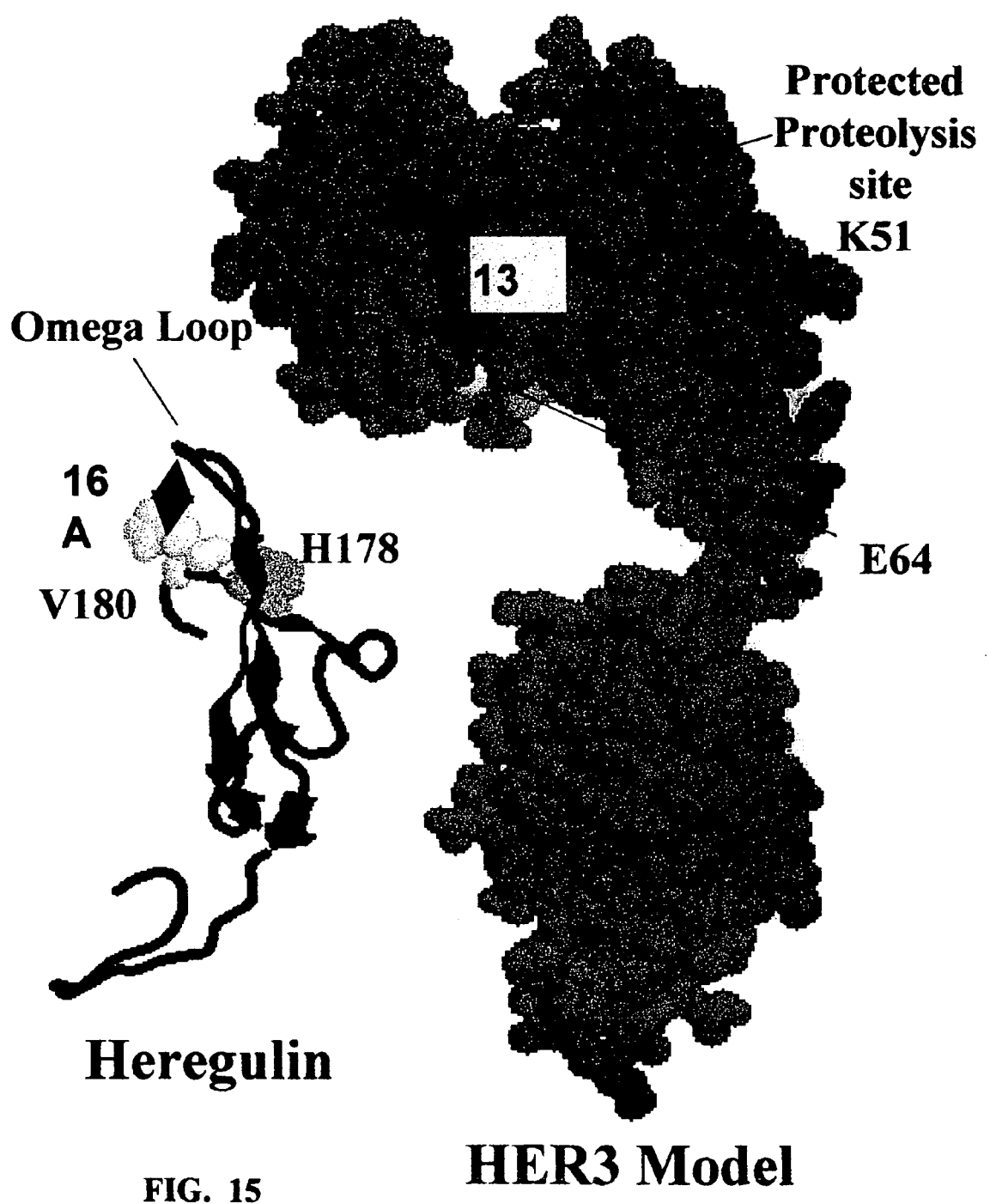
FIG. 15. The N-terminal residues H178 (yellow cpk) and V180 (green cpk) of hrg can form interactions with the residues E64 (yellow cpk) and V110 (green cpk) of HER3 and that the omega loop of hrg could block the protected proteolysis site (residue 50 red cpk) by sterically hindering interaction with trypsin.
Figure 16:
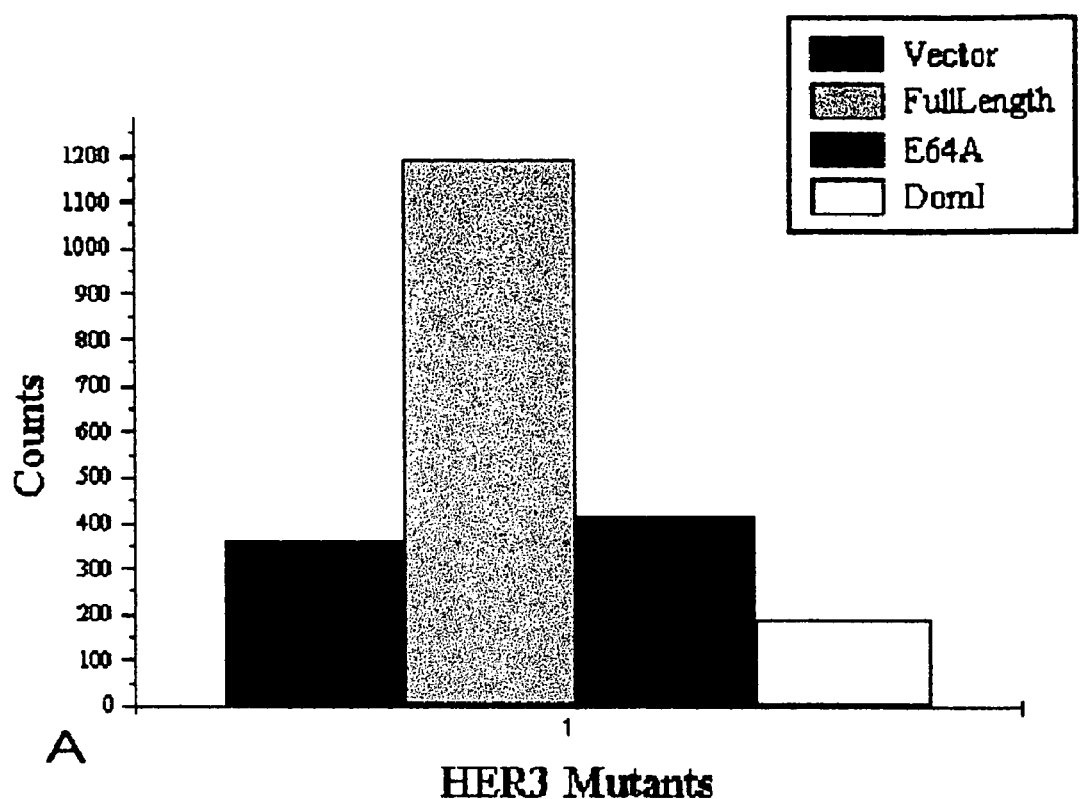
FIG. 16. HER3$^{FL}$ (residues 20-1342) binds heregulin, but HER3$^{FL\ E64A}$ (residues 20-1342 with a mutation of E64A) and HER3$^{II-CTD}$ (Domain I in figure, residues 184-1342) do not. A, Specific binding of I$^{125}$ hrg to COS 7 cells transiently expressing HER3 mutants. The FL HER3 shows a high level of specific binding while the HER3$^{FL\ E64A}$ and HER3$^{II-CTD}$ show similar binding to cells expressing the vector only. B, Western blot analysis of transient expression of the HER3 mutants in COS7 cells. The WT (HER3$^{FL}$), E64A, and Domain I all express similar levels of protein.
Figure 16:
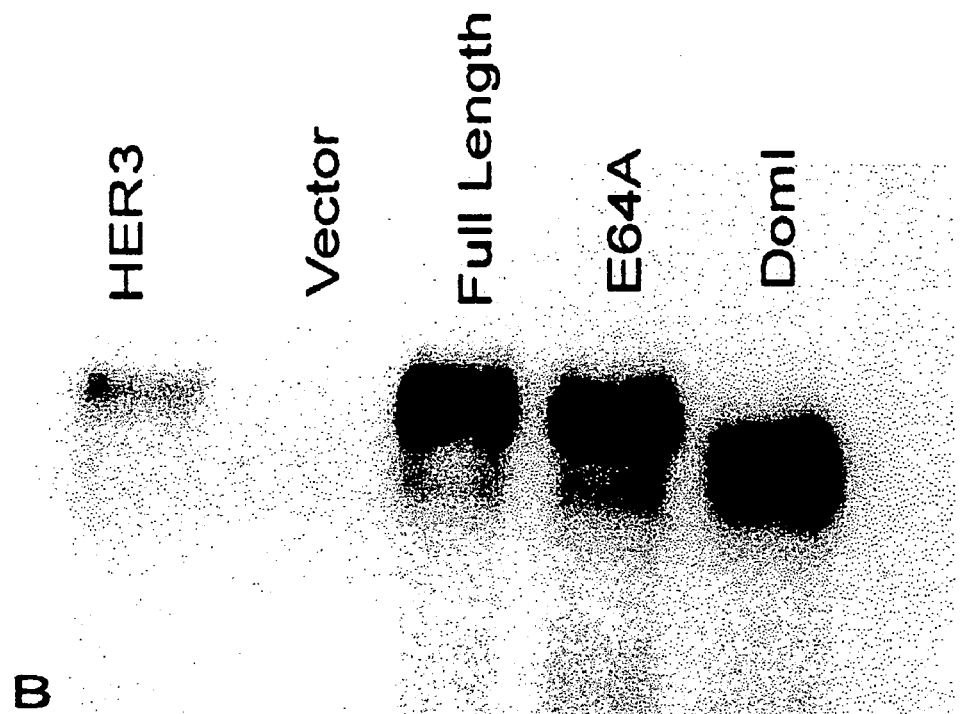

Residue 50 can be protected by hrg from proteolysis but still not be involved directly with hrg binding. Our results provide evidence that residue 50 is not directly involved in hrg binding because a mutation at this site had no effect on hrg binding affinity. We propose that the N-terminus of hrg binds to residues 64 and 110 and that the omega loop blocks the protected proteolysis site (residue 50) by sterically hindering interaction with trypsin (FIG. 15). This figure also shows how hrg in this orientation could fit into the cleft formed by domains I, II, and III as was proposed by (see, e.g. Garrett et al. (1998) Nature 394(6691), 395-9) and (see, e.g. Jorissen et al. (2000) Protein Science 9, 310-324) for the IGF-1R and IR.

We have identified two residues in HER3 that appear to be involved in hrg binding utilizing results from an alanine scanning mutagenesis of the related insulin receptor (see, e.g. Williams et al. (1995) J Biol Chem 270(7), 3012-6) and information from the hormone binding footprint of the known structure of the Insulin growth Factor Receptor (see, e.g. Garrett et al. (1998) Nature 394(6691), 395-9). A multiple sequence alignment of these three receptors allowed us to identify residues which were conserved among all three and were in or near the hormone binding footprint of the IGF-1R (see, e.g. Singer et al. (2001) J Biol Chem 276(47), 44266-74). This allowed us to choose which residues would have the highest probability of forming interactions with heregulin. We identified two residues that were critical for heregulin binding. We observed that complementary residues in heregulin that might form specific interactions with HER3. However, while this analysis implies direct molecular interactions between HER3 and heregulin, it is not direct proof. A high resolution structure of the HER3-heregulin complex is required to confirm these interactions.

TABLE 1

Oligonucleotide sequences used for generating the point mutants.

| N-terminal primer | C-terminal primer |
|---|---|
| HER3 I-II (residue 20) | HER3 I-II (residue 329) |
| CTA CTC TCT AGA TCC GAG GGC AAC TCT | TAC CGA TCT AGA TTT CGG ACA GAG |
| (SEQ ID NO:9) | ACC CCC (SEQ ID NO:10) |

| HER3 Mutants | Plus Strand | Minus Strand |
|---|---|---|
| E43A | GCGATGCTGCGAACCAATACC (SEQ ID NO:11) | GGTATTGGTTCGCAGCATCGC (SEQ ID NO:12) |
| N44A | CGATGCTGAGGCCCAATACCAG (SEQ ID NO:13) | CTGGTATTGGCGCTCAGCATCG (SEQ ID NO:14) |
| K51A | GACACTGTACGCGCTCTACGAG (SEQ ID NO:15) | CTCGTAGAGCCGGTACAGTGTC (SEQ ID NO:16) |
| E64A | GGGAACCTTGCGATTGTGCTC (SEQ ID NO:17) | GAGCACAATCGCAAGGTTCCC (SEQ ID NO:18) |
| V66A | CTTGAGATTGCGCTCACGG (SEQ ID NO:19) | CGTGAGCGCAATCTCAAGGT (SEQ ID NO:20) |
| F94A | CCATGAATGAAGCCTCTACTCTAC (SEQ ID NO:21) | GTAGAGTAGAGCGTTCATTCATGG (SEQ ID NO:22) |
| V110A | GACCCAGGCCTACGATGGGAA (SEQ ID NO:23) | CTTCCCATCGTAGGCCTGGGTC (SEQ ID NO:24) |

TABLE 2

Dissociation constants for the binding of heregulin to alanine mutants of HER3$^{I-II}$. Recombinant HER3 alanine mutants were bound to immobilized hrg on the BIAcore chip. HER3$^{I-II}$ showed binding to immobilized trx-hrg with a calculated equilibrium dissociation constant of 68 nM (see, e.g. Singer et al. (2001) J Biol Chem 276(47), 44266-74). The mutants are designated by the residue being mutated followed by the number indicating the position in the HER3 sequence, followed by alanine. Thus V110A is a mutant in which valine at position 110 has been mutated to alanine. ND > 500 nM indicates that no detectable binding was observed above 500 nM. These results indicate that a mutation of valine at position 110 increased binding affinity 5 fold, while a mutation of the glutamate at position 64 nearly abolished binding affinity.

| H3 I-II Mutant | Kd (nM) |
|---|---|
| E43A | 63.0 +/− 6.4 |
| N44A | 95.5 +/− 15.6 |
| K51A | 63.0 +/− 6.4 |
| E64A | ND > 500 nM |
| V66A | 60.5 +/− 6.3 |
| V110A | 15.4 +/− 3.1 |

TABLE 3

Additional amino acid residues in HER3 associated with heregulin binding as determined by homology, crystallographic and solvent accessibility criteria.

| IGE-1R | HER3 amino acid residues (SEQ ID NO: 2) |
|---|---|
| 5-14 | 30-46 |
| 27-29, 31-36 | 61-63, 65-70 |
| 52-61 | 88-96 |
| 77-79, 81-90 | 106-109, 111-120 |
| 107-115 | 143-151 |
| 133-141 | 169-176 |

Residues include those in HER3 that lay on the face of the HER3 domain that includes the mutated residues characterized herein.

TABLE 4

Illustrative HER3, Heregulin and HER2 polynucleotide and polypeptide sequences:

HER3 Polynucleotide Sequence

SEQ ID NO:1

ATGAGGGCGAACGACGCTCTGCAGGTGCTGGGCTTGCTTTTCAGCCTGGCCCGGGGCTCCGAGGTGGGCAACTCT
CAGGCAGTGTGTCCTGGGACTCTGAATGCCTGAGTGTGACCGGCGATGCTGAGAACCAATACCAGACACTGTAC
AAGCTCTACGAGAGGTGTGAGGTGGTGATGGGGAACCTTGAGATTGTGCTCACGGGACACAATGCCGACCTCTCC
TTCCTGCAGTGGATTCGAGAAGTGACAGGCTATGTCCTCGTGGCCATGAATGAATTCTCTACTCTACCATTGCCC
AACCTCCGCGTGGTGCGAGGGACCCAGGTCTACGATGGGAAGTTTGCCATCTTCGTCATGTTGAACTATAACACC
AACTCCAGCCACGCTCTGCGCCAGCTCCGCTTGACTCAGCTCACCGAGATTCTGTCAGGGGGTGTTTATATTGAG
AAGAACGATAAGCTTTGTCACATGGACACAATTGACTGGAGGGACATCGTGAGGGACCGAGATGCTGAGATAGTG
GTGAAGGACAATGGCAGAAGCTGTCCCCCCTGTCATGAGGTTTGCAAGGGGCGATGCTGGGGTCCTGGATCAGAA
GACTGCCAGACATTGACCAAGACCATCTGTGCTCCTCAGTGTAATGGTCACTGCTTTGGGCCCAACCCCAACCAG
TGCTGCCATGATGAGTGTGCCGGGGGCTGCTCAGGCCCTCAGGACAGACTGCTTTGCCTGCCGGCACTTCAAT
GACAGTGGAGCCTGTGTACCTCGCTGTCCACAGCCTCTTGTCTACAACAAGCTAACTTTCCAGCTGGAACCCAAT
CCCCACACCAAGTATCAGTATGGAGGAGTTTGTGTAGCCAGCTGTCCCCATAACTTTGTGGTGGATCAAACATCC
TGTGTCAGGGCCTGTCCTCCTGACAAGATGGAAGTAGATAAAAATGGGCTCAAGATGTGTGAGCCTTGTGGGGGA
CTATGTCCCAAAGCCTGTGAGGGAACAGGCTCTGGGAGCCGCTTCCAGACTGTGGACTCGAGCAACATTGATGGA
TTTGTGAACTGCACCAAGATCCTGGGCAACCTGGACTTTCTGATCACCGGCCTCAATGGAGACCCCTGGCACAAG
ATCCCTGCCCTGGACCCAGAGAAGCTCAATGTCTTCCGGACAGTACGGGAGATCACAGGTTACCTGAACATCCAG
TCCTGGCCGCCCCACATGCACAACTTCAGTGTTTTTTCCAATTTGACAACCATTGGAGGCAGAAGCCTCTACAAC
CGGGGCTTCTCATTGTTGATCATGAAGAACTTGAATGTCACATCTCTGGGCTTCCGATCCCTGAAGGAAATTAGT
GCTGGGCGTATCTATATAAGTGCCAATAGGCAGCTCTGCTACCACCACTCTTTGAACTGGACCAAGGTGCTTCGG
GGGCCTACGGAAGAGCGACTAGAACATCAAGCATAATCGGCCGCGCAGAGACTGCGTGGCAGAGGGCAAAGTGTGT
GACCCACTGTGCTCCTCTGGGGGATGCTGGGGCCCAGGCCCTGGTCAGTGCTTGTCCTGTCGAAATTATAGCCGA
GGAGGTGTCTGTGTGACCCACTGCAACTTTGTGAATGGGGAGCCTCGAGAATTTGCCCATGAGGCCGAATGCTTC
TCCTGCCACCCGGAATGCCAACCCATGGGGGCACTGCCACATGCAATGCTCGGGCTCTGATACTTGTGCTCAA
TGTGCCCATTTTCGAGATGGGCCCCACTGTGTGAGCAGCTGCCCCCATGGAGTCCTAGGTGCCAAGGGCCCAATC
TACAAGTACCCAGATGTTCAGAATGAATGTCGGCCCTGCCATGAGAACTGCACCCAGGGGTGTAAAGGACCAGAG
CTTCAAGACTGTTTAGGACAAACACTGGTGCTGATCGGCAAAACCCATCTGACAATGCTTTGACAGTGATAGCA
GGATTGGTAGTGATTTTCATGATGCTGGGCGGCACTTTTCTCTACTGGCGTGGGCGCCGGATTCAGAATAAAAGG
GCTATGAGGCGATACTTGGAACGGGGTGAGAGCATAGAGCCTCTGGACCCCAGTGAGAAGGCTAACAAAGTCTTG
GCCAGAATCTTCAAAGAGACAGAGCTAAGGAAGCTTAAGGTGCTTGGCTCGGGTGTCTTTGGAACTGTGCACAAA
GGAGTGTGGATCCCTGAGGGTGAATCAATCAAGATTCCAGTCTGCATTAAAGTCATTGAGGACAAGAGTGGACGG
CAGAGTTTTCAAGCTGTGACAGATCATATGCTGGCCATTGGCAGCCTGGACCATGCCCACATTGTAAGGCTGCTG
GGACTATGCCCAGGGTCATCTCTGCAGCTTGTCACTCAATATTTGCCTCTGGGTTCTCTGCTGGATCATGTGAGA
CAACACCGGGGGCACTGGGGCCACAGCTGCTGCTCAACTGGGGAGTACAAATTGCCAAGGGAATGTACTACCTT
GAGGAACATGGTATGGTGCATAGAAACCTGGCTGCCCGAAACGTGCTACTCAAGTCACCCAGTCAGGTTCAGGTG
GCAGATTTTGGTGTGGCTGACCTGCTGCCTCCTGATGATAAGCAGCTGCTATACAGTGAGGCCAAGACTCCAATT
AAGTGGATGGCCCTTGAGAGTATCCACTTTGGGAAATACACACACCAGAGTGATGTCTGGAGCTATGGTGTGACA
GTTTGGGAGTTGATGACCTTCGGGGCAGACCCTATGCAGGGCTACGATTGGCTGAAGTACCAGACCTGCTAGAG
AAGGGGAGCGGTTGGCACAGCCCCAGATCTGCACAATTGATGTCTACATGGTGATGGTCAAGTGTTGGATGATT
GATGAGAACATTCGCCCAACCTTTAAAGAACTAGCCAATGAGTTCACCAGGATGGCCCGAGACCCACCACGGTAT
CTGGTCATAAAGAGAGAGTGGGCCTGGAATAGCCCCTGGGCAGAGCCCATGGTCTGACAAACAAGAAGCTA
GAGGAAGTAGAGCTGGAGCCAGAACTAGACCTAGACCTAGACTTGGAAGCAGAGGAGGCAACCTGGCAACCACC
ACACTGGGCTCCGCCCTCAGCCTACCAGTTGGAACACTTAATCGGCCACGTGGGAGCCAGAGCCTTTTAAGTCCA
TCATCTGGATACATGCCCATGAACCAGGGTAATCTTGGGGGGTCTTGCCAGGAGTCTGCAGTTTCTGGGAGCAGT

TABLE 4-continued

Illustrative HER3, Heregulin and HER2 polynucleotide and polypeptide sequences:

GAACGGTGCCCCCGTCCAGTCTCTCTACACCCAATGCCACGGGGATGCCTGGCATCAGAGTCATCAGAGGGGCAT
GTAACAGGCTCTGAGGCTGAGCTCCAGGAGAAAGTGTCAATGTGTAGAAGCCGGAGCAGGAGCCGGAGCCCACGG
CCACGCGGAGATAGCGCCTACCATTCCCAGCGCCACAGTCTGCTGACTCCTGTTACCCCACTCTCCCCACCCGGG
TTAGAGGAAGAGGATGTCAACGGTTATGTCATGCCAGATACACACCTCAAAGGTACTCCCTCCTCCCGGGAAGGC
ACCCTTTCTTCAGTGGGTCTCAGTTCTGTCCTGGGTACTGAAGAAGAAGATGAAGATGAGGATGATGAATACATG
AACCGGAGGAGAAGGCACAGTCCACCTCATCCCCCTAGGCCCAAGTTCCCTTGAGGAGCTGGGTTATGAGTACATG
GATGTGGGGTCAGACCTCAGTGCCTCTCTGGGCAGCACACAGAGTTGCCCACTCCACCCTGTACCCATCATGCCC
ACTGCAGGCACAACTCCAGATGAAGACTATGAATATATGAATCGGCAACGAGATGGAGGTGGTCCTGGGGGTGAT
TATGCAGCCATGGGGGCCTGCCCAGCATCTGAGCAAGGGTATGAAGAGATGAGAGCTTTTCAGGGGCCTGGACAT
CAGGCCCCCCATGTCCATTATGCCCGCCTAAAAACTCTACGTAGCTTAGAGGCTACAGACTCTGCCTTTGATAAC
CCTGATTACTGGCATAGCAGGCTTTTCCCCAAGGCTAATGCCCAGAGAACG

HER3 Polypeptide Sequence
SEQ ID NO:2
MRANDALQVLGLLFSLARGSEVGNSQAVCPGTLNGLSVTGDAENQYQTLYKLYERCEVVMGNLEIVLTGHNADLS
FLQWIREVTGYVLVAMNEFSTLPLPNLRVVRGTQVYDGKFAIFVMLNYNTNSSHALRQLRLTQLTEILSGGVYIE
KNDKLCHMDTIDWRDIVRDRDAEIVVKDNGRSCPPCHEVCKGRCWGPGSEDCQTLTKTICAPQCNGHCFGPNPNQ
CCHDECAGGCSGPQDTDCFACRHFNDSGACVPRCPQPLVYNKLTFQLEPNPHTKYQYGGVCVASCPHNFVVDQTS
CVRACPPDKMEVDKNGLKMCEPCGGLCPKACEGTGSGSRFQTVDSSNIDGFVNCTKILGNLDFLITGLNGDPWHK
IPALDPEKLNVFRTVREITGYLNIQSWPPHMHNFSVFSNLTTIGGRSLYNRGFSLLIMKNLNVTSLGFRSLKEIS
AGRIYISANRQLCYHHSLNWTKVLRGPTEERLDIKHNRPRRDCVAEGKVCDPLCSSGGCWGPGPGQCLSCRNYSR
GGVCVTHCNFLNGEPREFAHEAECFSCHPECQPMGGTATCNGSGSDTCAQCAHFRDGPHCVSSCPHGVLGAKGPI
YKYPDVQNECRPCHENCTQGCKGPELQDCLGQTLVLIGKTHLTMALTVIAGLVVIFMMLGGTFLYWRGRRIQNKR
AMRRYLERGESIEPLDPSEKANKVLARIFKETELRKLKVLGSGVFGTVHKGVWIPEGESIKIPVCIKVIEDKSGR
QSFQAVTDHMLAIGSLDHAHIVRLLGLCPGSSLQLVTQYLPLGSLLDHVRQHRGALGPQLLLNWGVQIAKGMYYL
EEHGMVHRNLAARNVLLKSPSQVQVADFGVADLLPPDDKQLLYSEAKTPIKWMALESIHFGKYTHQSDVWSYGVT
VWELMTFGAEPYAGLRLAEVPDLLEKGERLAQPQICTIDVYMVMVKCWMIDENIRPTFKELANEFTRMARDPPRY
LVIKRESGPGIAPGPEPHGLTNKKLEEVELEPELDLDLDLEAEEDNLATTTLGSALSLPVGTLNRPRGSQSLLSP
SSGYMPMNQGNLGGSCQESAVSGSSERCPRPVSLHPMPRGCLASESSEGHVTGSEAELQEKVSMCRSRSRSRSPR
PRGDSAYHSQRHSLLTPVTPLSPPGLEEEDVNGYVMPDTHLKGTPSSREGTLSSVGLSSVLGTEEEDEDEEYEYM
NRRRRHSPPHPPRPSSLEELGYEYMDVGSDLSASLGSTQSCPLHPVPIMPTAGTTPDEDYEYMNRQRDGGGPGGD
YAAMGACPASEQGYEEMRAFQGPGHQAPHVHYARLKTLRSLEATDSAFDNPDYWHSRLFPKANAQRT Heregulin Polynucleotide Sequence
SEQ ID NO:3
ATGTCCGAGCGCAAAGAAGGCAGAGGCAAAGGGAAGGGCAAGAAGAAGGAGCGAGGCTCCGGCAAGAAGCCGGAG
TCCGCGGCGGGCAGCCAGAGCCCAGCCTTGCCTCCCCAATTGAAAGAGATGAAAAGCCAGGAATCGGCTGCAGGT
TCCAAACTAGTCCTTCGGTGTGAAACCAGTTCTGAATACTCCTCTCTCAGATTCAAGTGGTTCAAGAATGGGAAT
GAATTGAATCGAAAAAACAAACCACAAAATATCAAGATACAAAAAAAGCCAGGGAAGTCAGAACTTCGCATTAAC
AAAGCATCACTGGCTGATTCTGGAGAGTATATGTGCAAAGTGATCAGCAAATTAGGAAATGACAGTGCCTCTGCC
AATATCACCATCGTGGAATCAAACGAGATCATCACTGGTATGCCAGCCTCAACTGAAGGAGCATATGTGTCTTCA
GAGTCTCCCATTAGAATATCAGTATCCACAGAAGGAGCAAATACTTCTTCATCTACATCTACATCCACCACTGGG
ACAAGCCATCTTGTAAAATGTGCGGAGAAGGAGAAAACTTTCTGTGTGAATGGAGGGGAGTGCTTCATGGTGAAA
GACCTTTCAAACCCCTCGAGATACTTGTGCAAGTGCCCAAATGAGTTTACTGGTGATCGCTGCCAAAACTACGTA
ATGGCCAGCTTCTACAAGCATCTTGGGATTGAATTTATGGAGGCGGAGGAGCTGTACCAGAAGAGAGTGCTGACC
ATAACCGGCATCTGCATCGCCCTCCTTGTGGTCGGCATCATGTGTGTGGTGGCCTACTGCAAAACCAAGAAACAG
CGGAAAAAGCTGCATGACCGTCTTCGGCAGAGCCTTCGGTCTGAACGAAACAATATGATGAACATTGCCAATGGG
CCTCACCATCCTAACCCACCCCCCGAGAATGTCCAGCTGGTGAATCAATACGTATCTAAAAACGTCATCTCCAGT
GAGCATATTGTTGAGAGAGAAGCAGAGACATCCTTTTCCACCAGTCACTATACTTCCACAGCCCATCACTCCACT
ACTGTCACCCAGACTCCTAGCCACAGCTGGAGCAACGGACACACTGAAAGCATCCTTTCCGAAAGCCACTCTGTA
ATCGTGATGTCATCCGTAGAAAACAGTAGGCACAGCAGCCCAACTGGGGGCCCAAGAGGACGTCTTAATGGCACA
GGAGGCCCTCGTGAATGTAACAGCTTCCTCAGGCATGCCAGAGAAACCCCTGATTCCTACCGAGACTCTCCTCAT
AGTGAAAGGTATGTGTCAGCCATGACCACCCCGGCTCGTATGTCACCTGTAGATTTCCACACGCCAAGCTCCCCC
AAATCGCCCCCTTCGGAAATGTCTCCACCCGTGTCCAGCATGACGGTGTCCATGCCTTCCATGGCGGTCAGCCCC
TTCATGGAAGAAGAGAGACCTCTACTTCTCGTGACACCACCAAGGCTGCGGGAGAAGAAGTTTGACCATCACCCT
CAGCAGTTCAGCTCCTTCCACCACAACCCCGCGCATGACAGTAACAGCCTCCCTGCTAGCCCCTTGAGGATAGTG
GAGGATGAGGAGTATGAAACGACCCAAGAGTACGAGCCAGCCCAAGAGCCTGTTAAGAAACTCGCCAATAGCCGG
CGGGCCAAAAGAACCAAGCCCAATGGCCACATTGCTAACAGATTGGAAGTGGACAGCAACACAAGCTCCCAGAGC
AGTAACTCAGAGAGTGAAACAGAAGATGAAAGAGTAGGTGAAGATACGCCTTTCCTGGGCATACAGAACCCCCTG
GCAGCCAGTCTTGAGGCAACACCTGCCTTCCGCCTGGCTGACAGCAGGACTAACCCAGCAGGCCGCTTCTCGACA
CAGGAAGAAATCCAGGCCAGGCTGTCTAGTGTAATTGCTAACCAAGACCCTATTGCTGTA Heregulin Polypeptide Sequence
SEQ ID NO:4
MSERKEGRGKGKGKKKERGSGKKPESAAGSQSPALPPRLKEMKSQESAAGSKLVLRCETSSEYSSLRFKWFKNGN
ELNRKNKPQNIKIQKKPGKSELRINKASLADSGEYMCKVISKLGNDSASANITIVESNEIITGMPASTEGAYVSS
ESPIRISVSTEGANTSSSTSTSTTGTSHLVKCAEKEKTFCVNGGECFMVKDLSNPSRYLCKCPNEFTGDRCQNYV
MASFYKHLGIEFMEAEELYQKRVLTITGICIALLVVGIMCVVAYCKTKKQRKKLHDRLRQSLRSERNNMMNIANG
PHHPNPPPENVQLVNQYVSKNVISSEHIVEREAETSFSTSHYTSTAHHSTTVTQTPSHSWSNGHTESILSESHSV
IVMSSVENSRHSSPTGGPRGRLNGTGGPRECNSFLRHARETPDSYRDSPHSERYVSAMTTPARMSPVDFHTPSSP
KSPPSEMSPPVSSMTVSMPSMAVSPFMEEERPLLLVTPPRLREKKFDHHPQQFSSFHHNPAHDSNSLPASPLRIV
EDEEYETTQEYEPAQEPVKKLANSRRAKRTKPNGHIANRLEVDSNTSSQSSNSESETEDERVGEDTPFLGIQNPL
AASLEATPAFRLADSRTNPAGRFSTQEEIQARLSSVIANQDPIAV TABLE 4-continued Illustrative HER3, Heregulin and HER2 polynucleotide and polypeptide sequences:

HER2 Polynucleotide Sequence

SEQ ID NO:5

```
ATGGAGCTGGCGGCCTTGTGCCGCTGGGGGCTCCTCCTCGCCCTCTTGCCCCCCGGAGCCGCGAGCACCCAAGTG
TGCACCGGCACAGACATGAAGCTGCGGCTCCCTGCCAGTCCCGAGACCCACCTGGACATGCTCCGCCACCTCTAC
CAGGGCTGCCAGGTGGTGCAGGGAAACCTGGAACTCACCTACCTGCCCACCAATGCCAGCCTGTCCTTCCTGCAG
GATATCCAGGAGGTGCAGGGCTACGTGCTCATCGCTCACAACCAAGTGAGGCAGGTCCCACTGCAGAGGCTGCGG
ATTGTGCGAGGCACCCAGCTCTTTGAGGACAACTATGCCCTGGCCGTGCTAGACAATGGAGACCCGCTGAACAAT
ACCACCCCTGTCACAGGGGCCTCCCCAGGAGGCCTGCGGGAGCTGCAGCTTCGAAGCCTCACAGAGATCTTGAAA
GGAGGGGTCTTGATCCAGCGGAACCCCCAGCTCTGCTACCAGGACACGATTTTGTGGAAGGACATCTTCCACAAG
AACAACCAGCTGGCTCTCACACTGATAGACACCAACCGCTCTCGGGCCTGCCACCCCTGTTCTCCGATGTGTAAG
GGCTCCCGCTGCTGGGGAGAGAGTTCTGAGGATTGTCAGAGCCTGACGCGCACTGTCTGTGCCGGTGGCTGTGCC
CGCTGCAAGGGGCCACTGCCCACTGACTGCTGCCATGAGCAGTGTGCTGCCGGCTGCACGGGCCCCAAGCACTCT
GACTGCCTGGCCTGCCTCCACTTCAACCACAGTGGCATCTGTGAGCTGCACTGCCCAGCCCTGGTCACCTACAAC
ACAGACACGTTTGAGTCCATGCCCAATCCCGAGGGCCGGTATACATTCGGCGCCAGCTGTGTGACTGCCTGTCCC
TACAACTACCTTTCTACGGACGTGGGATCCTGCACCCTCGTCTGCCCCCTGCACAACCAAGAGGTGACAGCAGAG
GATGGAACACAGCGGTGTGAGAAGTGCAGCAAGCCCTGTGCCCGAGTCTGCTATGGTCTGGGCATGGAGCACTTG
CGAGAGGTGAGGGCAGTTACCAGTGCCAATATCCAGGAGTTTGCTGGCTGCAAGAAGATCTTTGGGAGCCTGGCA
TTTCTGCCGGAGAGCTTTGATGGGGACCCAGCCTCCAACACTGCCCCGCTCCAGCCAGAGCAGCTCCAAGTGTTT
GAGACTCTGGAAGAGATCACAGGTTACCTATACATCTCAGCATGGCCGGACAGCCTGCCTGACCTCAGCGTCTTC
CAGAACCTGCAAGTAATCCGGGGACGAATTCTGCACAATGGCGCCTACTCGCTGACCCTGCAAGGGCTGGGCATC
AGCTGGCTGGGGCTGCGCTCACTGAGGGAACTGGGCAGTGGACTGGCCCTCATCCACCATAACACCCACCTCTGC
TTCGTGCACACGGTGCCCTGGGACCAGCTCTTTCGGAACCCGCACCAAGCTCTGCTCCACACTGCCAACCGGCCA
GAGGACGAGTGTGTGGGCGAGGGCCTGGCCTGCCACCAGCTGTGCGCCCGAGGGCACTGCTGGGGTCCAGGGCCC
ACCCAGTGTGTCAACTGCAGCCAGTTCCTTCGGGGCCAGGAGTGCGTGGAGGAATGCCGAGTACTGCAGGGGCTC
CCCAGGGAGTATGTGAATGCCAGGCACTGTTTGCCGTGCCACCCTGAGTGTCAGCCCCAGAATGGCTCAGTGACC
TGTTTTGGACCGGAGGCTGACCAGTGTGTGGCCTGTGCCCACTATAAGGACCCTCCCTTCTGCGTGGCCCGCTGC
CCCAGCGGTGTGAAACCTGACCTCTCCTACATGCCCATCTGGAAGTTTCCAGATGAGGAGGGCGCATGCCAGCCT
TGCCCCATCAACTGCACCCACTCCTGTGTGGACCTGGATGACAAGGGCTGCCCCGCCGAGCAGAGAGCCAGCCCT
CTGACGTCCATCGTCTCTGCGGTGGTTGGCATTCTGCTGGTCGTGGTCTTGGGGGTGGTCTTTGGGATCCTCATC
AAGCGACGGCAGCAGAAGATCCGGAAGTACACGATGCGGAGACTGCTGCAGGAAACGGAGCTGGTGGAGCCGCTG
ACACCTAGCGGAGCGATGCCCAACCAGGCGCAGATGCGGATCCTGAAAGAGACGGAGCTGAGGAAGGTGAAGGTG
CTTGGATCTGGCGCTTTTGGCACAGTCTACAAGGGCATCTGGATCCCTGATGGGGAGAATGTGAAAATTCCAGTG
GCCATCAAAGTCTTGAGGGAAAACACATCCCCCAAAGCCAACAAAGAAATCTTAGACGAAGCATACGTGATGGCT
GGTGTGGGCTCCCCATATGTCTCCCGCCTTCTGGGCATCTGCCTGACATCCACGGTGCAGCTGGTGACACAGCTT
ATGCCCTATGGCTGCCTCTTAGACCATGTCCGGGAAAACCGCGGACGCCTGGGCTCCCAGGACCTGCTGAACTGG
TGTATGCAGATTGCCAAGGGGATGAGCTACCTGGAGGATGTGCGGCTCGTACACAGGGACTTGGCCGCTCGGAAC
GTGCTGGTCAAGAGTCCCAACCATGTCAAAATTACAGACTTCGGGCTGGCTCGGCTGCTTGACATTGACGAGACA
GAGTACCATGCAGATGGGGGCAAGGTGCCCATCAAGTGGATGGCGCTGGAGTCCATTCTCCGCCGGCGGTTCACC
CACCAGAGTGATGTGTGGAGTTATGGTGTGACTGTGTGGGAGCTGATGACTTTTGGGGCCAAACCTTACGATGGG
ATCCCAGCCCGGGAGATCCCTGACCTGCTGGAAAAGGGGGAGCGGCTGCCCCAGCCCCCCATCTGCACCATTGAT
GTCTACATGATCATGGTCAAATGTTGGATGATTGACTCTGAATGTCGGCCAAGATTCCGGGAGTTGGTGTCTGAA
TTCTCCCGCATGGCCAGGGACCCCCAGCGCTTTGTGGTCATCCAGAATGAGGACTTGGGCCCAGCCAGTCCCTTG
GACAGCACCTTCTACCGCTCACTGCTGGAGGACGATGACATGGGGGACCTGGTGGATGCTGAGGAGTATCTGGTA
CCCCAGCAGGGCTTCTTCTGTCCAGACCCTGCCCCGGGCGCTGGGGGCATGGTCCACCACAGGCACCGCAGCTCA
TCTACCAGGAGTGGCGGTGGGGACCTGACACTAGGGCTGGAGCCCTCTGAAGAGGAGGCCCCCAGGTCTCCACTG
GCACCCTCCGAAGGGGCTGGCTCCGATGTATTTGATGGTGACCTGGGAATGGGGGCAGCCAAGGGGCTCCAAAGC
CTCCCCACACATGACCCCAGCCCTCTACAGCGGTACAGTGAGGACCCCACAGTACCCCTGCCCTCTGAGACTGAT
GGCTACGTTGCCCCCCTGACCTGCAGCCCCCAGCCTGAATATGTGAACCAGCCAGATGTTCGGCCCCAGCCCCCT
TCGCCCCGAGAGGGCCCTCTGCCTGCTGCCCGACCTGCTGGTGCCACTCTGGAAAGGGCCAAGACTCTCTCCCCA
GGGAAGAATGGGGTCGTCAAAGACGTTTTTGCCTTTGGGGGTGCCGTGGAGAACCCCGAGTACTTGACACCCCAG
GGAGGAGCTGCCCCTCAGCCCCACCCTCCTCCTGCCTTCAGCCCAGCCTTCGACAACCTCTATTACTGGGACCAG
GACCCACCAGAGCGGGGGGCTCCACCCAGCACCTTCAAAGGGACACCTACGGCAGAGAACCCAGAGTACCTGGGT
CTGGACGTGCCAGTG
```

HER2 Polypeptide Sequence

SEQ ID NO:6

```
MELAALCRWGLLLALLPPGAASTQVCTGTDMKLRLPASPETHLDMLRHLYQGCQVVQGNLELTYLPTNASLSFLQ
DIQEVQGYVLIAHNQVRQVPLQRLRIVRGTQLFEDNYALAVLDNGDPLNNTTPVTGASPGGLRELQLRSLTEILK
GGVLIQRNPQLCYQDTILWKDIFHKNNQLALTLIDTNRSRACHPCSPMCKGSRCWGESSEDCQSLTRTVCAGGCA
RCKGPLPTDCCHEQCAAGCTGPKHSDCLACLHFNHSGICELHCPALVTYNTDTFESMPNPEGRYTFGASCVTACP
YNYLSTDVGSCTLVCPLHNQEVTAEDGTQRCEKCSKPCARVCYGLGMEHLREVRAVTSANIQEFAGCKKIFGSLA
FLPESFDGDPASNTAPLQPEQLQVFETLEEITGYLYISAWPDSLPDLSVFQNLQVIRGRILHNGAYSLTLQGLGI
SWLGLRSLRELGSGLALIHHNTHLCFVHTVPWDQLFRNPHQALLHTANRPEDECVGEGLACHQLCARGHCWGPGP
TQCVNCSQFLRGQECVEECRVLQGLPREYVNARHCLPCHPECQPQNGSVTCFGPEADQCVACAHYKDPPFCVARC
PSGVKPDLSYMPIWKFPDEEGACQPCPINCTHSCVDLDDKGCPAEQRASPLTSIVSAVVGILLVVVLGVVFGILI
KRRQQKIRKYTMRRLLQETELVEPLTPSGAMPNQAQMRILKETELRKVKVLGSGAFGTVYKGIWIPDGENVKIPV
AIKVLRENTSPKANKEILDEAYVMAGVGSPYVSRLLGICLTSTVQLVTQLMPYGCLLDHVRENRGRLGSQDLLNW
CMQIAKGMSYLEDVRLVHRDLAARNVLVKSPNHVKITDFGLARLLDIDETEYHADGGKVPIKWMALESILRRRFT
HQSDVWSYGVTVWELMTFGAKPYDGIPAREIPDLLEKGERLPQPPICTIDVYMIMVKCWMIDSECRPRFRELVSE
FSRMARDPQRFVVIQNEDLGPASPLDSTFYRSLLEDDDMGDLVDAEEYLVPQQGFFCPDPAPGAGGMVHHRHRSS
STRSGGGDLTLGLEPSEEEAPRSPLAPSEGAGSDVFDGDLGMGAAKGLQSLPTHDPSPLQRYSEDPTVPLPSETD
GYVAPLTCSPQPEYVNQPDVRPQPPSPREGPLPAARPAGATLERAKTLSPGKNGVVKDVFAFGGAVENPEYLTPQ
GGAAPQPHPPPAFSPAFDNLYYWDQDPPERGAPPSTFKGTPTAENPEYLGLDVPV
```

What is claimed is:

1. A HER3 variant polypeptide comprising SEQ ID NO: 2 having an amino acid substitutions at residue position V110.

2. The HER3 variant polypeptide of claim 1, wherein the HER3 variant polypeptide is conjugated or linked to one or more polyol groups.

3. The HER3 variant polypeptide of claim 1, wherein the HER3 variant polypeptide has an alanine substitution at V110.

4. The HER3 variant polypeptide of claim 1, wherein the HER3 variant polypeptide comprises a soluble, extracellular domain HER3 polypeptide.

* * * * *